(12) United States Patent
Alibakhsh et al.

(10) Patent No.: US 11,580,603 B2
(45) Date of Patent: *Feb. 14, 2023

(54) SYSTEM AND METHOD FOR PROVIDING REAL-TIME BI-DIRECTIONAL CHARGE CAPTURE-CENTRALIZED CONVERSATION BETWEEN BILLING AND PROVIDER ENTITIES

(71) Applicants: Massoud Alibakhsh, Atlanta, GA (US); Shahram Famorzadeh, Marietta, GA (US)

(72) Inventors: Massoud Alibakhsh, Atlanta, GA (US); Shahram Famorzadeh, Marietta, GA (US)

( * ) Notice: Subject to any disclaimer, the term of this patent is extended or adjusted under 35 U.S.C. 154(b) by 164 days.

This patent is subject to a terminal disclaimer.

(21) Appl. No.: 16/553,150

(22) Filed: Aug. 27, 2019

(65) Prior Publication Data

US 2019/0392948 A1  Dec. 26, 2019

Related U.S. Application Data

(63) Continuation of application No. 13/841,072, filed on Mar. 15, 2013, now Pat. No. 10,395,005.

(51) Int. Cl.
 *G06Q 40/08* (2012.01)
 *G06Q 10/10* (2012.01)
 (Continued)

(52) U.S. Cl.
 CPC .............. *G06Q 40/08* (2013.01); *G06Q 10/10* (2013.01); *G16H 10/00* (2018.01); *G16H 40/20* (2018.01); *G16H 50/00* (2018.01)

(58) Field of Classification Search
 CPC ........ G06Q 40/08; G06Q 10/10; G16H 40/20; G16H 10/00; G16H 50/00
 See application file for complete search history.

(56) References Cited

U.S. PATENT DOCUMENTS

| 2007/0005402 A1* | 1/2007 | Kennedy | G06Q 40/08 |
| | | | 705/4 |
| 2012/0330685 A1* | 12/2012 | Hasan | G06Q 10/10 |
| | | | 705/3 |
| 2013/0339062 A1* | 12/2013 | Brewer | H04W 4/021 |
| | | | 705/4 |

FOREIGN PATENT DOCUMENTS

EP       1736926 A1 * 12/2006   ........... G07F 7/1008

OTHER PUBLICATIONS

Wire2Air 360 Interactive Mobile Solutions Unveiled Video Messaging &Picture Messaging (MMS), Aug. 9, 2012, PR Newswire Association. (Year: 2012).*

* cited by examiner

*Primary Examiner* — Christopher L Gilligan
(74) *Attorney, Agent, or Firm* — Richard C. Piercy; Grell & Watson Patent Attorneys LLC

(57) ABSTRACT

A system for providing real-time bi-directional charge capture-centralized conversation between Billing and Provider entities, comprising a first computer apparatus with a computer apparatus charge capture module installed and a second computer apparatus with a computer apparatus billing module installed that are used to transmit and/or receive real-time charge capture centralized conversation data. Real-time charge capture-centralized conversation data is comprised of real-time charge capture data. The real-time charge capture data and the real-time charge capture-centralized conversation data can be combined to create real-time claim data. The system further comprises first computer apparatus and second computer apparatus receipt and transmission via secured communication links. The real-time charge capture data, real-time charge capture-centralized conversation data and real-time claim data is presented in a social media conversation style format. The first computer apparatus and (Continued)

second computer apparatus make it possible for both a Billing and a Provider entity to initiate, transmit or modify any of the sets of real-time charge capture data or real-time charge capture-centralized conversation data.

20 Claims, 68 Drawing Sheets

(51) Int. Cl.
  *G16H 10/00* (2018.01)
  *G16H 50/00* (2018.01)
  *G16H 40/20* (2018.01)

Charge Capture

⊕ Start a new Charge Capture

Messages

| | Chun Yong | Oct 19, 2012 |
| | Dr. Jones we need a copy of ... | 5:07 pm |

| | Sean Ogawa | Oct 19, 2012 |
| | That should work | 3:07 pm |

| | AJ Johnson | Oct 19, 2012 |
| | I need additional documentat... | 2:45 pm |

| | Lisa Hodges | Oct 19, 2012 |
| | Her home address | 11:09 am |

| | Craig Nielson | Oct 19, 2012 |
| | Here you go | 2:45 pm |

| | Erik Truex | Oct 19, 2012 |
| | Yes | 11:09 am |

| | Kurt Crinklaw | Oct 19, 2012 |
| | What's the status of this Amy? | 2:45 pm |

| | Tyrone Points | Oct 19, 2012 |
| | Confirmed | 11:09 am |

| | Donna Washington | Oct 19, 2012 |
| | 404 124 1254 | 2:45 pm |

| | Guy Benny | Oct 19, 2012 |
| | No | 11:09 am |

More

619, 502 — Cancel | New Patient | Save — 620

First Name:

621 — [ ]

Last Name:

622 — [ ]

Date of Birth:

623 — [ ]

Gender:

624 — [ ]

Phone Number:

625 — [ ]

Patent Photo:

626 — [ ◎ Add Photo ]

Other Patient Attachments:

627 — [ ◎ Add Picture ]
628 — [ 🎤 Add Dictation ]

| Cancel | New Patient | Save |

First Name:

Last Name:

Date of Birth: 633

Error

Please enter a first name, last name, date of birth, and gender in order to continue.

OK

Patient Photo:

[◎] Add Photo

Other Patient Attachments:

[◎] Add Picture
[🎤] Add Dictation

620 ← 610

| Cancel | New Patient | Save |

First Name:

Chun

Last Name:

Yong

Date of Birth: 634

Warning

A patient already exists with the information you just provided. Are you sure you want to create this new patient?

No | Yes

Patient Photo:

[◎] Add Photo

Other Patient Attachments:

[◎] Add Picture
[🎤] Add Dictation

| Charge Details | Charge Attachments | Patient Attachments |

Charge for John Smith (12/11/1956)
Provider. Ted Jones     DOS: 03/01/2012
Location. Atlanta     Facility: Emergency Room
Last Updated by Ted Jones on Mar 1, 2012 12:21 pm

Diagnoses:
1. 786.20   Cough
2. 780.60   Fever,unspecified

Procedures:
88213   EatPatientOV
Unit. 1   Dx. 1.2   Mode. TO   DOS: 03/01/2012

~906

You @ Mar 1,2012 12:45 pm     Read
Dr. Jones we need a copy of the patients face sheet. Do you mind sending that here?

Ted Jones @ Mar 1,2012 1:05 pm     Read
Face Sheet
Photo
☑ Keep with Patient

You @ Mar 1, 2012 1:10 pm     Read
Dr. Jones we need a copy of your assessment for this visit. Can you snap a picture of the note and add it here?

Ted Jones @ Mar 1,2012 4:38 pm   Unread
The assessment for which Diagnosis?

~905

| Type Your message here | Send |

| Home | Patient | Ticket | Appt. | Live Help | Exit | Insurance | View | Notes |
|------|---------|--------|-------|-----------|------|-----------|------|-------|

| Inbox | Open Charges | Finalized Charges | Search Results |
|-------|--------------|-------------------|----------------| fpattaata (8)

✉ Ben Smith (5) ✉ ① JOHN SMITH — Mar 1, 2012
                       Ted Jones Charge    4:38 pm ✉ Mery Buckner    ✉ ① SANDY JONES (New Patient) — Mar 1, 2012
                       Ted Jones Charge    11:34 am ✉ Ted Jones (3)    ✉ ① CRAIG NIELSON — Mar 1, 2012
                       Ted Jones Charge    11:31 am fpattaata (5)

✉ Conrad Lantear    ✉ DONNA WASHINGTON — Feb 28, 2012
                       Ted Jones Charge    1:12 pm ✉ Justina Dragal (4)    ✉ SALVATOR CORLEONE — Feb 23, 2012
                       Ted Jones C[...]

✉ Rusemary Fifield (1)    ✉ CHRIS JOEL[...]
                       Ted Jones C[...]

ⓘ Description

File Name. Patient Face Sheet.png
Please enter a description for this Attach

FIGURE 10B

| Home | Patient | Ticket | Appt. | Live Help | Exit |  |  | Insurance | View |  |
|---|---|---|---|---|---|---|---|---|---|---|

Inbox fpattaata (8)

| | Open Charges | Finalized Charges | Search Results | Notes | | Charg |
|---|---|---|---|---|---|---|
| ✉ | JOHN SMITH<br>Ted Jones Charge | | | Mar 1, 2012<br>4:38 pm | | Provid<br>Locati<br>Last U |
| ✉ | SANDY JONES<br>Ted Jones Charge | | | Mar 1, 2012<br>11:34 am | | Diagno<br>1. 786.<br>2. 780 |
| ✉ | CRAIG NIELSON<br>Ted Jones Charge | | | Mar 1, 2012<br>11:31 am | | Proced<br>88213 |

Ben Smith (5)
✉ Mery Buckner
✉ Ted Jones (3)

fpattaata (5)
✉ Conrad Lantear
✉ Justina Dragal (4)
✉ Rusemary Fifield (1)

| ✉ | DONNA WASHINGTON<br>Ted Jones Charge | Feb 28, 2012<br>2:12 pm |
|---|---|---|
| ✉ | SALVATOR CORLEONE<br>Ted Jones Char | Feb 23, 2012 |

Finalize

The selected charge(s) has been Finalized

[ OK ]

| ✉ | CHRIS JOEL<br>Ted Jones Char |
|---|---|

| Charge Details | Charge Attachments | Patient Attachments |

Charge for John Smith (12/11/1956)
Provider: Ted Jones        DOS: 03/01/2012
Location: Atlanta          Facility: Emergency Room
*Last Updated by Ted Jones on Mar 1, 2012 12:21 pm*

Diagnoses:
1. 786.20  Cough
2. 780.60  Fever, unspecified

Procedures:
88213  EatPatentOV
  Dx. 1.2  Mode. TO  DOS: 03/01/2012

You @ Mar 1, 2012 12:45 pm        Read
Dr. Jones we need a copy of the patients face sheet. Do you mind sending that here?

Ted Jones @ Mar 1, 2012 1:05 pm  Read
Face Sheet
Photo
☑ Keep with Patient

You @ Mar 1, 2012 1:10 pm         Read
Dr. Jones we need a copy of your assessment for first visit. Can you snap a picture of the note and add it here?

Ted Jones @ Mar 1, 2012 1:05 pm  Unread
The assessment for which Diagnosis?

| Type Your message here | Send |

| | |
|---|---|
| Appt.   Live Help   Exit | Insurance   View   Notes |

Open Charges | Finalized Charges | Search Results

| | | |
|---|---|---|
| ✉ | JOHN SMITH<br>Ted Jones Charge | Mar 1, 2012<br>4:38 pm |
| ✉ | SANDY JONES<br>Ted Jones Charge | Mar 1, 2012<br>11:34 am |
| ✉ | CRAIG NIELSON<br>Ted Jones Charge | Mar 1, 2012<br>11:31 am |
| ✉ | SAUNDRA MCCAUGH<br>Ted Jones Charge | Mar 1, 2012<br>11:04 am |
| ✉ | LORRIE HARLIN<br>Ted Jones Charge | Mar 1, 2012<br>10:33 am |
| ✉ | MAX BDEHME<br>Ted Jones Charge | Mar 1, 2012<br>10:01 am |
| ✉ | PENELOPE SUMRELL<br>Ted Jones Charge | Mar 1, 2012<br>9:36 am |
| ✉ | CLYTON BUENDIA<br>Ted Jones Charge | Mar 1, 2012<br>9:00 am |
| ✉ | NOEMI BYLEY<br>Ted Jones Charge | Mar 1, 2012<br>8:27 am |
| ✉ | RARREN VILLALVAZO<br>Ted Jones Charge | Mar 1, 2012<br>8:11 am |
| ✉ | DOLLIE WILKEN<br>Ted Jones Charge | Feb 28, 2012<br>4:37 pm |
| ✉ | NELSON WALWORTH<br>Ted Jones Charge | Feb 28, 2012<br>4:02 pm |
| ✉ | PEARLIE FAIRBANK<br>Ted Jones Charge | Feb 28, 2012<br>3:32 pm |
| ✉ | DARRYL LINGENFELTER<br>Ted Jones Charge | Feb 28, 2012<br>2:23 pm |

1611

Search Charges (Enter patient name) 🔍 ◇

| Add Attachment | Open | Scrub | |
|---|---|---|---|

| Appt. | Live Help | Exit | Insurance | View | Notes |

| Open Charges | Finalized Charges | Search Results |

| JOHN SMITH | Mar 1, 2012 |
| Ted Jones Charge | 4:38 pm |
| SANDY JONES | Mar 1, 2012 |
| Ted Jones Charge | 10:32 am |
| CRAIG NELSON | Mar 1, 2012 |
| Ted Jones Charge | 10:55 am |

1706

Search Charges (Enter Patient name)

| Add. Attachment | Finalize | Scrub |

| Appt. | Live Help | Exit | Insurance | View | Notes |

| Open Charges | Finalized Charges | Search Results |

| ✉① JOHN SMITH | Mar 1, 2012 |
| Ted Jones Charge | 4:38 pm |
| ✉① SANDY JONES *(New Patient)* | Mar 1, 2012 |
| Ted Jones Charge | 11:34 am |
| ✉① CRAIG NIELSON — 1802 | Mar 1, 2012 |
| Ted Jones Charge | 11:31 am |
| ✉① ERIK TRUEX | Feb 28, 2012 |
| Ben Smith Charge | 2:12 pm |
| ✉① KURT CRINKLAW | Feb 28, 2012 |
| Ben Smith Charge | 1:54 pm |
| ✉① TYRONE POINTS | Feb 28, 2012 |
| Ben Smith Charge | 1:43 pm |
| ✉ DONNA WASHINGTON | Feb 28, 2012 |
| Ted Jones Charge | 1:12 pm |
| ✉① GUY BENNY | Feb 28, 2012 |
| Ben Smith Charge | 12:17 pm |
| ✉① EVE URMAN | Feb 28, 2012 |
| Ben Smith Charge | 11:39 am |
| ✉ SALVATOR CORLEONE | Feb 23, 2012 |
| Ted Jones Charge | 4:54 pm |
| ✉ CHRIS JOEL | Feb 21, 2012 |
| Ted Jones Charge | 8:49 am |

Search Charges (Enter Patient Name) 🔍 ◇

| Add Attachment | Finalize | Scrub |

FIGURE 18B

| | | |
|---|---|---|
| Appt. Live Help Exit | Insurance View Notes | |
| Open Charges | Finalized Charges | Search Results |
| ✉① TOM LEE Ted Jones Charge | Mar 1, 2012 4:38 pm | |
| ✉① SANDY JONES *(New Patient)* Ted Jones Charge | Mar 1, 2012 11:34 am | |
| ✉① CRAIG NIELSON Ted Jones Charge | Mar 1, 2012 11:31 am | |
| ✉① ERIK TRUEX Ben Smith Charge | Feb 28, 2012 2:12 pm | |
| ✉① KURT CRINKLAW Ben Smith Charge | Feb 28, 2012 1:54 pm | |
| ✉① TYRONE POINTS Ben Smith Charge | Feb 28, 2012 1:43 pm | |
| ✉ DONNA WASHINGTON Ted Jones Charge | Feb 28, 2012 1:12 pm | |
| ✉① GUY BENNY Ben Smith Charge | Feb 28, 2012 12:17 pm | |
| ✉① EVE URMAN Ben Smith Charge | Feb 28, 2012 11:39 am | |
| ✉ SALVATOR CORLEONE Ted Jones Charge | Feb 23, 2012 4:54 pm | |
| ✉ CHRIS JOEL Ted Jones Charge | Feb 21, 2012 8:49 pm | |
| ✉ SALVATOR CORLEONE Ted Jones Charge | Feb 23, 2012 4:54 pm | |
| ✉ CHRIS JOEL Ted Jones Charge | Feb 21, 2012 8:49 am | |

Display More Charge

Search Charges (Enter Patient Name) 🔍

Add Attachment | Finalize | Scrub

SYSTEM AND METHOD FOR PROVIDING REAL-TIME BI-DIRECTIONAL CHARGE CAPTURE-CENTRALIZED CONVERSATION BETWEEN BILLING AND PROVIDER ENTITIES

CROSS-REFERENCE TO RELATED APPLICATIONS

To the full extent permitted by law, the present United States Non-provisional Patent Application is a continuation of and hereby claims priority to and the full benefit of, United States Provisional Application entitled "SYSTEM AND METHOD FOR PROVIDING REAL-TIME BI-DIRECTIONAL CHARGE CAPTURE-CENTRALIZED CONVERSATION BETWEEN BILLING AND PROVIDER ENTITIES" having assigned Ser. No. 13/841,072, filed on Mar. 15, 2013, which is incorporated herein by reference in its entirety.

FEDERALLY SPONSORED RESEARCH OR DEVELOPMENT

None

PARTIES TO A JOINT RESEARCH AGREEMENT

None

REFERENCE TO A SEQUENCE LISTING

None

BACKGROUND OF THE DISCLOSURE

Technical Field of the Disclosure

The present invention relates generally to billing practices in the healthcare industry. Specifically, it relates to a system and method for providing real-time charge capture-centralized conversation between Billing and Provider entities.

Description of the Related Art

An important activity to the success of the healthcare industry is fast, accurate billing practices. Thus, a critical component of any Provider's organization is the successful processing and billing of medical claims to various payers. Because of the gap in time between a service/product recipient visit and the billing of that visit, the passage of time and handlers amplify the negative impact of error, confusion, and omission. While there are many applications and devices on the market that seek to improve the accuracy of documentation from the actual service/product recipient encounter as it occurs, there remains considerable need for improving the speed and accuracy of the billing process.

Claim scrubbing and other forms of error checking are a few of the most common ways Provider and Billing entities verify accuracy of final billing prior to sending it to the designated payer. However, despite these efforts to increase accuracy, human error and inconsistency is unavoidable and often creates delay. One common reason for delay is confusion on the Billing entity's behalf regarding entries from a service/product recipient encounter. Although some Providers use sophisticated applications and devices that reduce coding errors from diagnoses, many do not. Furthermore, there are currently no applications or devices that are robust enough to prevent most errors from free form typing, incorrect code selection, sloppy handwriting, obscure diagnoses, missing documentation, etc. To correct these problems, once the Billing entity receives the documentation, it must follow up with the Provider and wait for a response.

Healthcare is a fast-paced industry; communication between Billing and Provider entities can be extremely challenging, usually taking anywhere between two to four weeks before charges can be finalized and transmitted. Additionally, the means of such communication (phone calls and emails) are inconvenient for both parties. There have also been cases where Providers do not respond to queries at all, resulting in certain claims remaining unfiled. This delay understandably creates a longer distance from point of service to accurate billing and submission for payment. Investing in front-end applications and devices that reduce errors during the service/product recipient encounter is thus only partially responsive to the back-end problem of delay. Without also addressing the delay caused by the necessary conversations between the Billing entities and the Providers, the efficiency of revenue realization from service/product recipient encounters suffers for the Provider, the Billing entities, and the insurance companies. Reduction in overhead to execute necessary processes often initiates reductions in healthcare costs. Thus, by addressing these delays, Providers and insurance companies stand to benefit from process improvement passing this gain on to service/product recipients.

The Kovacevic, et al. patent application; having U.S. patent application Ser. No. 13/272,182; filed Oct. 12, 2011; and entitled, Methods and Systems for Health Care Record, Workflow, and Billing Management Using Mobile Devices"; discloses one attempt to eliminate delays in billing processing by focusing on a mobile platform that provides health care record, workflow management, and medical billing features. This method focuses on making typical healthcare-related desktop application functionality available via a mobile device. The mobile device option allows Providers who provide services outside of their primary practice location and/or who work as a team the ability to communicate and collaborate while rendering their services.

This method seeks to simplify and expedite the associated billing procedures by providing a front-end interface that aggregates relevant data from a broad base of internal and external data sources. The front-end interface is capable of dynamic communication with back-end servers and data repositories. This communication design enhances efficiency and accuracy of billing by capturing missed charges and shortening the billing cycle during the process. However, despite this method's efficacy in improving the quality and speed of gathering service/product recipient encounter documentation, the underlying back-end delay from inevitable human error remains largely unaddressed.

The Malhotra et al. patent application; having U.S. patent application Ser. No. 10/842,316; filed May. 10, 2004; and entitled, "Physicians' Remote Charge Capture System"; discloses another system that focuses on eliminating billing procedure delay. This method describes an information system for physicians and their staff that is available via the web so physicians providing services in hospitals on behalf of other physicians can update the service/product recipient records accordingly. The ability to update the records in this fashion reduces extensive overhead in record keeping and contributes to the accuracy of service/product recipient records. Specifically, this accuracy greatly facilitates the organization and management of vitally important tasks such as contact, diagnoses, level of services rendered or procedures performed, service/product recipient status and physician workload management and distribution. Information regarding services or procedures rendered is documented in the web module and can then be combined with supplemental service/product recipient information stored elsewhere on the Provider's network.

Some billing delay improvements are an obvious by-product of this method because of the reduction in delay of service/product recipient information entry. The sooner the physicians can document their services or procedures rendered, the sooner the Provider can bill for those services or procedures and hence, the sooner the Provider can expect payment from the payer. As referenced, this method discusses an additional 'office computer' on the Provider's network that stores supplemental service/product recipient information accessible by a physician's office administrator. This supplemental information, when combined with the electronic physician entry helps facilitate more efficient billing because the combination of physician- entered data and the supplemental data constitute a complete billing record for the encounter. However, there is no further discussion in this method of any specific efficiency targeted to the necessary error-checking component of the back-end billing processes. Further, this method does not consider the delay caused by error checking, or facilitating and expediting the required communication. Without considering these details, this method also leaves the problem the current invention identifies completely unaddressed.

The Strayer patent application; having U.S. patent application Ser. No. 10/011,596; filed Feb. 13, 2002; and entitled, "System and Software for Capturing and Encoding Healthcare Services and Processing Healthcare Claims"; discloses yet another system that attempts to reduce billing procedure delay by utilizing a front-end point of service (POS) system that allows the Provider to document the service/product recipient encounter using the system. The system is designed with diagnoses and procedure codes already built in, removing a significant amount of human error from the encounter entry process the Provider simply selects from embedded menus of options. From the encounter, the Provider then submits the documentation to a centralized coding facility. In this form, the documentation is referred to as a 'super bill,' a list that itemizes the services a physician has provided for purposes of billing. The central coding facility effectively parses the super bill appropriately based on payer, scrubs the claims, and then submits the claims electronically. By having the appropriate codes built in to the system the Provider uses to document the encounter, the initial coding step is eliminated.

The centralized coding facility then further reduces delay by error checking the claims and handles the electronic submission and associated reimbursement. Much of the system's efficiency is targeted to the front-end encoding that enables automatic, electronic submission to the centralized coding facility. However, the problematic delay identified in the current invention is not resolved with this system either. Once the super bill reaches the centralized coding facility, the super bill still requires parsing and it is indisputable some errors still exist requiring claim scrubbing or further correspondence between the Billing and the Provider entities. Furthermore, electronic submission of the scrubbed claims from the coding facility is a logical step most Providers use these days in one form or another, thus it introduces little if any reduction in current billing delay otherwise.

The Toleti, et al. patent application; having U.S. patent application Ser. No. 12/891,074; filed Sep. 27, 2010; and entitled, system a Method for Real Time Healthcare Billing and Collection"; discloses a further method for the elimination of delays in the billing procedures by automating a large portion of the service/product recipient encounter. This method suggests a physician use an electronic clipboard or tablet to document information from the encounter. While the physician is providing service to the service/product recipient, the diagnoses and codes being entered are being sent to a back-end coder to verify for accuracy and generation of a super bill. Most errors made during the service/product recipient encounter by the physician are corrected in real-time by the coder, then upon completion of the visit, the super bill is electronically submitted to payers that support electronic submission, or is otherwise posted for immediate submission non-electronically. Those payers that support electronic submission accept the claim(s) and generate an EOB (Explanation of Benefits) to send back to the physician's office. The Physician's office receives the EOB, calculates the difference between the charges and the allowable coverage, and directs the service/product recipient to a kiosk in the office to settle the remaining service/product recipient liability.

Ultimately, this system and method seeks to address delays across all points of the service/product recipient encounter, but relies heavily on payers accepting electronic claim submission and service/product recipient willingness/ability to pay immediately to deliver the true improvement to the delay in billing processes. Additionally, the preferred embodiment mentions a person operating the coder machine on the backend. An alternate embodiment mentioned is automation of the coder - however, in either case, human error, unavailability, connectivity problems, system problems or a variety of other issues may arise effectively removing the error-checking function from the method's process. If any of the aforementioned links (coder, electronic claim submission, or service/product recipient payment ability) fail, significant expected efficiency is lost.

Furthermore, the system's inventor makes several erroneous assertions regarding how EOBs are administered from payers. First, while it is true that most payers accept electronic claim submission, not all accept direct electronic claim submission. Many payers require the use of a clearinghouse that then forwards the claims on to the payer. The use of a clearinghouse has the potential to delay any communication from the payer at least half a day or more. Second, regardless of whether a clearinghouse is used, most payers do not automatically provide an EOB to the service/product recipient or its equivalent, an ERA (Electronic Remittance Advice) to the Provider. There is a further error-checking step that must occur on the payer's end before a claim is processed and its status in EOB or ERA form is communicated back to the Provider or service/product recipient. The communication of the EOB or ERA often takes a day or two, sometimes more—making in-office service/product recipient payment impossible.

Third, even if, arguendo, payers issued immediate EOBs and ERAs, they do not issue immediate payment to Providers. Some payers utilize EFT (Electronic Funds Transmission) technology to electronically pay Providers, but this process always takes at least several days. For those payers that do not utilize EFT, payment comes in the form of a paper check through regular mail to the Provider, which can take anywhere from several days to several weeks. Thus, very little, if any billing or revenue recognition efficiency stands to be recognized beyond the error checking the coder function performs during the service/product recipient encounter (i.e. 'first-level claim scrubbing')

Several other ideas of interest hit the market recently in the medical industry as the technology age pushes increasing portability and communication speed. Many recent applications seek to provide mobile access to traditionally desktop based applications (i.e. practice management (PM), electronic health records (EHR), and electronic medical records (EMR)) Most of these applications are integrated with their respective desktop versions, and hence cannot stand alone. Furthermore, most of these applications rely on backend storage of service/product recipient information to facilitate effective point of service charge capture and notifications from office staff to Providers. None, thus far, has been fully functional in an integrated OR stand-alone environment. Likewise, none has provided complete bi-directional communication between the Provider and the Billing entity and wholly focused on the charge-capture aspect of the encounter process.

Despite the commonality of the familiar real-time communication tools of email and text or messaging paradigms found in social media-styled conversation on smart phones, not a single application has emerged to integrate this user familiarity with billing business necessity in the way the current inventors have. In fact, most of the mobile applications on the market that use real-time communication target workflow areas like scheduling, rounds management, census information, automatic, built-in coding and claim scrubbing, prescriptions, etc. Many applications advertise the capability of mobile, point of service charge capturing, but revert to inefficient or no back-end bi-directional communication with the Billing entity. Some applications permit Provider or Billing entities to append attachments to service/product recipient files and charges, but none organize this critical information around the charge capture instance itself, further relying on a PM, EHR or EMR to catalogue the data with the service/product recipient, thereby hindering convenient mobile access to this information at a later date.

Technology in the medical industry shows heavy focus on automation and improved customer interaction, but still largely ignores the back-end process. Automation and improved customer interaction are concepts that clearly improve the efficiency of the front-end encounter process, possibly explaining why existing back-end inefficiencies remain unaddressed.

In light of the current state of the art, it is readily apparent that a comprehensive solution to back-end billing procedure delays is needed. Automating the service/product recipient encounters via mobile devices and/or automating the coding component in an effort to reduce delay only address part of the problem. The current state of the art does not provide a solution to the delays caused by back-end errors in the claims themselves, even after they have been scrubbed. The back-end errors require communication between the Provider and the Billing entity that often takes significant time if not designed effectively. Thus, there is a need for a system and method for providing real-time bi-directional charge-capture centralized conversation between Billing and Provider entities. Real-time conversation automatically reduces inherent delay. Centralizing the conversation around a charge-capture further reduces delay by removing extraneous details (a.k.a. 'noise'), only focusing on the critical information needed for billing accurately.

BRIEF SUMMARY OF THE INVENTION

Briefly described, in a preferred embodiment, the present invention overcomes the above-mentioned disadvantages and meets the recognized need for such a device by providing a system and method for providing real-time bi-directional charge capture-centralized conversation between Billing and Provider entities. The present system and method is for use in health care management systems. Specifically, the system and method is for use during the billing procedure phase of a Provider's service. Further uses include other industries that have billing phases driven by delivery of service encounters where separate entities provide services then forward a list of those 2services to a Billing entity to decipher and invoice accordingly. Most importantly, the present invention is well suited for business models that require efficient billing practices following delivery of service. Such industries may include maintenance and repair services, insurance adjustment, utility installation, etc.

Achieving efficiency in billing practices requires a reduction in error-induced delays. The present invention achieves this reduction by providing Billing entities a real-time opportunity to converse with Providers regarding errors, questions, missing documentation or other details of a service encounter that would prevent the Billing entity from being able to submit for payment immediately upon receipt.

The present invention introduces a new module with a messaging capability (a.k.a. 'conversation') between the Billing and Provider entities that created the documentation (charge capture). The module provides the conversation using an email interface combined with the paradigm of texting and messaging, akin to social media styled-conversation. The centerpiece of the module is the charge itself, with all attendant conversation regarding documentation, prior messages, service/product recipient information, etc. that has occurred over time between the Billing and Provider entity, in a sortable thread.

In the preferred embodiment, there is a first computer apparatus portion with a computer apparatus charge capture module and a second computer apparatus portion with a computer apparatus billing module. On the second computer apparatus portion, the messages between the Billing and Provider entities sort by charge in a familiar Inbox-styled format, allowing Billing entities to quickly cycle through charges to gather all of the information they need before filing the claims. The module also allows users to preview charges, scrub charges, send and receive messages, add (via a computer apparatus' peripheral device) and view attachments, and organize charge messages. On the first computer apparatus portion, an enhancement to the charge capture application provides the ability to view and send messages, view and edit previously made charges, and add attachments (via the computer apparatus' peripheral device) to charge captures.

In one example, a Billing entity receives super bills from multiple different Providers. In the event the Billing entity is using an integrated billing system, the charge captures are tickets within the billing system because the Provider is using the same system to document the service/product recipient (a.k.a. service/product recipient) encounter. In an integrated billing system, the Billing entity will be able to select a particular Provider practice (if applicable), drill to a particular Provider within that practice, and then further drill to the charge capture the Provider has entered, about which the Billing entity needs to have a conversation. By starting or continuing a conversation thread centered on the charge capture, the physician then receives the message on the first computer apparatus portion and can supply the requested information immediately.

In an alternate example, a Billing entity receives super bills from multiple different Providers in a non-integrated billing system. In this case, the Billing entity will need to create a ticket (or record) in the second computer apparatus portion with a computer apparatus billing module of the present invention for the charge capture. In a non-integrated system, the ticket created in the computer apparatus billing module functions very similarly to the ticket already present in the integrated module. Likewise, by starting or continuing a conversation thread centered on the charge capture, the physician then receives the message on the computer apparatus charge capture portion and can supply the requested information immediately.

One benefit of the present invention is a significant reduction in billing procedure delays. Mobile devices and applications increasingly employ real-time, secure mobile communication like text messaging and email (social media-styled conversation). Real-time communication reduces or eliminates the delays existing Billing entities experience when trying to reach Providers.

Another benefit of the present invention is the centralization around the charge capture itself. By limiting extraneous information from the conversation, Billing entities and Providers can have focused concise conversations about the charges only. This focus makes it easier for busy Providers to receive, read, and respond to messages in a shorter period. Furthermore, transmission speed of messages in the conversation is shorter due to the sending of less information in any singular message (e.g. charge capture information only w/ limited service/product recipient demographic information as opposed to full service/product recipient file). The conversation thread grows as it is compiled based on messages, but any information added to the thread (pictures, documents, etc.) are stored on the secure network and associated with the particular charge capture for easy later access, but do not continuously transmit with each message.

Yet another benefit of the present invention is its ability to store historical threads and reactivate them when necessary. Conversations are current as they are occurring, however once the Billing entity determines all necessary information has been received, the charge capture can be marked finalized and hidden from active view. The hidden thread disappears from the active view, but remains accessible via the search option. In the event the charge capture needs reopening, searching for the hidden thread and simply posting a new message to it will reactivate the entire thread, enabling prioritization and historic thread content to reactivate. This feature prevents duplicitous activities while simultaneously minimizing unnecessary active content clutter.

The primary goal of this system and method is to provide a real-time conversation method that effectively handles any Billing entity inquiry as efficiently as possible. By using common messaging protocols found in social media-styled conversation, mobile devices, and a secured network, conversations between Providers and Billing entities occur quickly but remain completely secure. As a result, charge capture finalization and submission for payment to payers occurs more quickly. Reducing the submission delay automatically reduces the delay Providers would ordinarily experience for information on payment remittance (ERA and/or EFS). Likewise, the sooner Providers receive information on payment remittance the sooner invoicing for service/product recipient liability occurs (EOB receipt and after).

The secondary goal of this system and method is to reduce the amplification effect that gaps in time have on Providers' memory of service/product recipient encounters. Similar to the primary goal: a total reduction in delays yields not only more efficient billing practices but better quality information from busy Providers that deal with many service/product recipients on a daily basis. Better quality information undoubtedly enhances the quality of the overall charge capture finalization, introducing fewer errors that service/product recipients must deal with when receiving EOBs and invoices from Providers.

BRIEF DESCRIPTION OF THE SEVERAL VIEWS OF THE DRAWINGS

The present invention will be better understood by reading the Detailed Description of the Preferred and Selected Alternate Embodiments with reference to the accompanying drawing figures, in which like reference numerals denote similar structure and refer to like elements throughout, and in which:

FIG. 5D is a screen shot view of an exemplary computer apparatus charge capture interface screen depicting the existing open charge-centered messages pane portion of a charge capture template, according to FIG. 5A and FIG. 5B;

FIG. 6E is a screen shot view of an exemplary computer apparatus charge capture interface screen depicting a sub-template of a charge capture template image for adding a new service/product recipient, according to FIG. 6A;

FIG. 6G is a screen shot view of an exemplary computer apparatus charge capture interface screen depicting a sub-template of a charge capture template image for adding a new service/product recipient with error messages, according to FIG. 6A and FIG. 6E;

FIG. 16B is a screen shot view of an exemplary computer apparatus billing module interface screen depicting a tabbed Charges pane in the middle, 'Finalized Charges' tab active, according to FIG. 9A;

Figure 18A:
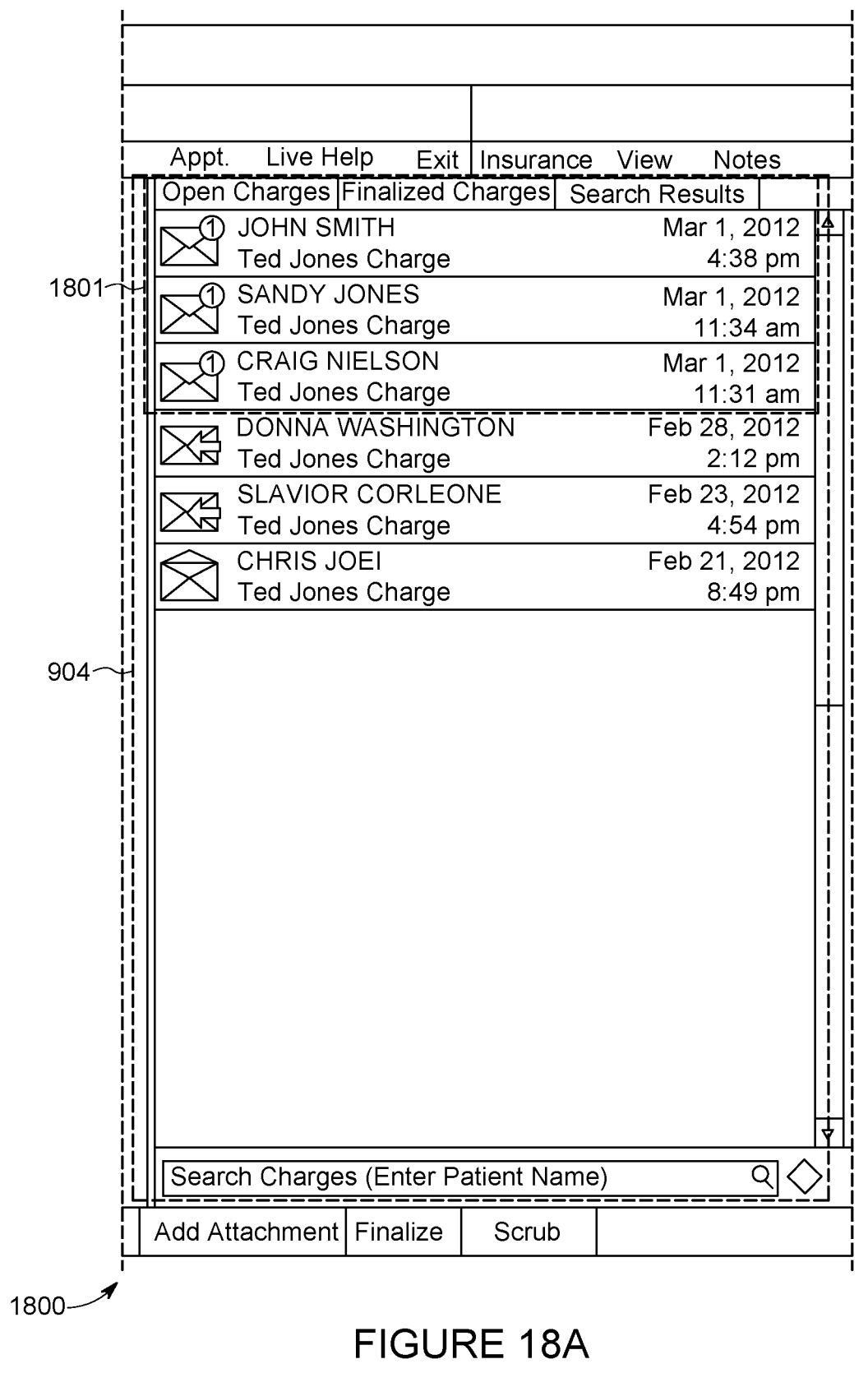

FIG. 18A is a screen shot view of an exemplary computer apparatus billing module interface screen depicting a tabbed Charges pane in the middle, 'Open Charges' tab active, according to FIG. 9A, showing the multiple charge selection capability;

FIG. 18B is a screen shot view of an exemplary computer apparatus billing module interface screen depicting a tabbed Charges pane in the middle, 'Open Charges' tab active, according to FIG. 9A, showing 'New Service/product recipient' indicator;

FIG. 18C is a screen shot view of an exemplary computer apparatus billing module interface screen depicting a tabbed Charges pane in the middle, 'Open Charges' tab active, according to FIG. 9A, showing 'Display More Charges' button;

FIG. 19A is a screen shot view of an exemplary computer apparatus billing module interface screen depicting a tabbed Preview pane on the top right, with the 'Charge Details' tab active, according to FIG. 9A;

FIG. 19B is a screen shot view of an exemplary computer apparatus billing module interface screen depicting a tabbed Preview pane on the top right, with the 'Charge Attachments' tab active, according to FIG. 9A;

It is to be noted that the drawings presented are intended solely for the purpose of illustration and that they are, therefore, neither desired nor intended to limit the disclosure to any or all of the exact details of construction shown, except insofar as they may be deemed essential to the claimed disclosure.

It is to be noted that the drawings presented are intended solely for the purpose of illustration and that they are, therefore, neither desired nor intended to limit the disclosure to any or all of the exact details of the construction shown, except insofar as they may be deemed essential to the claimed disclosure.

DETAILED DESCRIPTION OF THE PREFERRED AND SELECTED ALTERNATE EMBODIMENTS OF THE INVENTION

In describing the exemplary embodiment of the present disclosure, as illustrated in FIGS. 1-20, specific terminology is employed for the sake of clarity. The present disclosure, however, is not intended to be limited to the specific terminology so selected, and it is to be understood that each specific element includes all technical equivalents that operate in a similar manner to accomplish similar functions. Embodiments of the claims may, however, be embodied in many different forms and should not be construed to be limited to the embodiments set forth herein. The examples set forth herein are non- limiting examples, and are merely examples among other possible examples.

Figure 1:
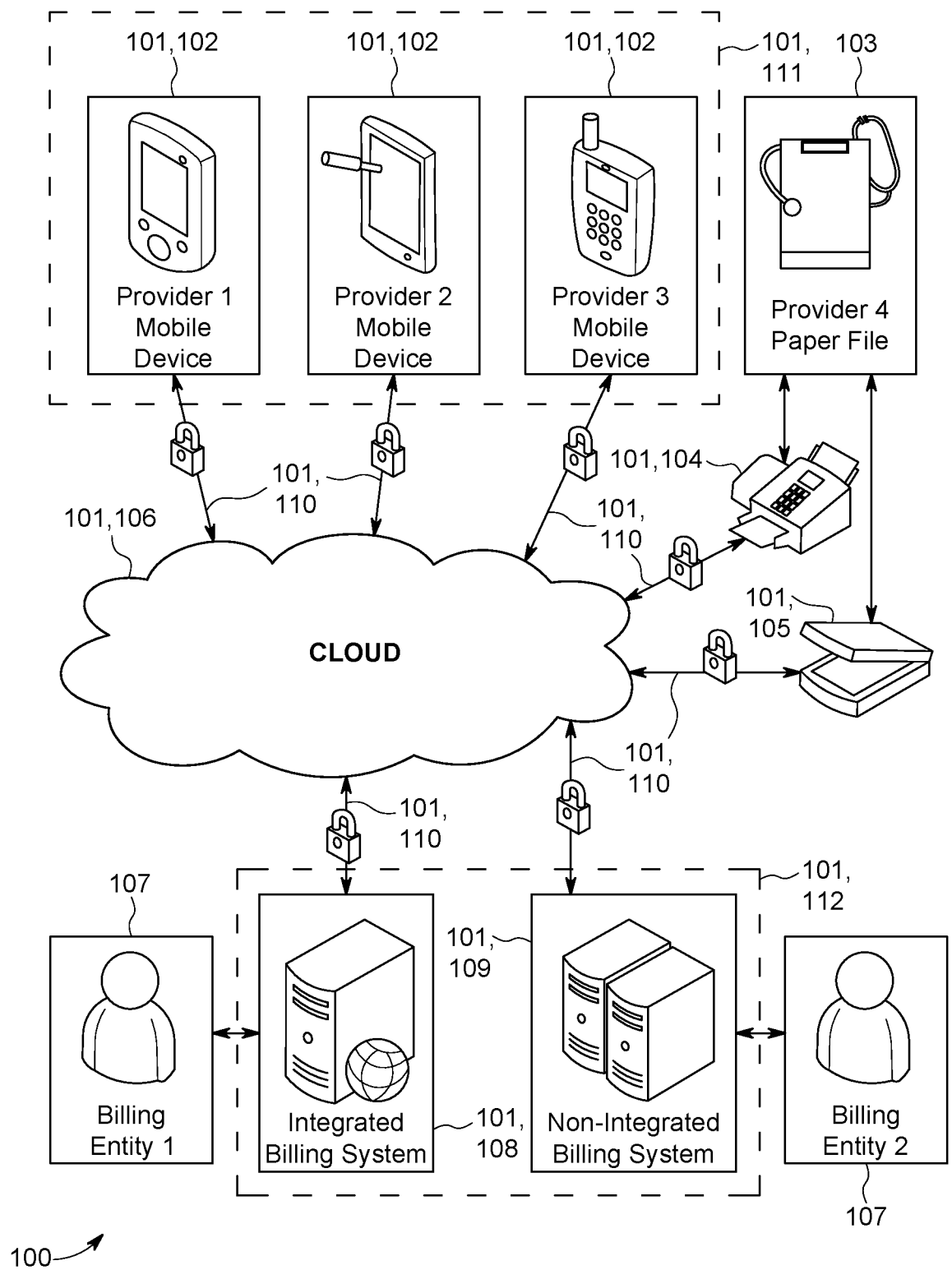
FIG. 1 is a block diagram depicting a preferred and an alternate embodiment of a secure network showing Provider and Billing entity communication.
Figure 4:
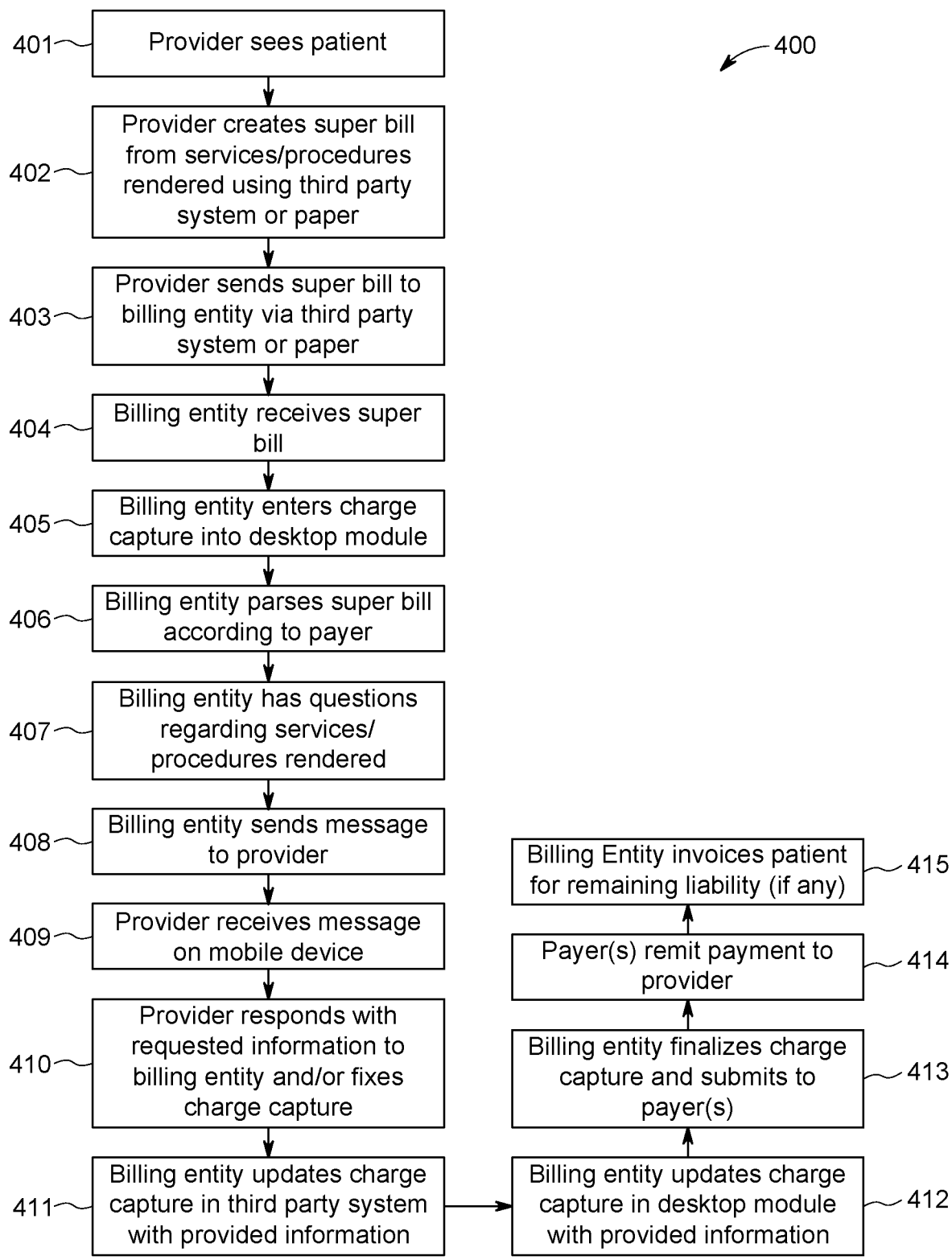
FIG. 4 is a flowchart depicting the general process between a Provider and Billing entity from service/product recipient encounter to payment remittance, via an alternate embodiment.
Figure 5A:
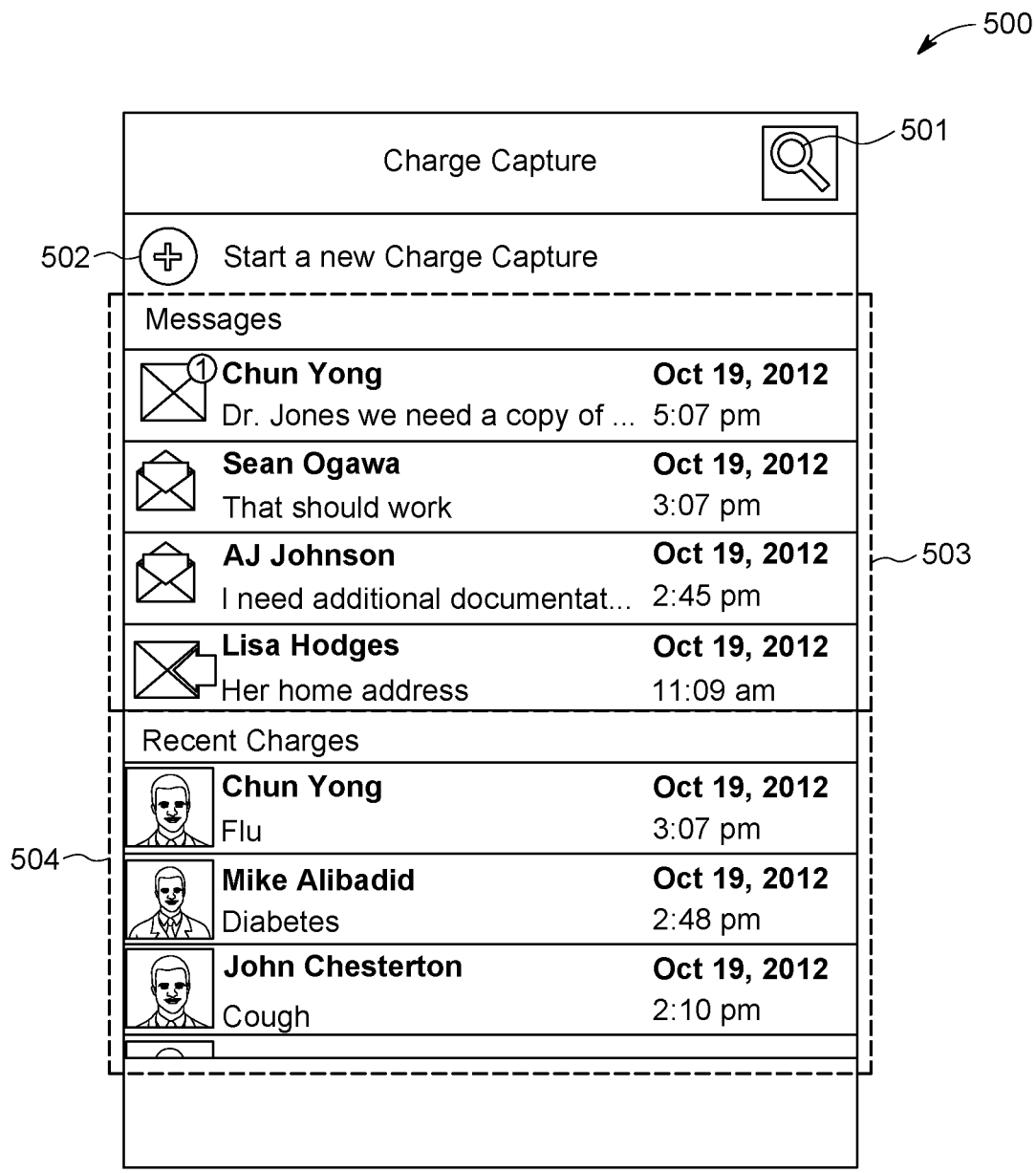
FIG. 5A is a screen shot view of an exemplary computer apparatus charge capture interface screen depicting a charge capture template image with an existing open charge-centered messages pane portion on the top and a recent existing charges created by the user pane portion on the bottom, according to an exemplary embodiment.
Figure 8A:
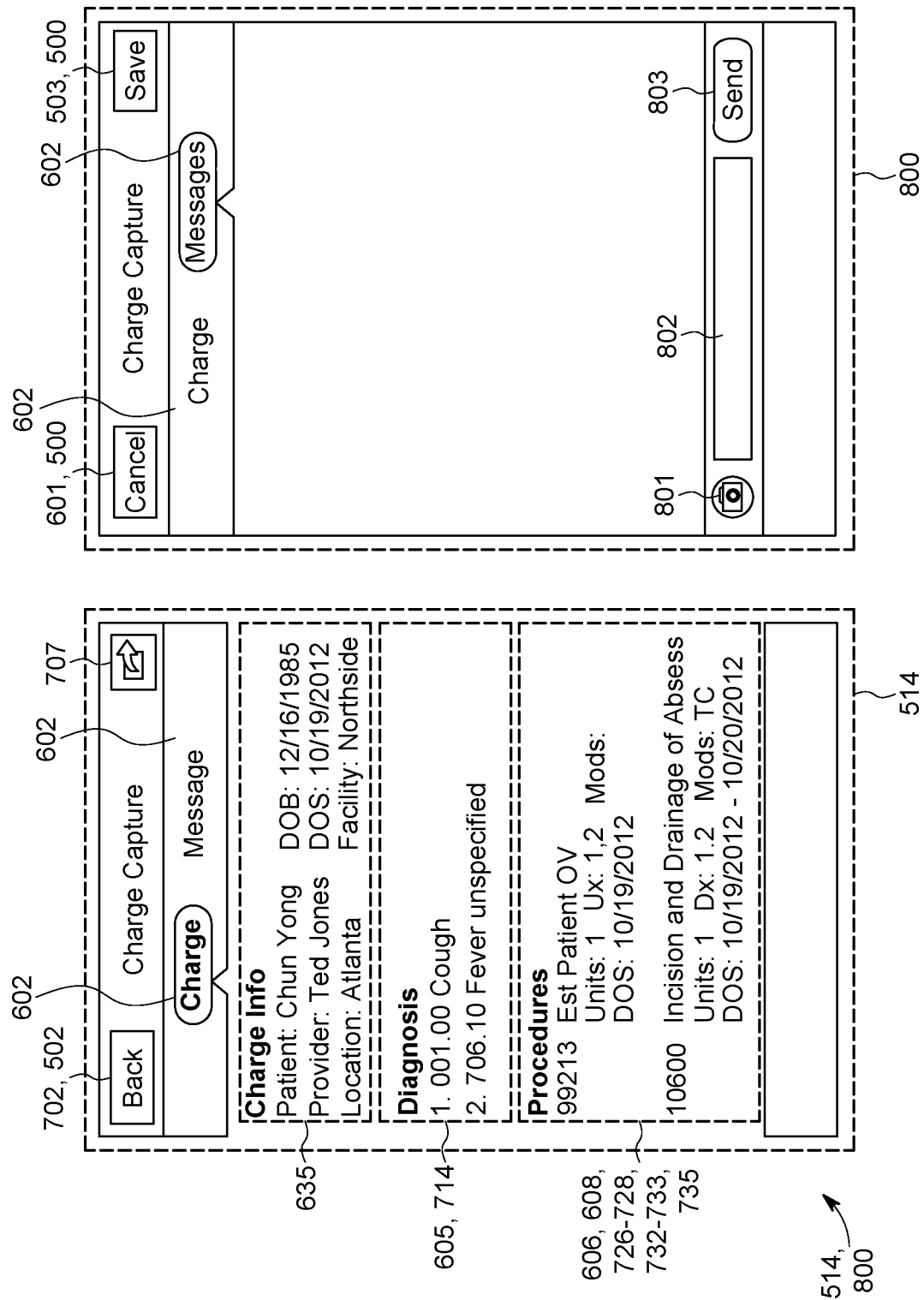
FIG. 8A is a screen shot view of an exemplary computer apparatus charge capture interface screen depicting the display of a selection of a recent existing charge created by the user of a charge capture template, according to FIG. 8A, FIG. 6A, FIG. 7F, FIG. 7G and FIG. 7H.
Figure 8B:
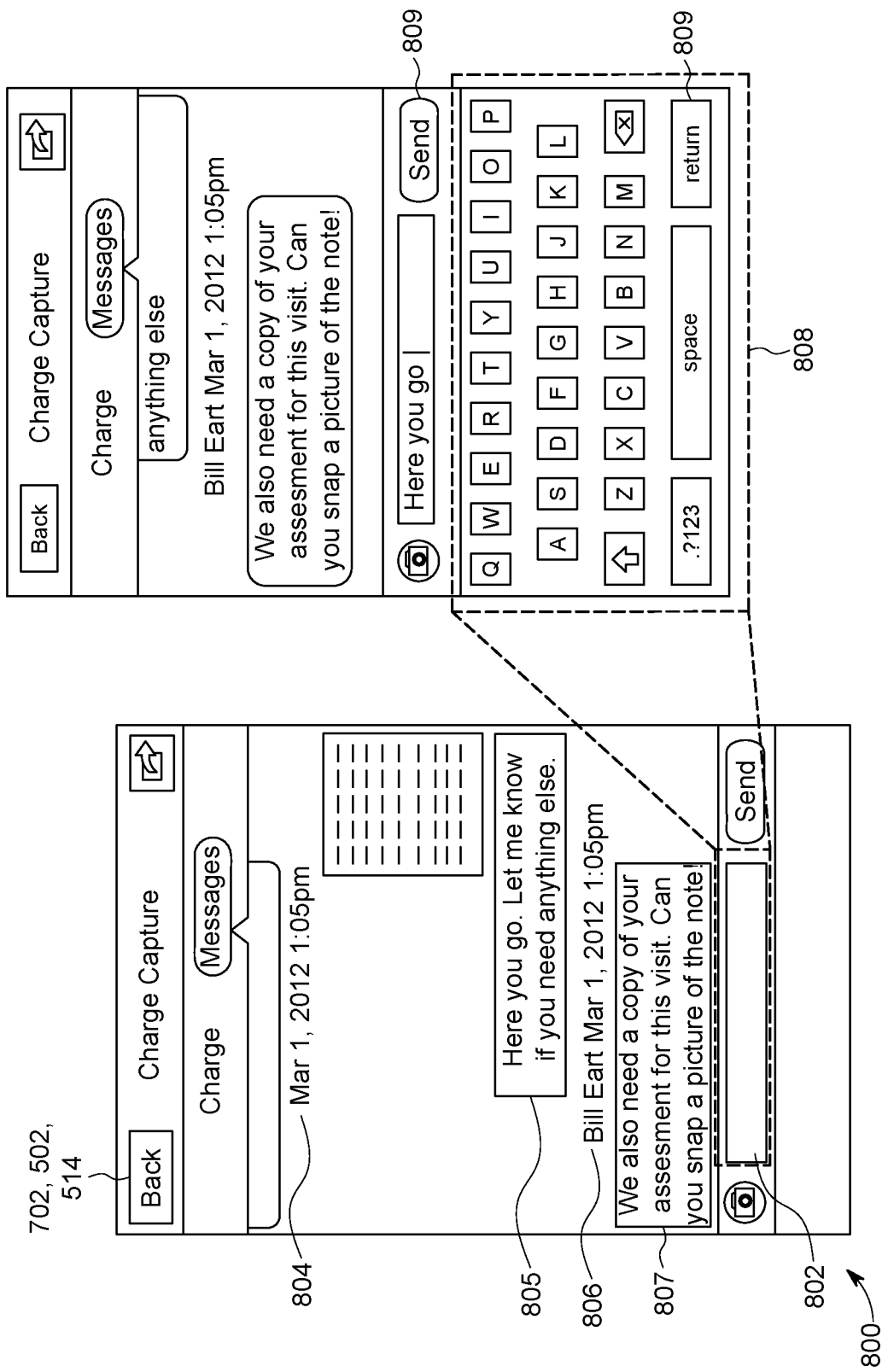
FIG. 8B is a screen shot view of an exemplary computer apparatus charge capture interface screen depicting the display of a selection of a recent existing charge created by the user of a charge capture template, toggled to the 'Messages' screen depicting all of the messages associated the charge that were sent/received in chronological order, with the latest message displayed at the bottom, according to FIG. 8A.
Figure 8C:
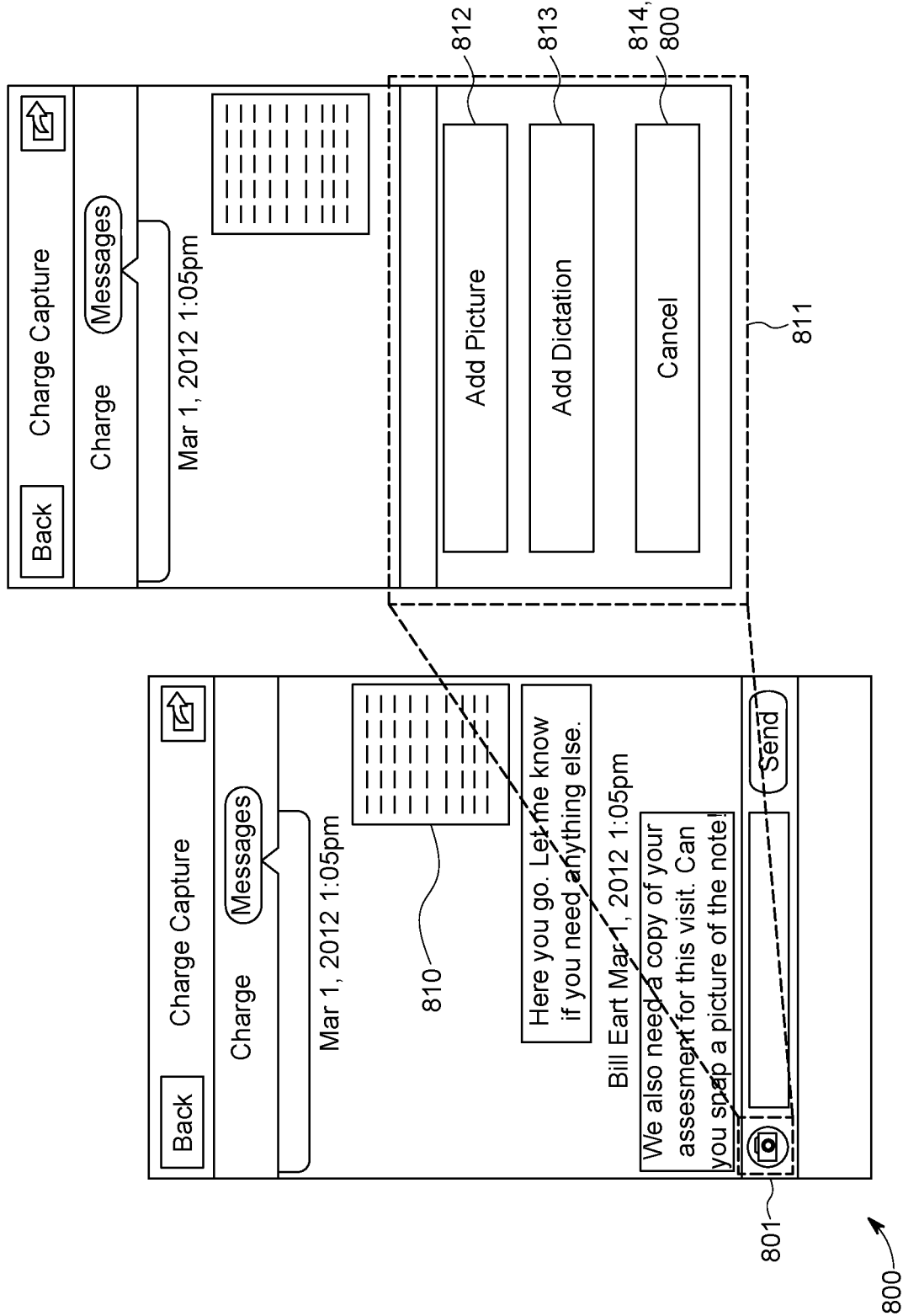
FIG. 8C is a screen shot view of an exemplary computer apparatus charge capture interface screen depicting the display of a selection of a recent existing charge created 'Messages' screen, according to FIG. 8A.
Figure 9A:
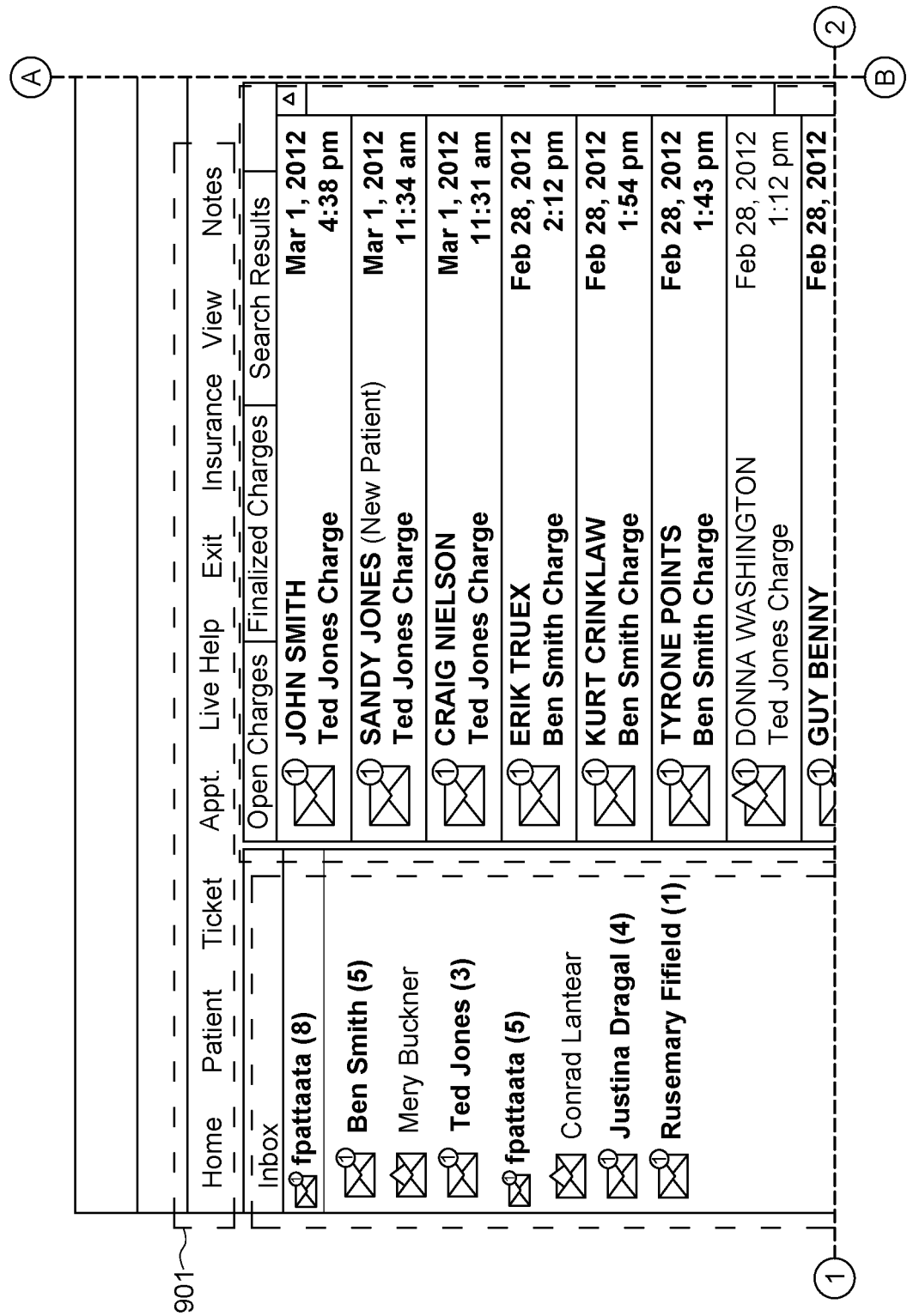
FIG. 9A is a screen shot view of an exemplary computer apparatus billing module interface screen depicting a charge capture billing template image with an Inbox-styled pane on the left, a tabbed Charges pane in the center, a tabbed Preview pane on the top right, and a Messages pane on the bottom right, according to an exemplary embodiment.
Figure 9A:
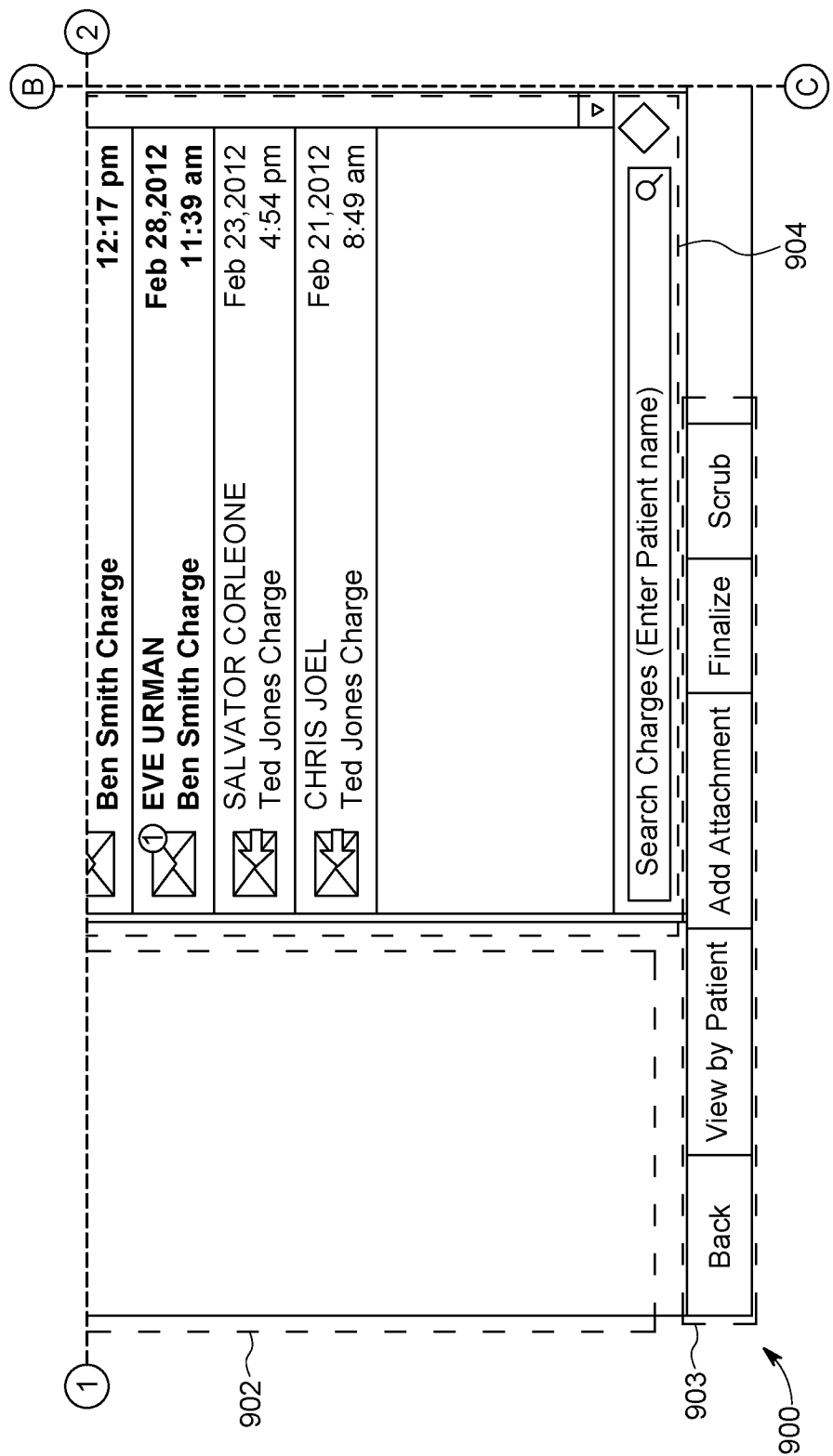

Referring now to FIGS. 1-20, by way of example, and not limitation, there is illustrated an example embodiment of system 100 for providing real-time bi-directional charge capture-centralized conversation between Billing and Provider entities, wherein system 100 comprises computer apparatus 101, charge-capture data 301, charge capture-centralized conversation data 305, and claim data 309. 2Computer apparatus 101 comprises secured network 106, first computer apparatus 102, second computer apparatus 108 and 109, and secure communication links 110, wherein first computer apparatus 102 comprises computer apparatus charge capture module 111, and second computer apparatuses 108 and 109 comprise computer apparatus billing module 112 (best shown in FIGS. 1, 5A, and 9A).

It will be recognized by those skilled in the art that secured network 106 may be a LAN, WAN, VPN, cloud, combination thereof or any network configuration of electronic devices. It will further be recognized that computer apparatus billing module 112 may comprise a single computer that comprises both integrated billing system 108 and computer apparatus billing module software 112 (best shown in FIG. 1) or alternatively may function on separate computers, non-integrated billing system 109 and computer apparatus billing module software 112 (also best shown in FIG. 1).

It will also be recognized by those skilled in the art that first computer apparatus 102 could comprise smart phones, tablets, personal digital assistants (PDAs), smart terminals, thin terminals, combination thereof or any network device that is capable of executing the commands in the computer apparatus charge capture module and is in electronic communication via local network or wide area network with the secure network 106. Additionally, while the term mobile device is used throughout, it is intended to be interchangeable with a computer apparatus that is running a charge capture module. Likewise, while desktop device is used throughout, it is intended to be interchangeable with a computer apparatus that is running a billing module.

It will further be recognized by those skilled in the art that the use of current healthcare coding standards (ICD9 and CPT) are used for exemplary purposes only and are in no way meant to limit the usability of the disclosure herein described in the event the healthcare industry coding standard advances (e.g. ICD10) The current standards and any future standards are intended to be interchangeably included in the current disclosure. Additionally, the present disclosure is not limited to healthcare, thus applicable codes from other industries that could benefit from the present disclosure are included within the intended scope.

Figure 2:
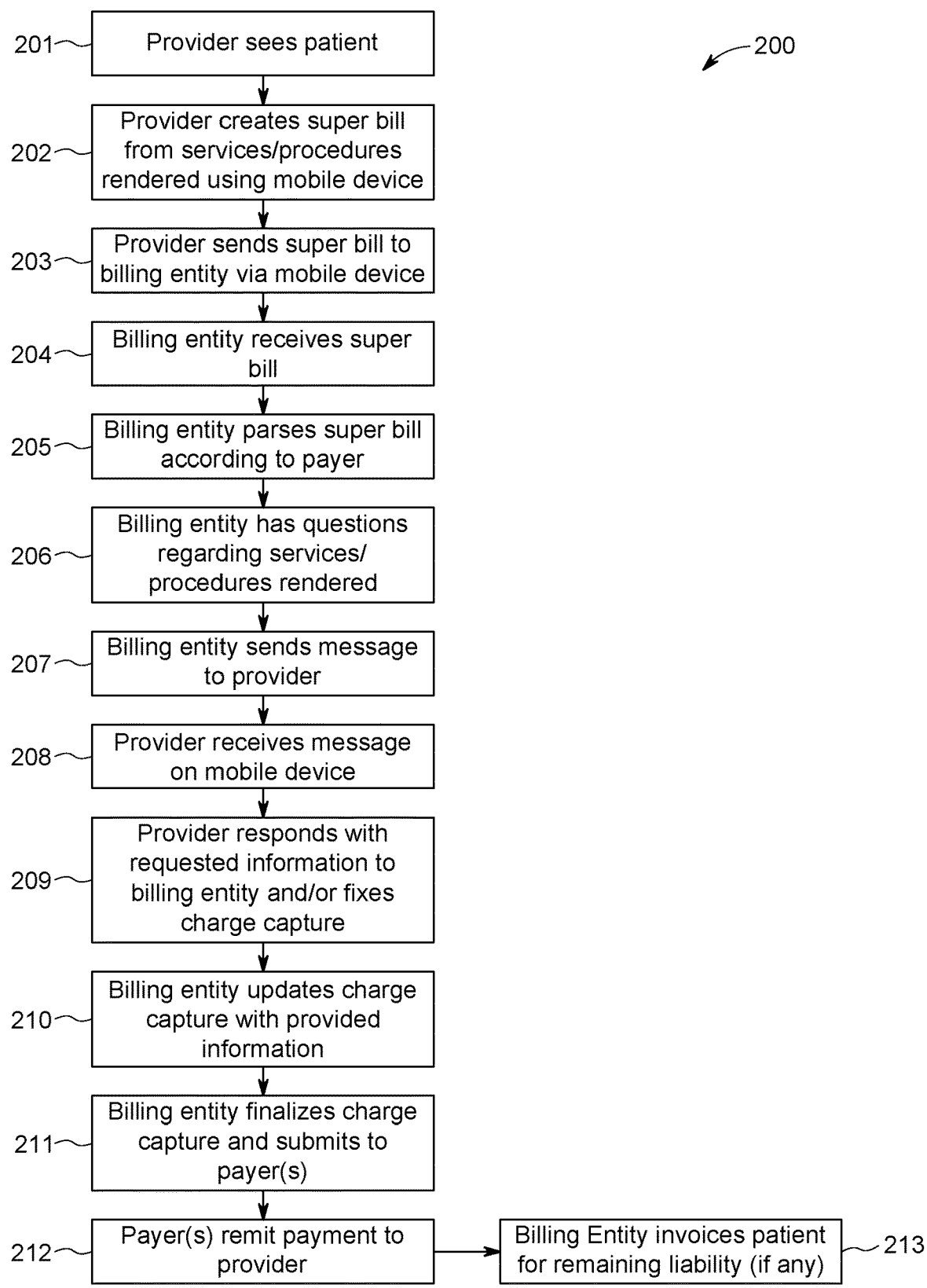
FIG. 2 is a flowchart depicting the general process between a Provider and Billing entity from service/product recipient encounter to payment remittance, via a preferred embodiment.
Figure 3:
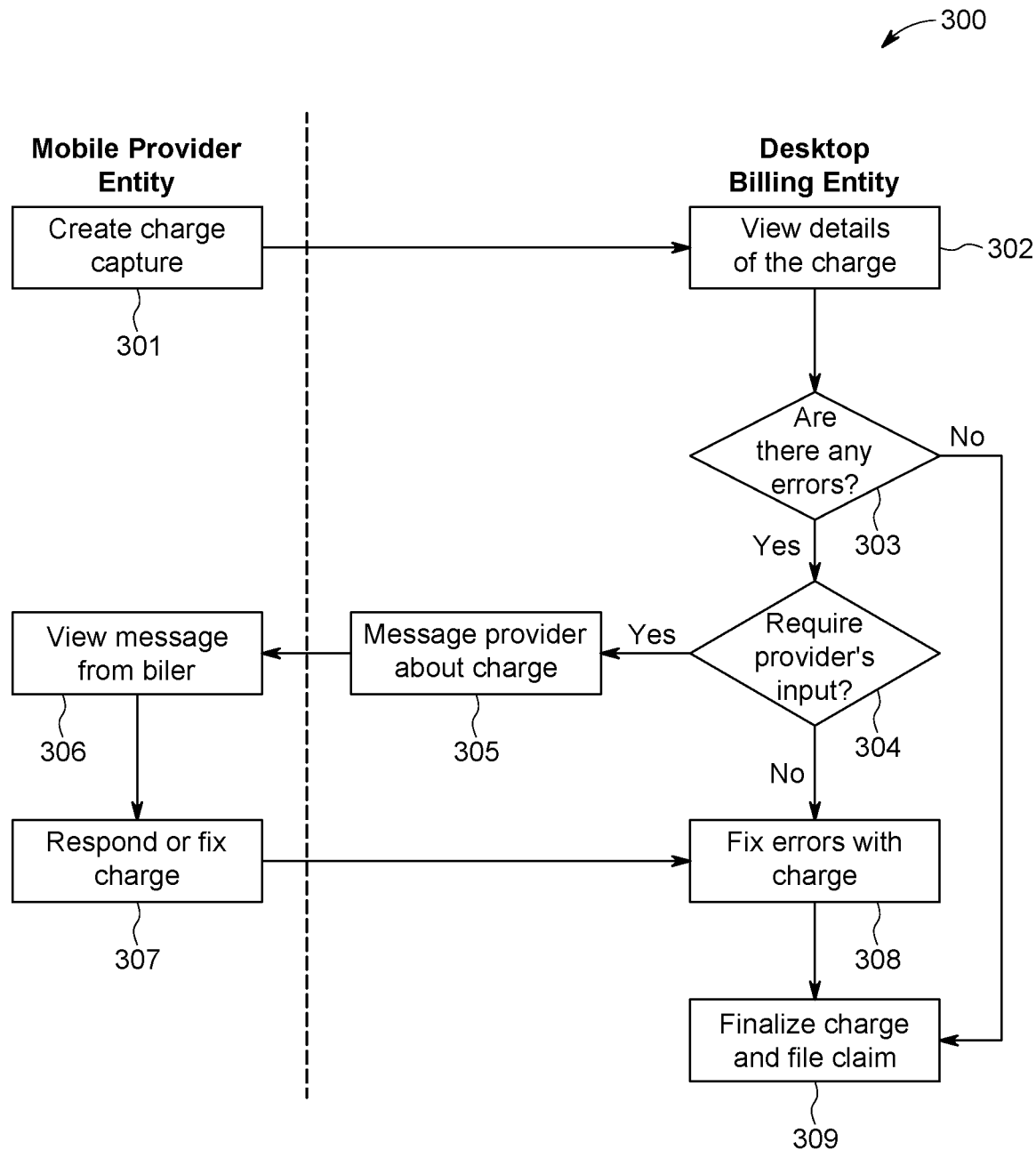
FIG. 3 is a simplified schematic of a preferred embodiment with an integrated billing system, showing both a computer apparatus charge capture module and a computer apparatus billing module participation by Provider and Billing entities.

Turning now to FIG. 2, 3, in use, in a preferred embodiment, a Provider begins session 200 at step 201, wherein the Provider sees a service/product recipient (service/product recipient used for non-limiting example purposes only) to perform an encounter using a first computer apparatus 102 with a computer apparatus charge capture module 112 on it to create a super bill from the services/procedures rendered during the encounter (202). In a preferred embodiment, as used herein super bill is synonymous with charge-capture data 301, and will be used interchangeably without any intended change in meaning. At step 203, the Provider then sends this super bill, in the form of charge-capture data 301 via the first computer apparatus 102 to the Billing entity 107 that is preferably using an integrated billing system 108 with computer apparatus module software 112. At step 204, the Billing entity 107 receives the super bill charge-capture data 301, views the details of the charge-capture data 301 (alternatively, step 302 in FIG. 3), then parses the super bill charge-capture data 301 by payer at step 205.

If the Billing entity has questions regarding the services/procedures documented by the Provider in the charge-capture data 301, at step 206 (alternatively, step 303 in FIG. 3) that require the Provider's input (step 304 in FIG. 3), then the Billing entity sends a message in real-time, known as charge capture-centralized conversation data 305 to the Provider at step 207. The Provider then receives the message 305 on his/her first computer apparatus 102 within the computer apparatus charge capture module 111 (alternatively, step 306 on FIG. 3). The Provider is able to use the computer apparatus charge capture module 111 on his/her first computer apparatus 102 to respond, in real-time to the message 305 at step 209 (alternatively, step 307 on FIG. 3) and provide the necessary information to the Billing entity 107 at step 210. The Billing entity 107 receives the message reply on its computer apparatus billing module software 112 on its integrated billing system 108, and uses the message contents 305 to update the charge capture data 301 at step 211 (alternatively, step 308 on FIG. 3).

At this point, the Billing entity can then finalize the parsed charge capture data 301 and submit the finalized form, known as claim data 309, to the proper payers (alternatively, step 309 on FIG. 3). At step 212, the payers receive the finalized claim data 309, and then remit the appropriate payment to the Provider. The Billing entity is then able to invoice the service/product recipient for any remaining liability for the services/procedures rendered during the encounter at step 213.

Turning now particularly to FIG. 4, in an alternate embodiment a Provider begins session 400 at step 401, wherein the Provider sees a service/product recipient (service/product recipient used for non-limiting example purposes only) to perform an encounter using a third party system or a paper file 103 to create a super bill from the services/procedures rendered during the encounter (402). At step 403, the Provider then sends this super bill, in a third party system's form or a paper file 103 to the Billing entity 107 that is preferably using an integrated billing system 108 with computer apparatus billing module software 112, or alternatively may be using a non- integrated billing system 109 with computer apparatus billing module software 112. At step 404, the Billing entity 107 receives the super bill (either in third party system form or paper file 103), views the details of the super bill, then enters the super bill into the computer apparatus billing module software 112 at step 405. At this point, because the super bill is entered into the computer apparatus billing module software 112, it now takes the form of charge capture data 301, as referenced above, and the Billing entity 107 parses the super bill charge-capture data 301 by payer at step 406.

If the Billing entity has questions regarding the services/procedures documented by the Provider in the charge-capture data 301, at step 407 that require the Provider's input, then the Billing entity sends a message in real-time, known as charge capture-centralized conversation data 305 to the Provider at step 408. The Provider then receives the message 305 on his/her first computer apparatus 102 within the computer apparatus charge capture module 111 (it is to be noted here that while a Provider does not have to use the first computer apparatus 102 with the computer apparatus charge capture module 111 to successfully create charge capture data 301, the security and functionality of the disclosure anticipate a first computer apparatus 102 with the computer apparatus charge capture module 111 to be used later in the process) at step 409. The Provider is able to use the computer apparatus charge capture module 111 on his/her first computer apparatus 102 to respond, in real-time to the message 305 at step 209 and provide the necessary information to the Billing entity 107 at step 410. The Billing entity 107 receives the message reply on its computer apparatus billing module software 112 on its integrated 108 or non-integrated billing system 109, and uses the message contents 305 to update the charge capture data 301 in the third party system (if used) at step 411. At step 412, the Billing entity 107 then also updates the charge capture data 301 on the computer apparatus billing module software 112.

At this point, the Billing entity can then finalize the parsed charge capture data 301 and submit the finalized form, known as claim data 309, to the proper payers. At step 413, the payers receive the finalized claim data 309, and then remit the appropriate payment to the Provider at step 414. The Billing entity is then able to invoice the service/product recipient for any remaining liability for the services/procedures rendered during the encounter at step 415.

Mobile Charge-Capture Module

Turning now more particularly to FIGS. 5A through 8C, the relationship between an exemplary computer apparatus charge capture module interface 500, displayed on a first computer apparatus 102 with a computer apparatus charge capture module 111 and charge capture data 301 is shown. FIG. 5A depicts a screen shot view of an exemplary computer apparatus charge capture module 111 interface screen 500 depicting a charge capture template image with an existing open charge-centered messages pane portion on top S03 and a recent existing charges created by the user pane portion on the bottom SO4. This interface enables the Provider to perform a search for an existing charge by service/product recipient (search for existing charge capture data 301), using the 'Search for an existing charge by service/product recipient' button 501, start a new charge capture (create new charge capture data 301), using the 'Start a new charge capture' button S02, open an existing charge capture- centralized conversation (message 30S) by selecting a message from S03, or open a recent existing charge the Provider created before (charge capture data 301) by selecting a charge from 504.

Figure 5B:
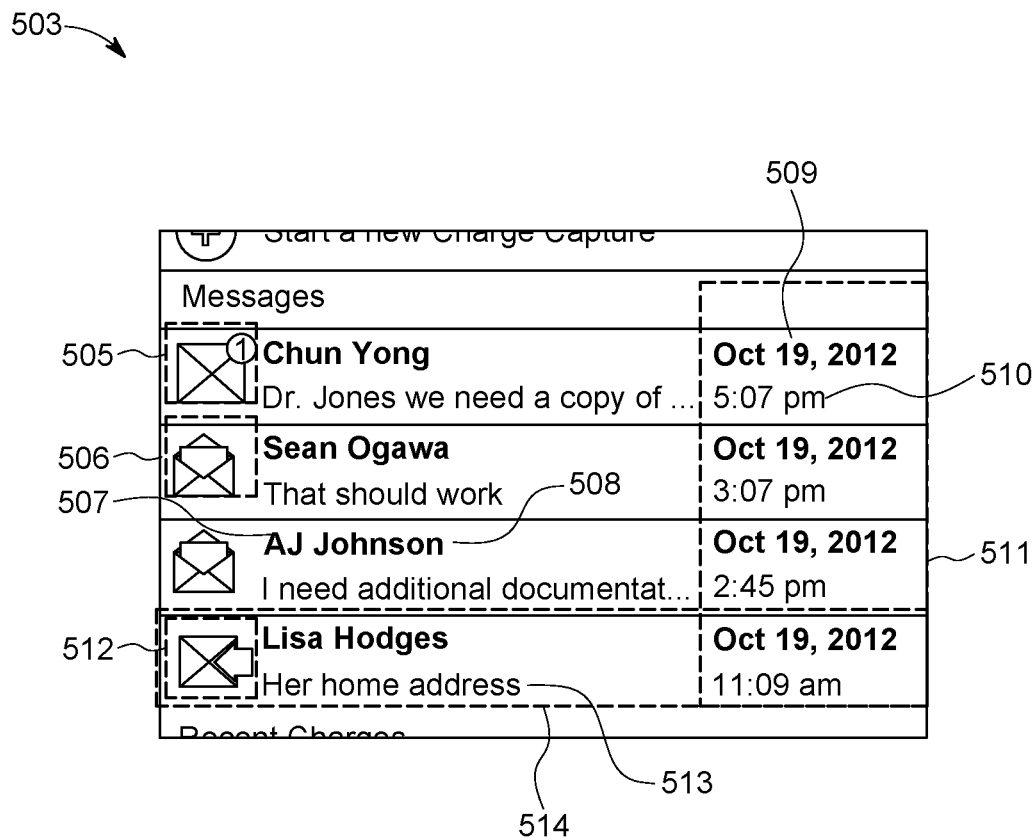
FIG. 5B is a screen shot view of an exemplary computer apparatus charge capture interface screen depicting the existing open charge-centered messages pane portion of a charge capture template, according to FIG. 5A.

Continuing with FIG. 5B, the open charge-centered messages pane portion S03 of FIG. 5A is expanded to better specify the types of information included in charge capture-centralized conversation message data 30S shown in 503. Here, a Provider will see a list of charge-capture centralized messages 514, listed in reverse chronological order 511, by time 509 and date 510 of the last message received. Included in the message data 305 is the service/product recipient's first 507 and last name 508. Also, a preview of the last message's content 513 is displayed. If the message is unread, or there are several unread messages, an icon to the left of the message will indicate this status 505 (along with the number of unread messages contained in the conversation). If the message is read, an icon to the left of the message will also indicate this status 506. Likewise, if a message is read and has been replied to, a third icon to the left of the message will indicate this status 512.

Figure 5C:
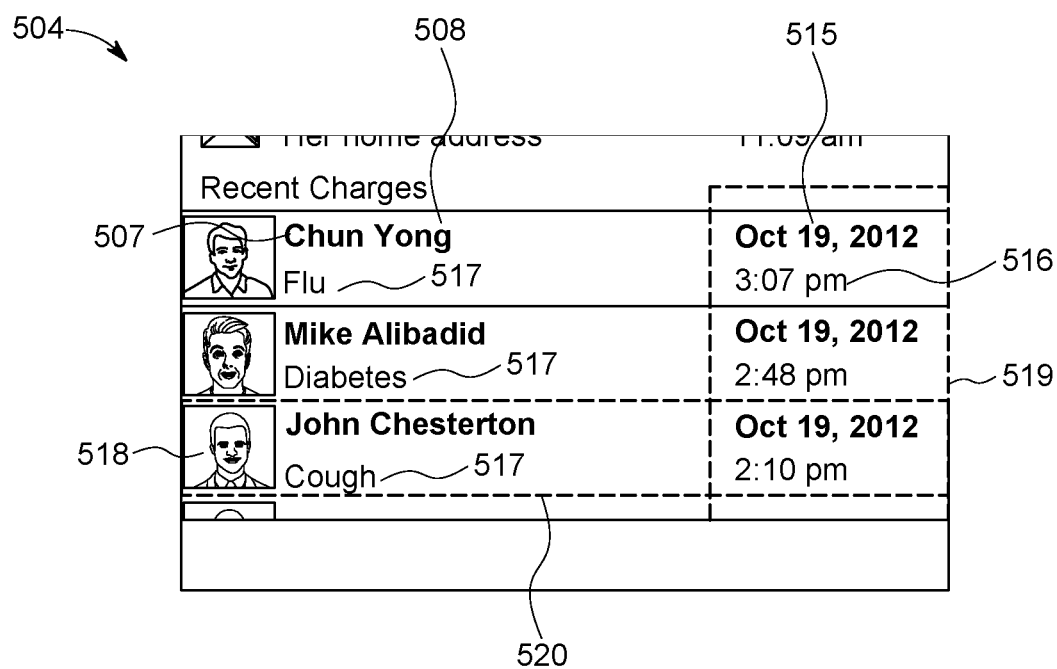
FIG. 5C is a screen shot view of an exemplary computer apparatus charge capture interface screen depicting the recent existing charges created by the user pane portion of a charge capture template, according to FIG. 5A.
Figure 5E:
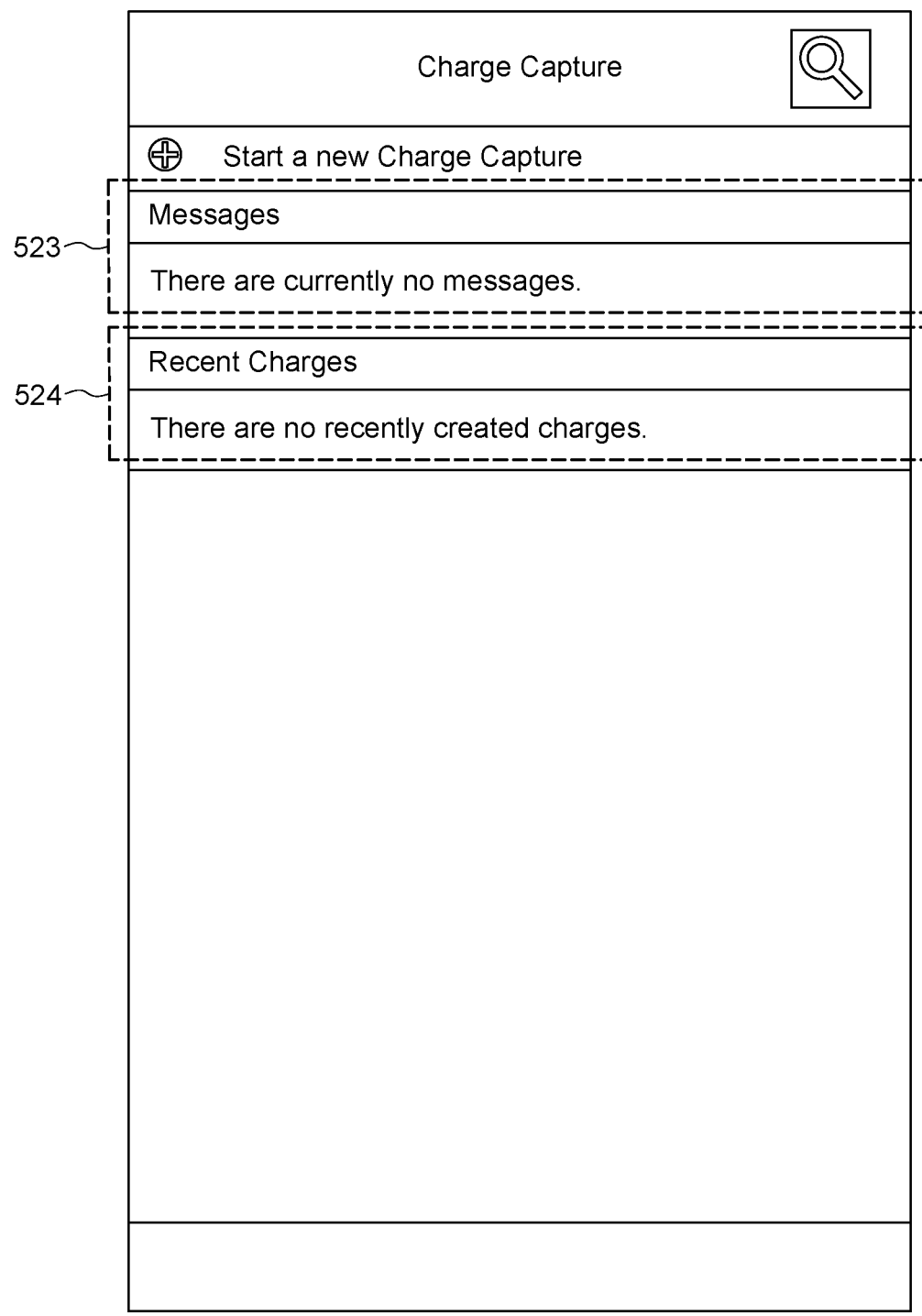
FIG. 5E is a screen shot view of an exemplary computer apparatus charge capture interface screen depicting a charge capture template image with an existing open charge-centered messages pane portion with no messages to display and a recent existing charges created by the user pane portion with no recent existing charges to display, according to FIG. 5A.

Similarly, in FIG. 5C the recent existing charges created by the user pane portion 504 of FIG. 5A is expanded to better specify the types of information included in charge capture data 301 shown in 504. Here, a Provider will see a list of charge-capture 520, listed in reverse chronological order 519, by time 516 and date 515 of the when the charge was created. Included in the charge data 301, besides the service/product recipient's first 507 and last name 508, is the description of the first diagnosis listed in the charge 517 as well as a thumbnail of the service/product recipient's photo 518.

A further expansion of FIG. 5B and 5C's S04 is shown in FIG. 5D, where a listing of ten (10) open charges S21 are displayed, with the option to display ten (10) more open charges via the 'more' button S22. Likewise, in FIG. 5E according to the original display in FIG. 5A, the screen shows an exception message (error) when there are no existing open charge-centered messages S23 or recent existing charges created by the user S24 to display.

Figure 6A:
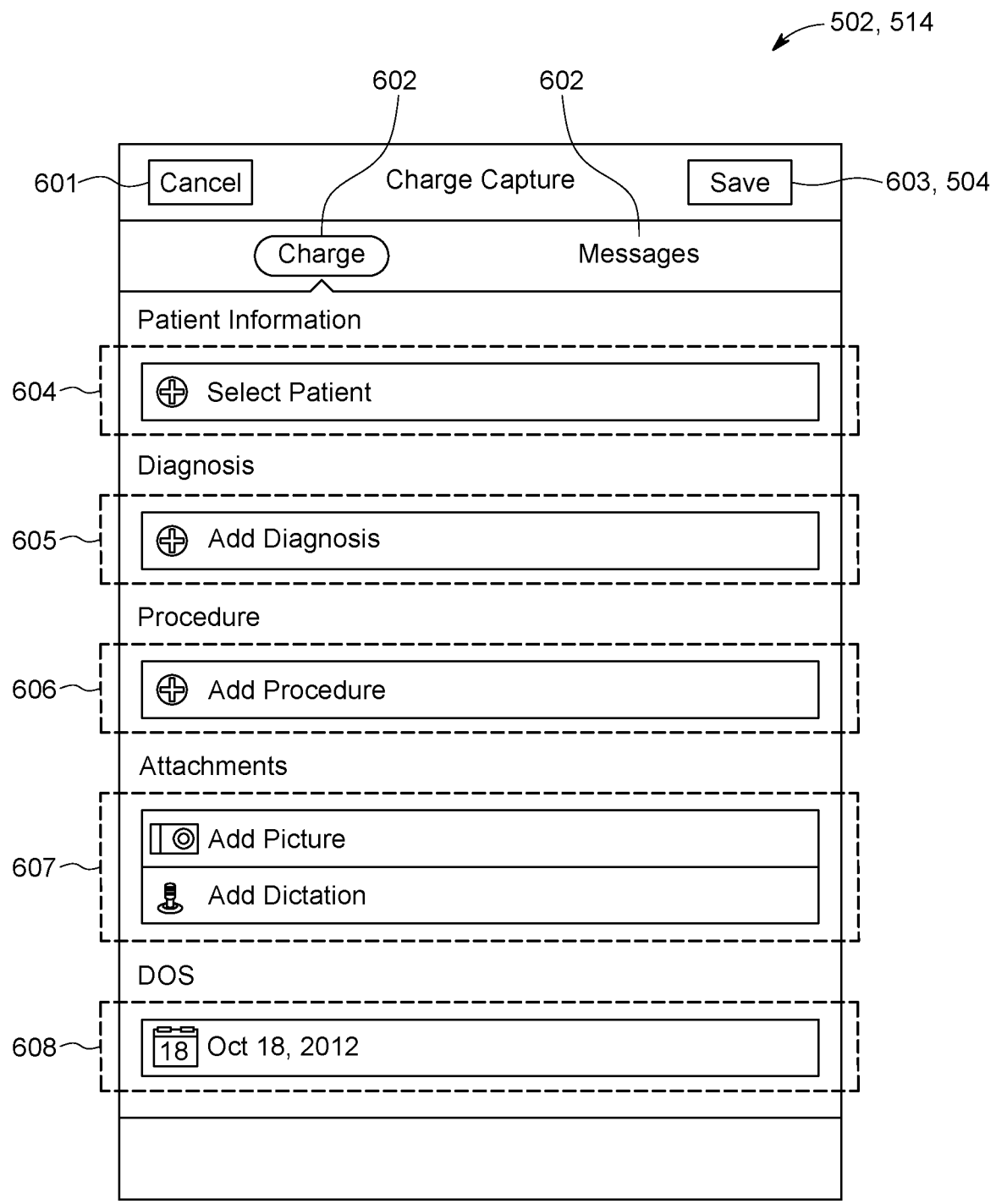
FIG. 6A is a screen shot view of an exemplary computer apparatus charge capture interface screen depicting a sub-template of a charge capture template image for starting a new charge capture, according to FIG. 5A.
Figure 6B:
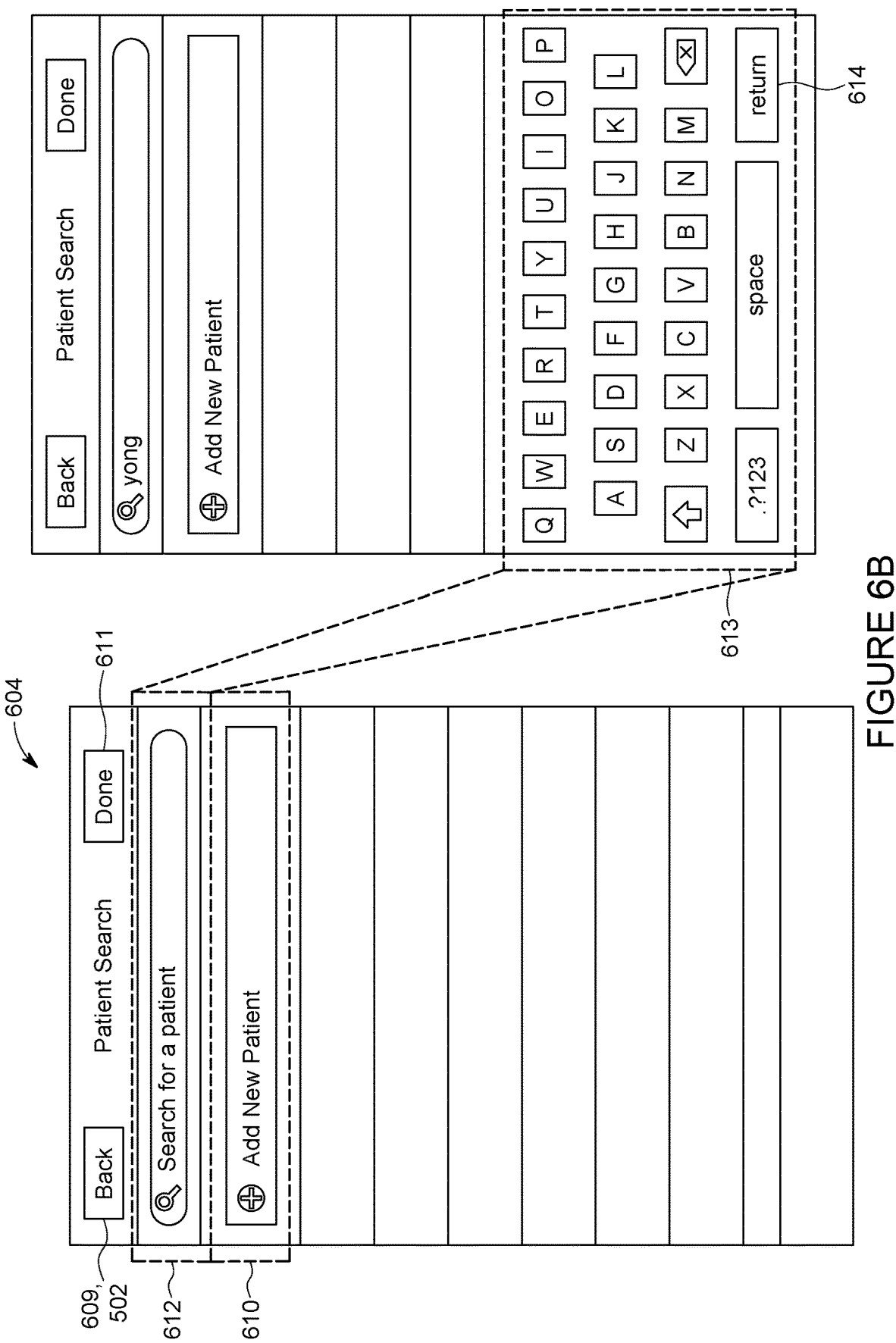
FIG. 6B is a screen shot view of an exemplary computer apparatus charge capture interface screen depicting a sub-template of a charge capture template image for selecting a service/product recipient, according to FIG. 6A.

Turning now to FIG. 6A, which depicts a sub-template image of the computer apparatus charge capture template image interface in FIGS. 5A through 5E, where a Provider can start a new charge capture (create new charge capture data 301) according to the 'Start a new charge capture' button S02 in FIG. 5A. Hitting the 'Cancel' button 601 will return the Provider to FIG. 5A whereas selecting the 'Select Service/product recipient' bar 604 will enable the Provider to begin populating charge capture data 301 with critical pieces of service/product recipient encounter information (e.g. service/product recipient information, service/product recipient diagnosis information, service/product recipient procedure information, service/product recipient file attachments and service/product recipient's date of service), the first of which is the service/product recipient selection information. By selecting the 'Select Service/product recipient' bar 604, the Provider is taken to a further sub-template image shown in FIG. 6B. Again, the Provider can opt to return to the previous sub-template by hitting the 'Back' button 609, or the Provider can decide whether to search for an existing service/product recipient using the 'Search for a service/product recipient' bar 612 or add a new service/product recipient by selecting the 'Add New Service/product recipient' bar 610.

Figure 6C:
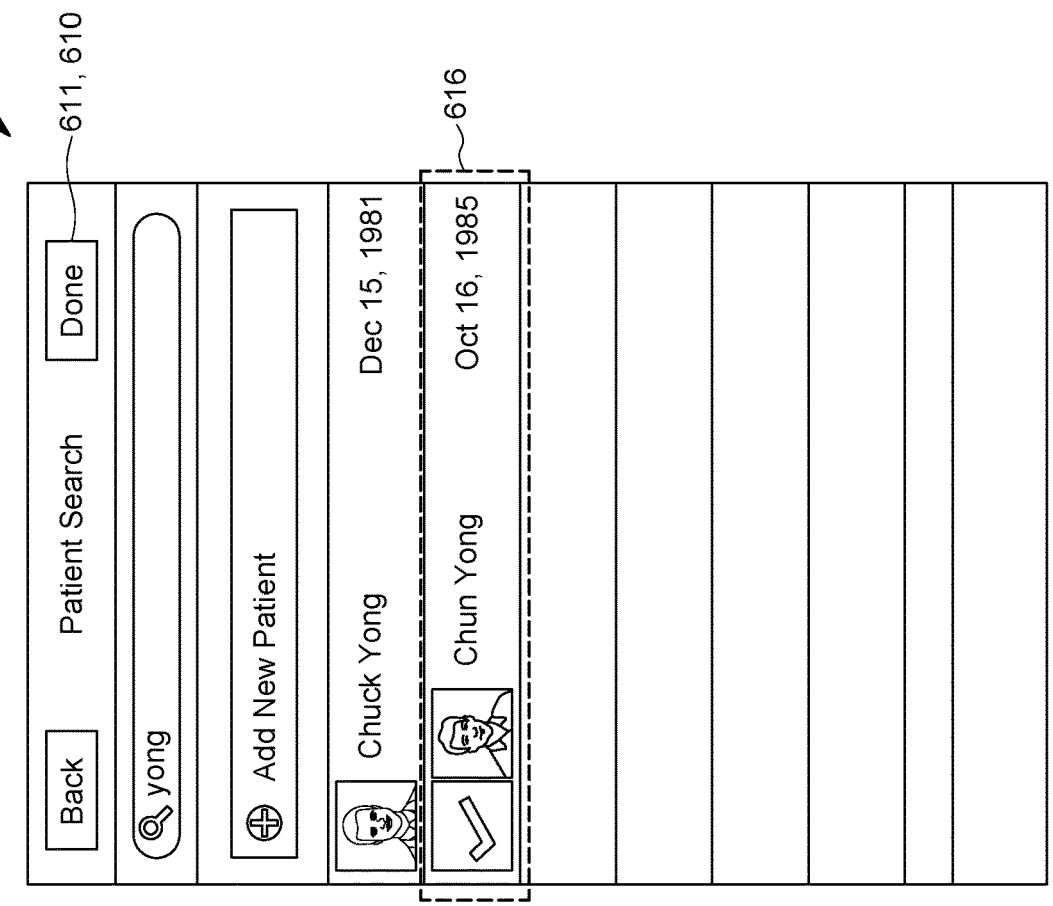
FIG. 6C is a screen shot view of an exemplary computer apparatus charge capture interface screen depicting a sub-template of a charge capture template image for selecting a service/product recipient (from results of a search performed by service/product recipient last name, according to FIG. 6B), according to FIG. 6C.
Figure 6C:
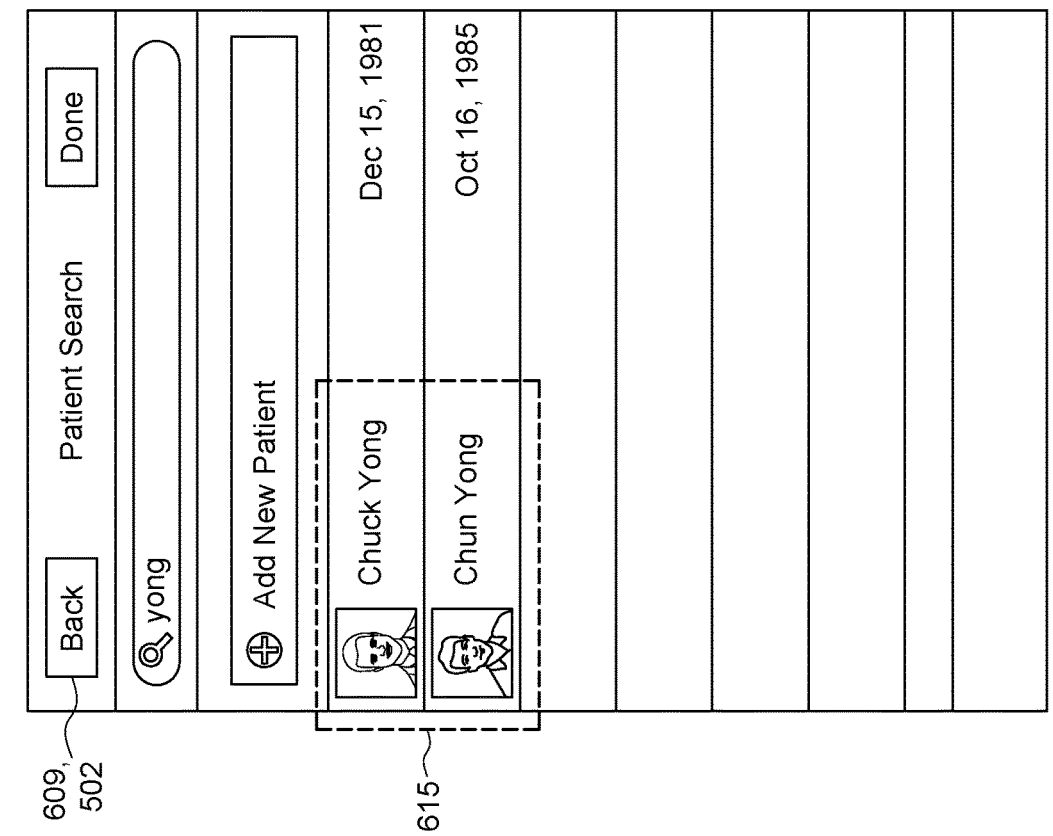
Figure 6D:
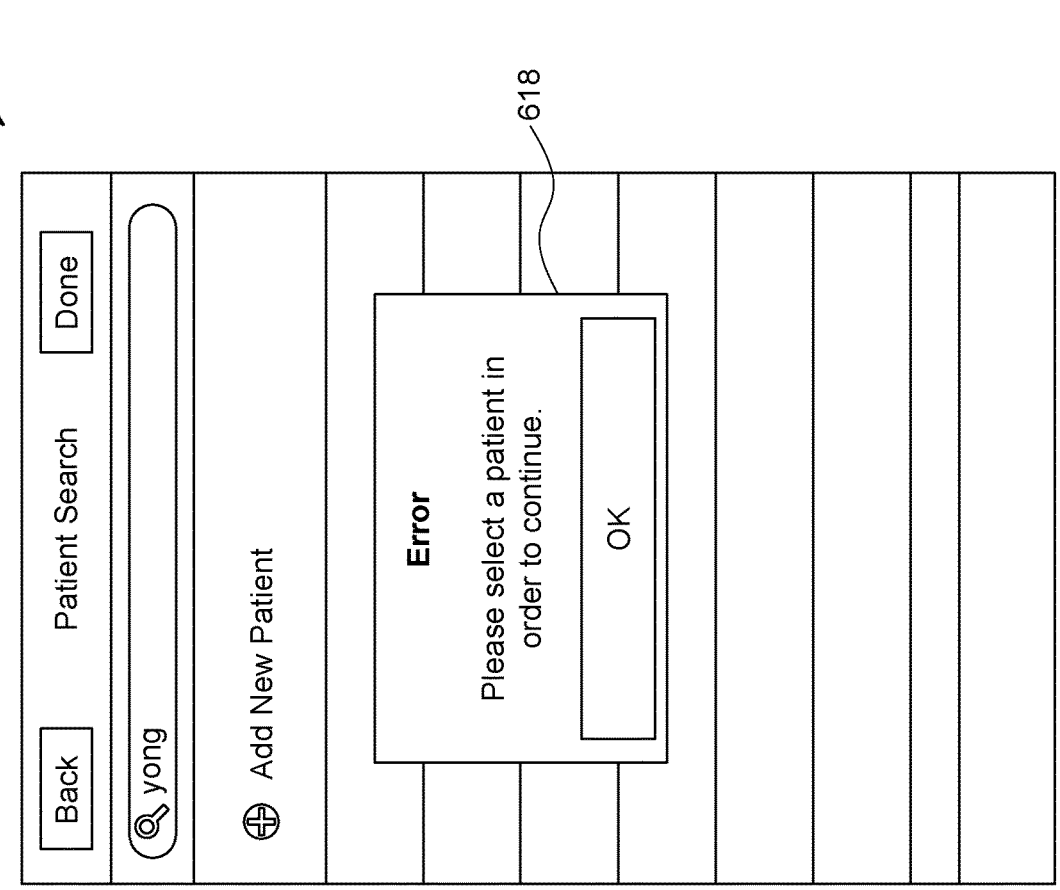
FIG. 6D is a screen shot view of an exemplary computer apparatus charge capture interface screen depicting a sub-template of a charge capture template image for selecting a service/product recipient (from results of a search performed by service/product recipient last name, according to FIG. 6B) with error messages, according to FIG. 6C.
Figure 6D:
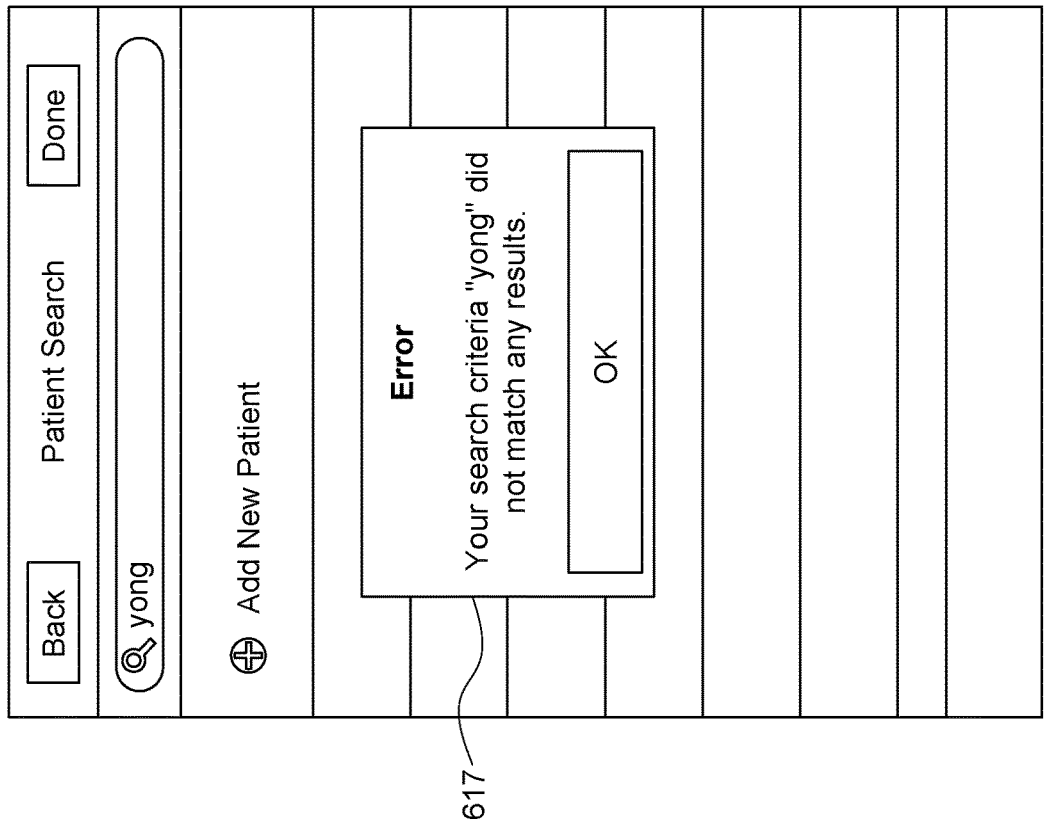
Figure 6F:
FIG. 6F is a screen shot view of an exemplary computer apparatus charge capture interface screen depicting a fully populated sub-template of a charge capture template image for adding a new service/product recipient, according to FIG. 6A and FIG. 6E.
Figure 6H:
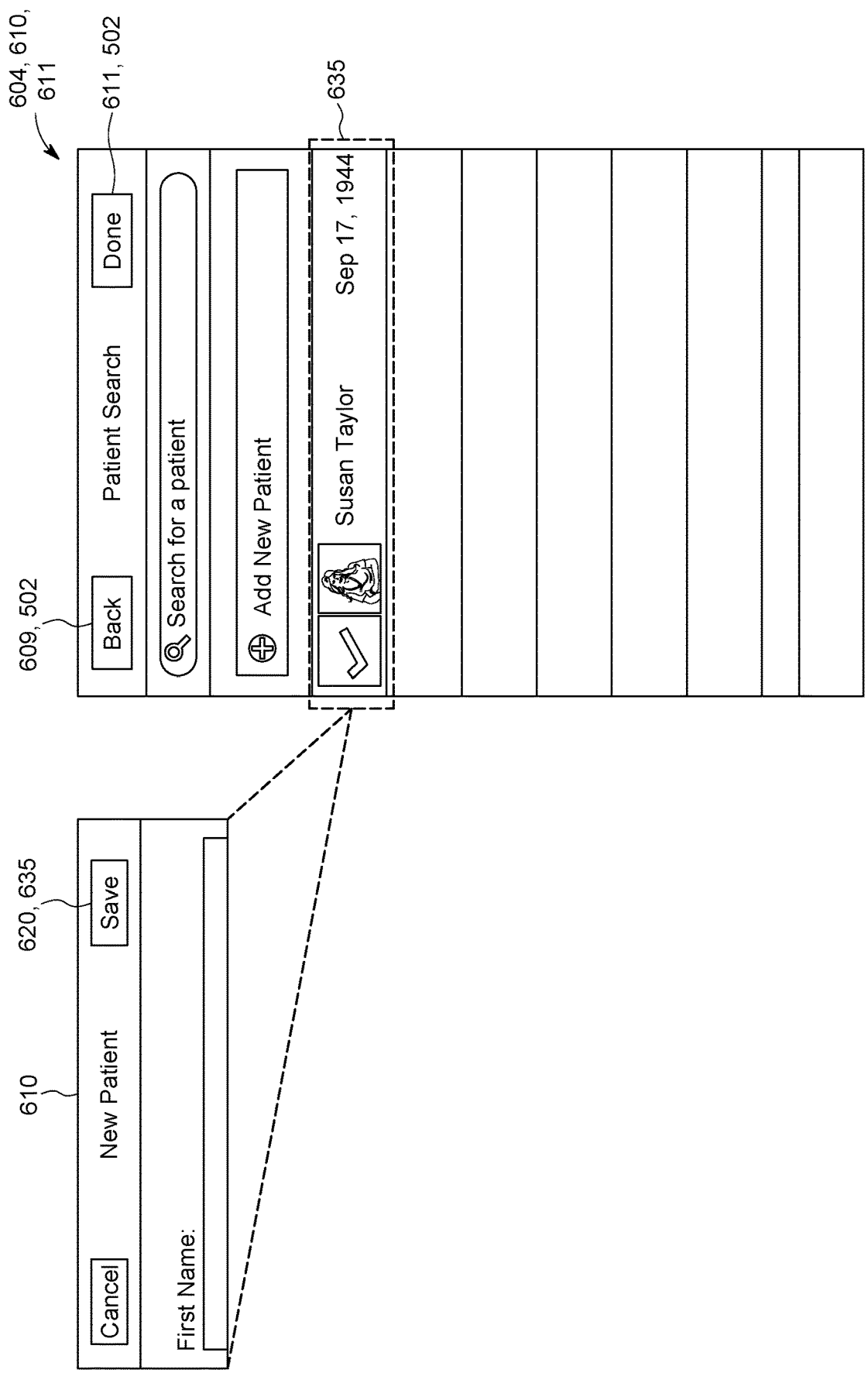
FIG. 6H is a screen shot view of an exemplary computer apparatus charge capture interface screen depicting a sub-template of a charge capture template image for selecting a service/product recipient, according to FIG. 6A, showing newly created service/product recipient in list, according to FIG. 6B.
Figure 7A:
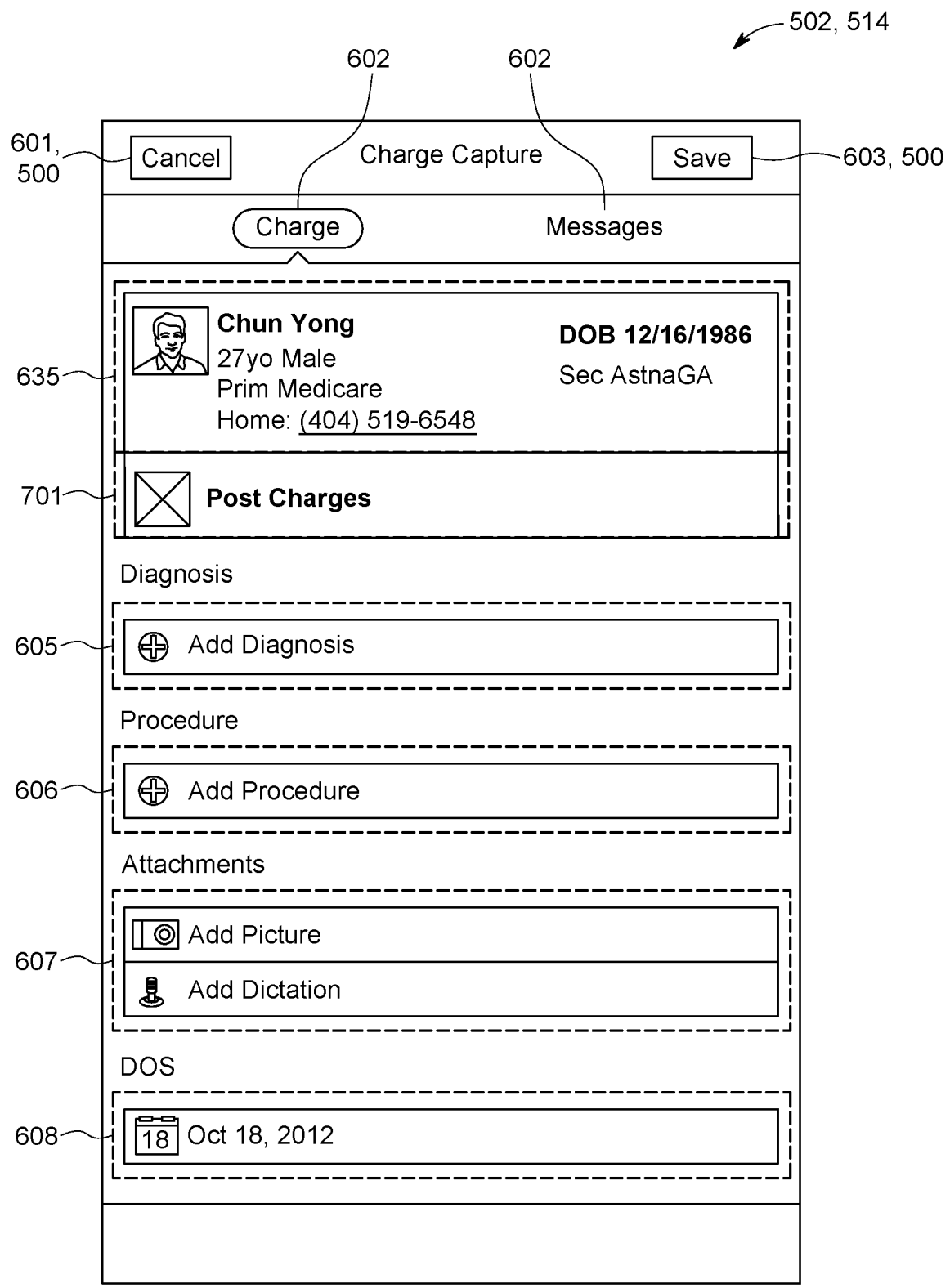
FIG. 7A is a screen shot view of an exemplary computer apparatus charge capture interface screen depicting a sub-template of a charge capture template image for starting a new charge capture, according to FIG. 5A, showing newly created service/product recipient populated in 'Select Service/product recipient' bar.

If the Provider selects the 'Search for a service/product recipient' bar 612, the first computer apparatus' keyboard 613 will be displayed, enabling the Provider to search for a service/product recipient by typing in the service/product recipient's last name. The return button 614 on the first computer apparatus' keyboard, when displayed, initiates the search based on the last name criteria the Provider has entered, populating the results of the search 615 on the screen, as shown in FIG. 6C. Here, the Provider can select the desired service/product recipient 616 and will be returned to 'Start New Charge Capture' sub-template with the desired service/product recipient's information populated in the service/product recipient section of the template 635 as shown in FIG. 7A (e.g. service/product recipient first name, service/product recipient last name, service/product recipient date of birth, service/product recipient gender, service/product recipient phone number, service/product recipient photo and other relevant service/product recipient file attachments). If the Provider's search does not yield any results, FIG. 6D displays the exception message 617 (error) that will occur. Also, if the Provider does not select a service/product recipient or the search otherwise yields no results from which to select, by hitting the 'Done' button 611, a separate exception message 618 (error) is displayed, also shown in FIG. 6D.

Alternatively, if the Provider selects the 'Add New Service/product recipient' bar 610, the Provider is taken to a further sub-template image shown in FIG. 6E. Again, the Provider can opt to return to the previous sub-template by hitting the 'Cancel' button 619, or the Provider can begin populating the service/product recipient information: first name 621, last name 622, date of birth 623, gender 624, and phone number 625. If the Provider attempts to save the new service/product recipient by hitting the 'Save' button 620 before entering all of the critical pieces of information just listed, an exception message will display 633. Also, if the Provider attempts to add a new service/product recipient whose critical pieces of information match an existing service/product recipient, and then tries to save this service/product recipient by hitting the 'Save' button 620, an exception message will display 634, confirming the Provider does indeed want to create the new service/product recipient.

Continuing with FIG. 6E, the Provider can also add a photo of the service/product recipient 626 (via the first computer apparatus' peripheral device) that becomes the thumbnail picture shown in FIGS. 5A and 5C, as well as other pictures 627 and/or dictations 628 (shown in FIG. 6F, service/product recipient photo 630, added picture of a service/product recipient face sheet 631, and an added dictation 632) (the attachment feature is intended to allow the Provider to add any and all relevant service/product recipient file attachments) To save the new service/product recipient, the Provider hits the 'Save' button 620, and is returned to 'Service/product recipient Search' sub-template with the newly added service/product recipient now showing up selected in the list 635, as shown in FIG. 6I1. From here, the Provider hits the 'Done' button 611, and is returned back to the 'Start New Charge Capture' sub-template with the newly added service/product recipient's information populated in the service/product recipient section of the template 635, shown in FIG. 7A.

Turning now to the next step in creating a new charge capture (new charge capture data 301)' once a service/product recipient has been added or selected, according to FIG. 7A, the Provider is able to search past charges of the new or existing selected service/product recipient by clicking on the 'Past Charges' bar 701 (if any exist). This 'Past Charges' bar opens up a further sub-template shown in FIG. 7B, which gives the Provider the ability to select a past charge 704 and then choose the 'Action' button 707 to copy 709 or edit 710 the charge(according to FIG. 7C)

Figure 7B:
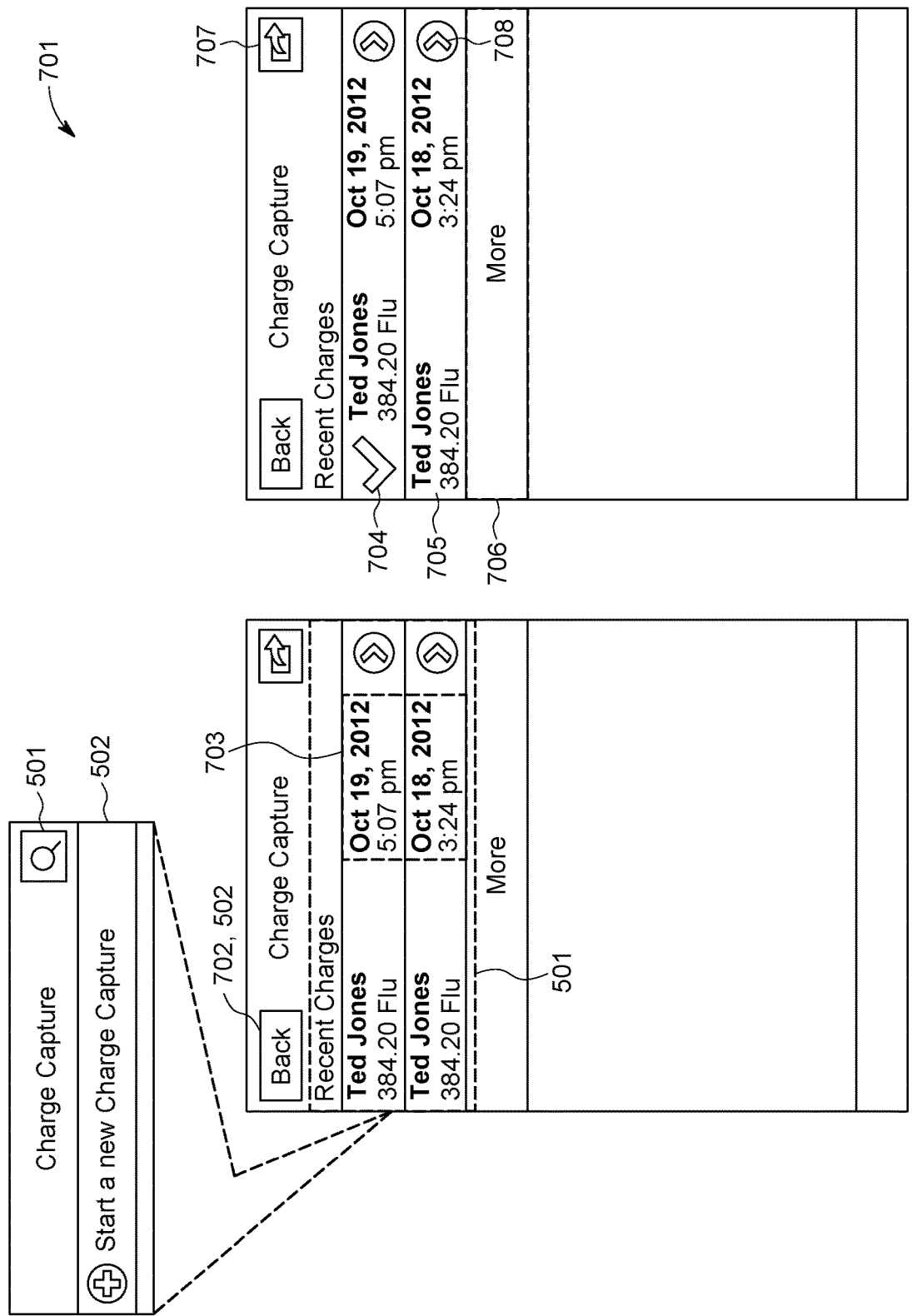
FIG. 7B is a screen shot view of an exemplary computer apparatus charge capture interface screen depicting a sub-template of a charge capture template image for viewing and allowing selection of past charges associated with the selected service/product recipient, according to FIG. 7A.
Figure 7C:
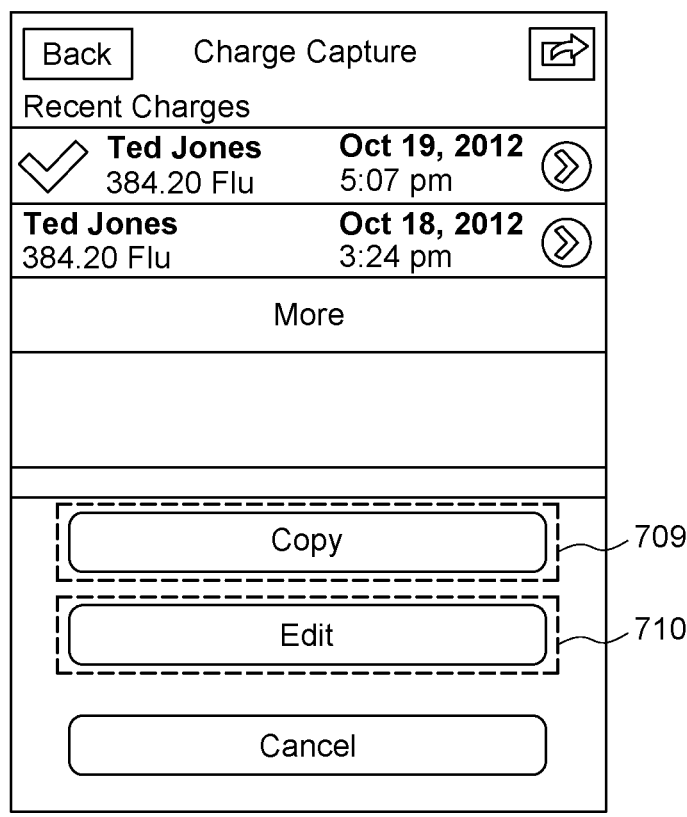
FIG. 7C is a screenshot view of an exemplary computer apparatus charge capture interface screen depicting a sub-template of a charge capture template image for viewing and allowing selection of past charges associated with the selected service/product recipient, shown in mode when 'Action' button has been selected, according to FIG. 7B.

Continuing on FIG. 7B, the list of past charges displayed 501 is the same list displayed when using the 'Search for an existing charge by service/product recipient' option in FIG. 5A, ordered in reverse chronological order by time stamp 703 of past charges created for the service/product recipient within the last seven (7) days. In addition, each past charge will have the primary diagnosis (here, an ICD9 code) and description 705 listed. Here a Provider can opt to return to the prior screen by clicking the 'Back' button 702, or, as mentioned, a past charge can be selected 704. By choosing the button 708 to the right of each charge, the details of the charge are displayed in a further sub-template screen as shown by 514 in FIG. 5A. The Provider can also choose to display ten (10) more recent charges for the service/product recipient by clicking the 'More' button 706. If a past charge is selected 704, that past charge's details then populate the remainder of the empty boxes in the new charge capture template, similar to FIG. 7J. Otherwise, the Provider continues populating the new charge capture template (creating new charge capture data 301).

Figure 7D:
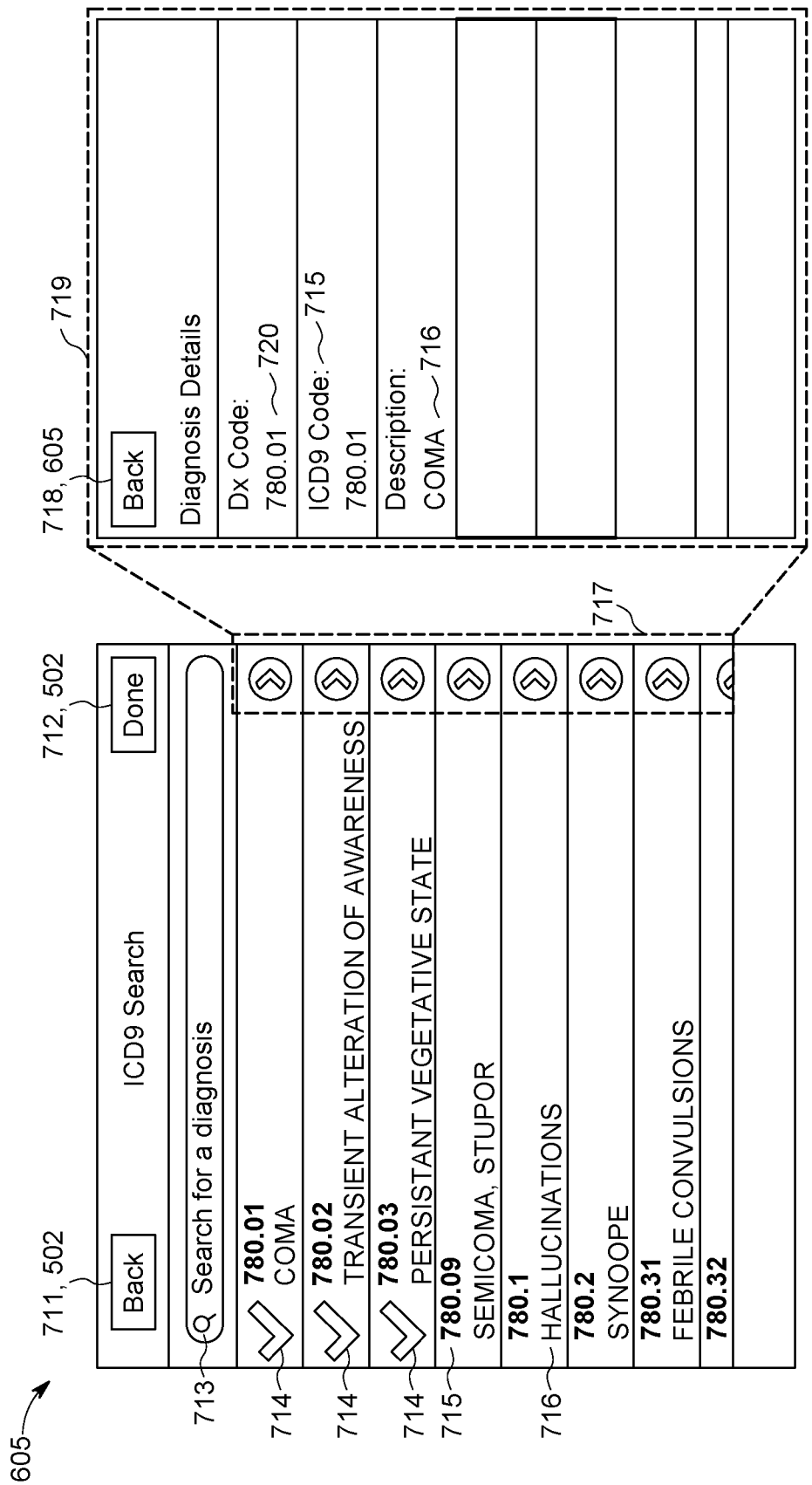
FIG. 7D is a screen shot view of an exemplary computer apparatus charge capture interface screen depicting a sub-template of a charge capture template image for adding a diagnosis per the 'Add Diagnosis' bar, according to FIG. 5A and FIG. 6A.
Figure 7E:
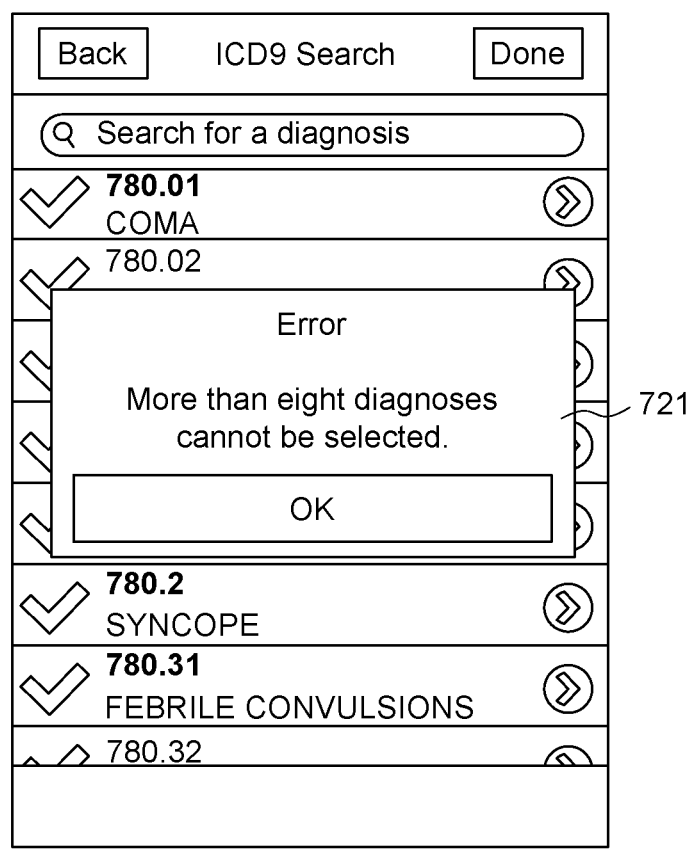
FIG. 7E is a screen shot view of an exemplary computer apparatus charge capture interface screen depicting a sub-template of a charge capture template image for adding a diagnosis per the 'Add Diagnosis' bar with an error message, according to FIG. 5A and FIG. 6A.
Figure 7F:
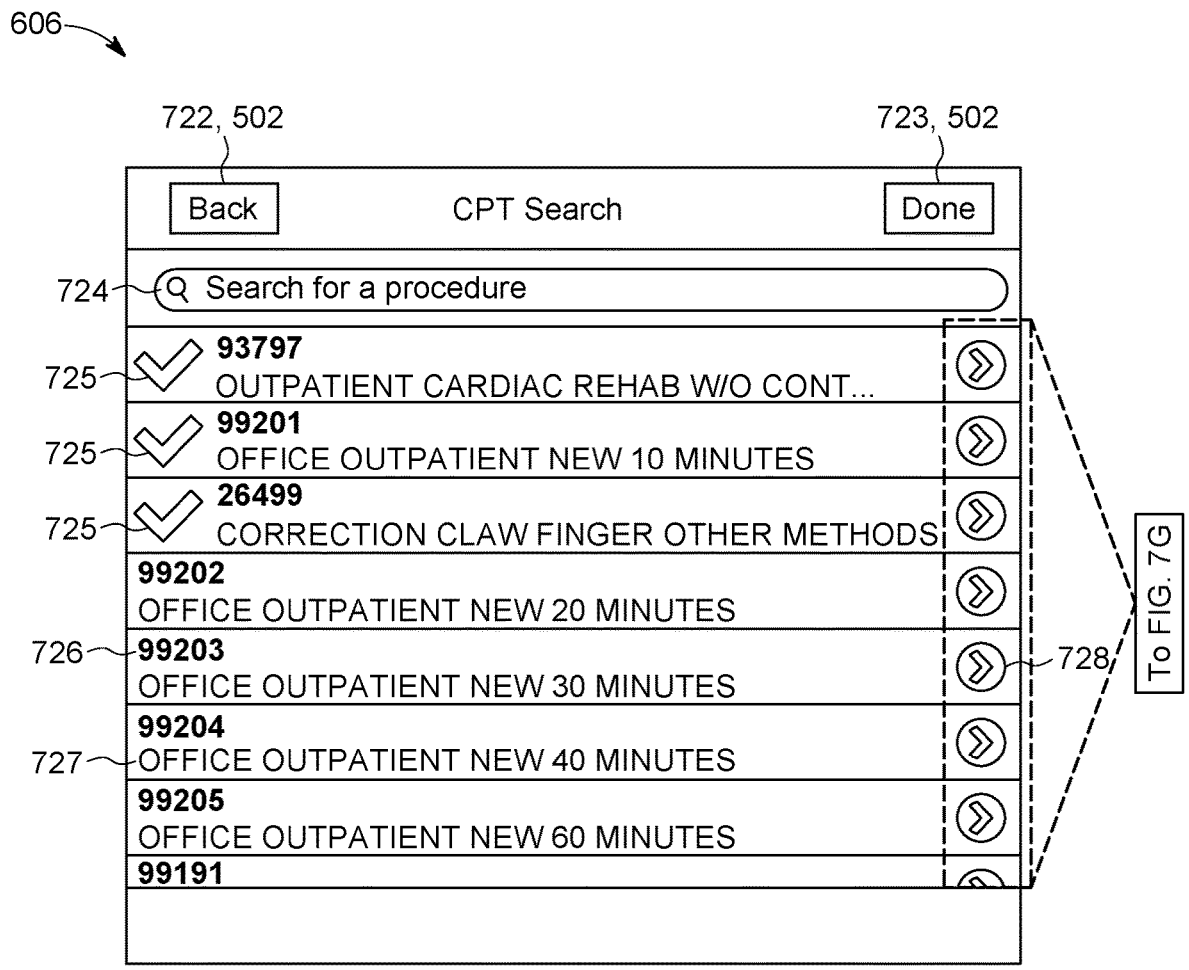
FIG. 7F is a screen shot view of an exemplary computer apparatus charge capture interface screen depicting a sub-template of a charge capture template image for adding a procedure per the 'Add Procedure' bar, according to FIG. 5A and FIG. 6A.

In the absence of a past charge selection, the Provider is able to add a diagnosis by clicking the 'Add Diagnosis' bar 605, where the Provider is taken to a further sub-template image shown in FIG. 7D. The Provider can opt to return to the previous sub-template by hitting the 'Back' button 711, or the Provider can begin searching for diagnoses to add to the charge capture. By clicking in the 'Search for a diagnosis' bar 713, the Provider can perform an incremental search for a diagnosis, which will search on both the diagnosis and any applicable code (here, the ICD9 code), displaying the results on the screen with the code shown first (again, here it is the ICD9 code) 715 and the diagnosis description second 716, for each diagnosis. From this list, the Provider is able to select a plurality of diagnoses 714 (for exemplary purposes, this number can be modified based on application, an exemplary exception message showing a modification limitation of up to eight (8) diagnoses 721 is show in FIG. 7E).

If a Provider would like to expand an individual diagnosis, clicking on the button to the right of each diagnosis 717 will take the Provider to a further 'Diagnosis Details' sub-template also shown in FIG. 7. The Provider can return to the diagnosis selection screen by hitting the 'Back' button 718 on the 'Diagnosis Details' screen 719. The 'Diagnosis Details' screen 719 displays expanded diagnosis information, including both the code (here, an ICD9 code) 715 and the diagnosis description 716 in addition to the Diagnosis Code 720. Once the Provider has completed selecting diagnoses, hitting the 'Done' button 712 returns the Provider to the new charge capture screen, similar to FIG. 7J, with the diagnosis selection 605 now populated 714.

According to FIG. 7A, the next critical piece of information to creating a new charge capture (creating new charge capture data 301) is to add a Procedure by selecting the 'Add Procedure' button 606. Once clicked, the 'Add Procedure button 606 opens a further sub-template shown in FIG. 7F, similar to adding a diagnosis. Once in the sub-template, the Provider can opt to return to the previous screen by clicking the 'Back' button 722 or the Provider can search for a procedure by clicking on the 'Search for a procedure' bar 724 that allows the Provider to perform an incremental search for a procedure, which searches on the procedure description and an application code (here, the CPT code), displaying the results on the screen with the code first (again, here the CPT code) 726 and the procedure description second 727, for each procedure. From this list, the Provider is able to select multiple procedures 725.

Figure 7G:
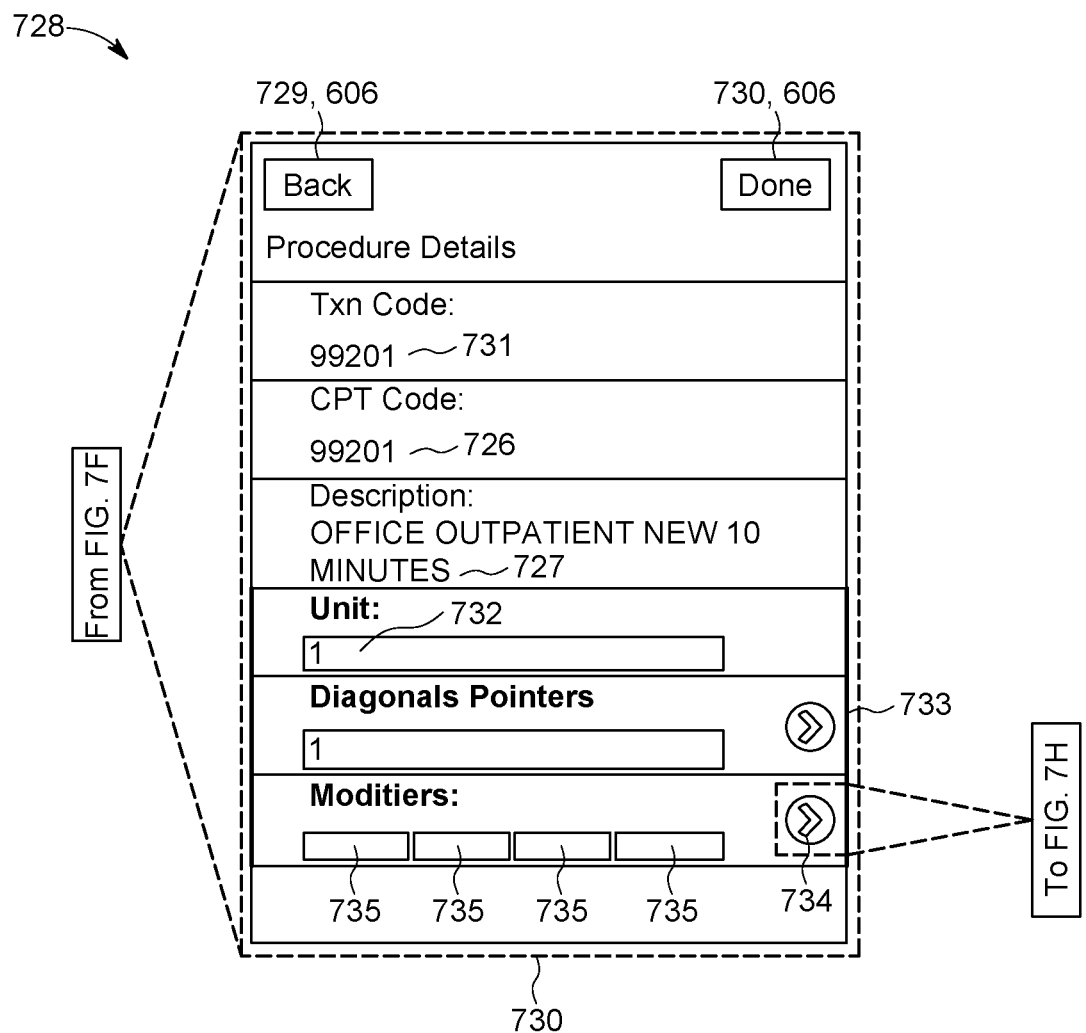
FIG. 7G is a screen shot view of an exemplary computer apparatus charge capture interface screen depicting a sub-template of a charge capture template image for adding a procedure per the 'Add Procedure' bar, according to FIG. 5A, FIG. 6A and FIG. 7F.

If a Provider would like to expand an individual procedure, clicking on the button to the right of each procedure 728 will take the Provider to a further 'Procedure Details' sub-template also shown in FIG. 7G. The Provider can return to the procedure selection screen by hitting the 'Back' button 729 on the 'Procedure Details' screen 730. The 'Procedure Details' screen 730 displays expanded procedure information, including both the applicable code (here, the CPT code) 726 and the procedure description 727 in addition to the Transaction Code 731, Units 732, Diagnosis Pointers 733 and Modifiers 735. If the Provider does not wish to change the values for Units 732 (the default of which is one (1)), Diagnosis Pointers 733 (the default of which is one (1)), or the Modifiers 735 (the default of which is blank), then the Provider simply hits the 'Done' button 730 and is returned to the prior 'Procedure Details' screen. However, the Provider can click on the 'Units' bar 732 and the device's number pad will display, allowing the Provider to enter up to a double- digit number. Similarly, the Provider can click on the button to the right of the 'Diagnosis Pointers' bar 733 and will be taken to a further sub-template displaying diagnosis pointers. Lastly, the Provider can click on the 'Modifiers' display button 734 and will be taken to a further sub-template shown in FIG. 7H.

Figure 7H:
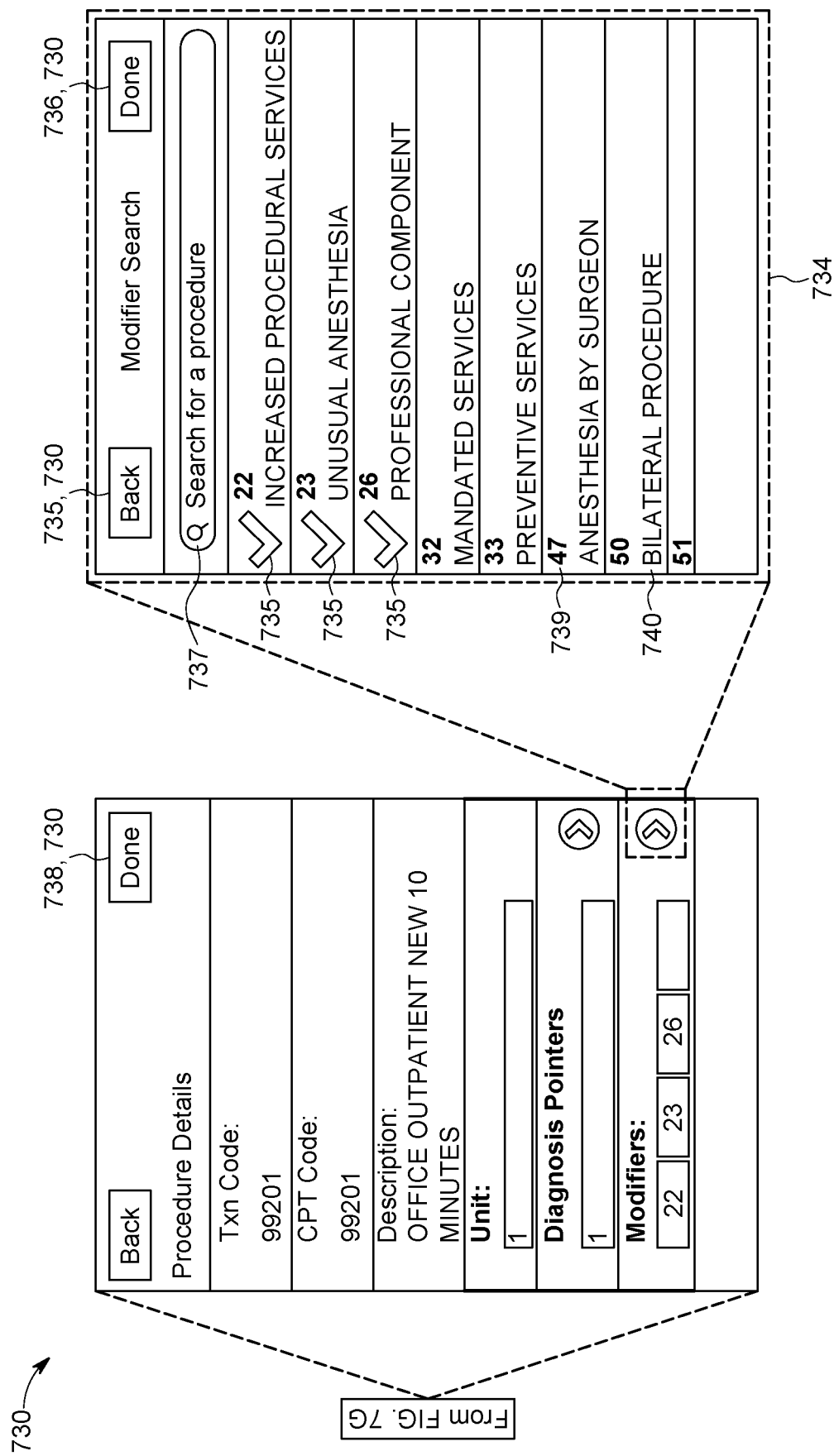
FIG. 7H is a screen shot view of an exemplary computer apparatus charge capture interface screen depicting a sub-template of a charge capture template image for adding a procedure per the 'Add Procedure' bar, according to FIG. 5A, FIG. 6A, FIG. 7F and FIG. 7G.
Figure 7I:
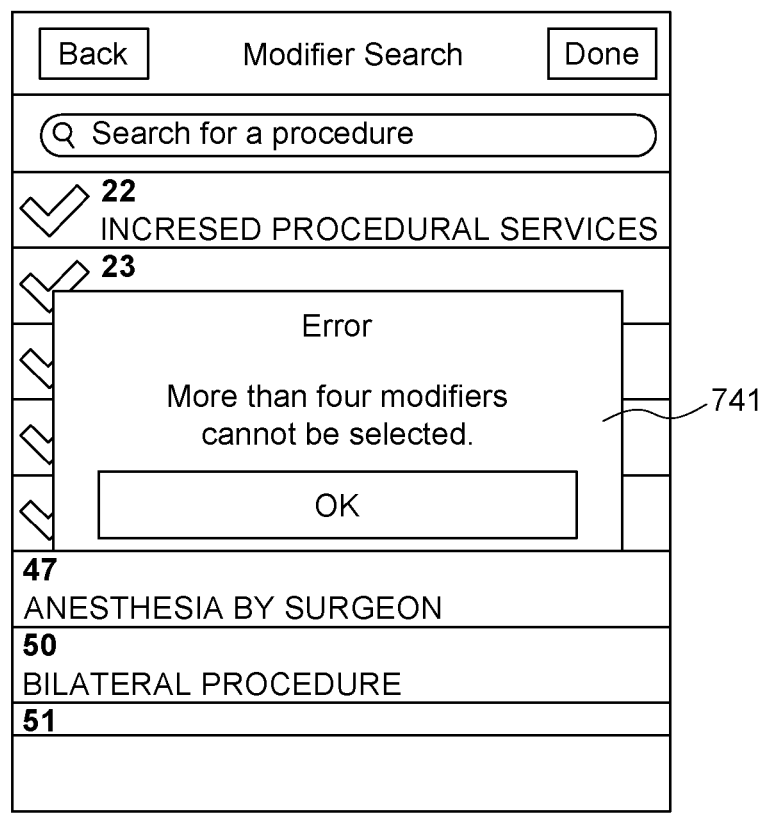
FIG. 7I is a screen shot view of an exemplary computer apparatus charge capture interface screen depicting a sub-template of a charge capture template image for adding a procedure per the 'Add Procedure' bar with an error message, according to FIG. 5A, FIG. 6A, FIG. 7F, FIG. 7G and FIG. 7H.
Figure 7J:
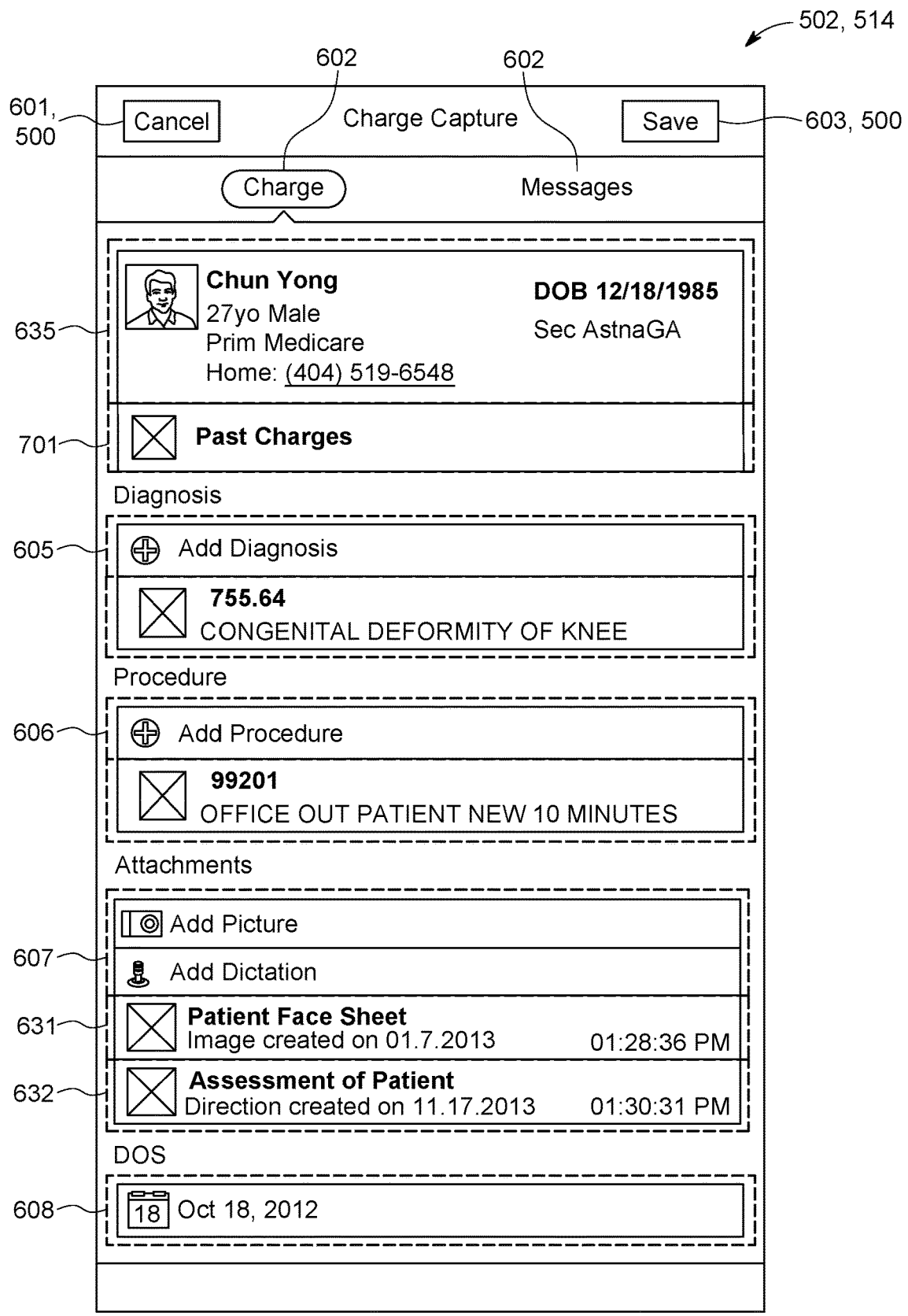
FIG. 7J is a screen shot view of an exemplary computer apparatus charge capture interface screen depicting a fully populated sub-template of a charge capture template image for adding a new charge capture, according to FIG. 5A, FIG. 6A, FIG. 7F, FIG. 7G and FIG. 7H.

In the sub-template for 'Modifiers' in FIG. 7H, the Provider can opt to return to the prior Procedure Details screen by hitting the 'Back' button 735 or the Provider can use the 'Search for a procedure' bar 737 to perform an incremental search for a procedure's modifiers, which search on the modifier description 740 and the modifier code 739, displaying the results on the screen. From this list, the Provider is able to select a plurality of modifiers 735. This feature can be further limited based on application, an exemplary limitation of four (4) modifiers shown in FIG. 7I displays an exemplary exception message 741.

Figure 7K:
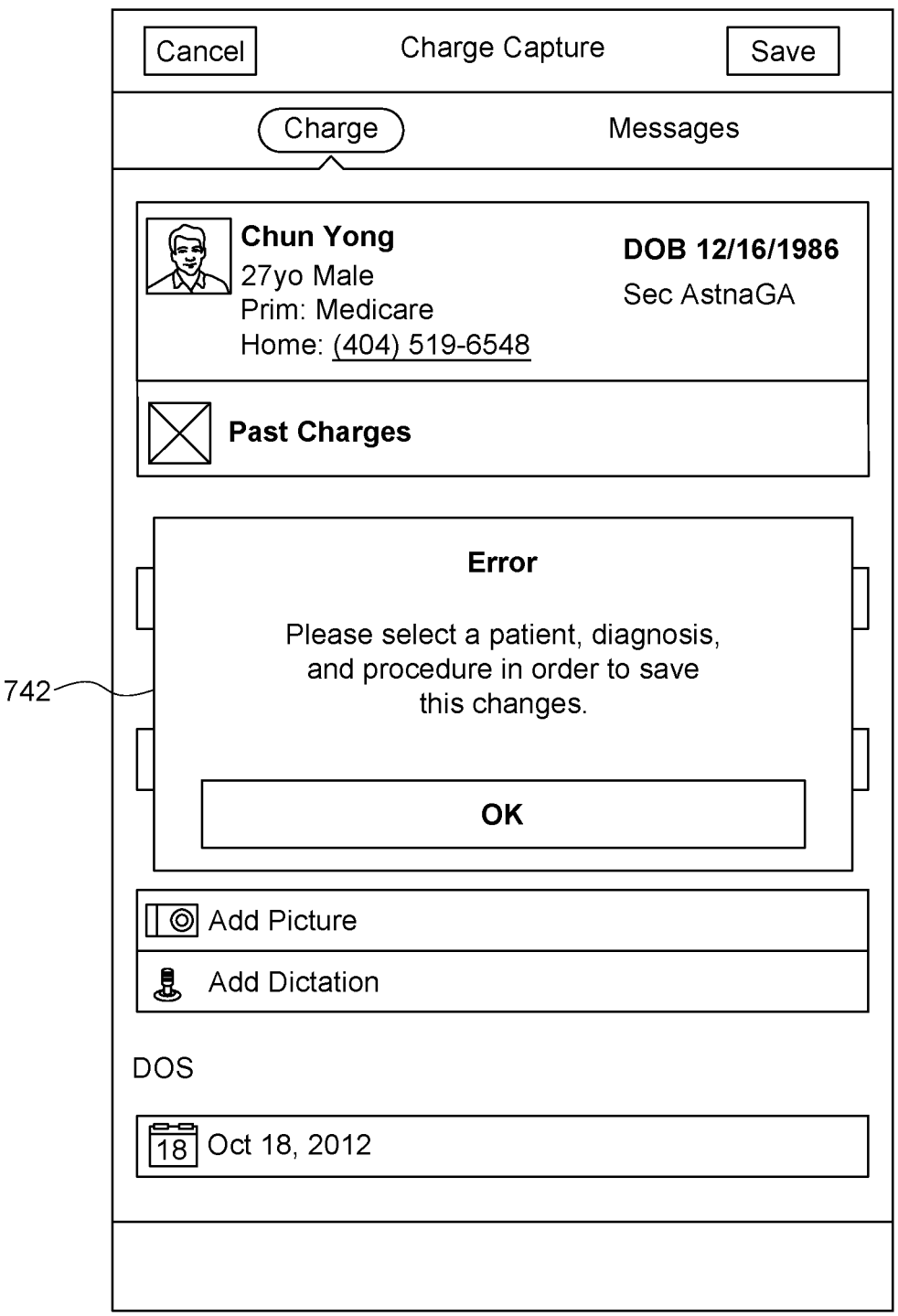
FIG. 7K is a screen shot view of an exemplary computer apparatus charge capture interface screen depicting a partially populated sub-template of a charge capture template image for adding a new charge capture with an error message, according to FIG. 5A and FIG. 6A.

Once the Provider has completed selecting modifiers, hitting the 'Done' button 736 returns the Provider to the prior Procedure Details screen shown on the left of FIG. 7H. Hitting the 'Done' button 738 on this screen returns the Provider to the prior initial sub-template screen for Procedure Details (730) shown in FIG. 7G. Here, the Provider can hit the 'Done' button 730 one last time and be returned to the new charge capture screen, shown in FIG. 7J' with the procedure selection 606 now populated 725. From this now fully-populated charge capture screen, if the Provider has left any critical information out, when clicking on the 'Save' button 603, an exception message 742 will be displayed (as shown in FIG. 7K). Otherwise, the new charge capture will be complete and saved in the system as charge capture data 301.

Turning now to FIG. 8A, a screen shot view of an exemplary interface screen depicting the display of a selection of a recent existing charge (charge capture data 301) created by the user, showing the ability to toggle 602 between the charge data 301 and its associated messages in a social media-styled conversation (charge capture- centralized conversation data 305). The left screen in FIG. 8A displays all of the populated charge capture data 301 compiled in the previous steps 514 (the same information that shows up as a charge listing in FIG. 5B on one of the initial screens for the module), and the right screen shows the charge capture template toggled 602 to the messages portion 800, showing a social media-styled conversation. On the left screen, a Provider has the ability to choose the 'Back' button 702, which will return the Provider to the initial module screen shown in FIG. 8A, or the Provider can choose to explore the charge capture data 301 displayed and perform actions on it (as discussed above and shown in FIG. 7C, like copy 709 or edit 710) by selecting the 'Action' button 707.

Within the messages portion 800, any charge-capture centralized conversation data 305 created for the selected charge capture data 305 (514) is shown in a social media-styled conversation. Here, the Provider can select the 'Cancel' button 601 and be returned to the initial module screen shown in FIG. 5A, or the Provider can choose to add a new message (new charge capture-centralized conversation data 305) by clicking in the 'Messages' bar 802. When the 'Messages' bar 802 is clicked, the computer apparatus' keyboard is displayed 808, allowing the Provider to type a message, according to FIG. 8B. Once the Provider has completed typing the message, clicking either the 'Send' button 803 or the 'Done/Enter/Return' button 809 on the computer apparatus' keyboard will cause the device to send the message (charge capture-centralized conversation data 305) to the Billing entity.

Also shown in FIG. 8B is an exemplary current message string. 804 shows the message prefix of the date and time stamp of a message sent by the current user (current user messages show up on the right side of the messaging screen, with a prefix that does not have the name of who sent the message) 80 shows an exemplary message sent by the current user. 806 shows the message prefix of the user's first and last name and date and time stamp of the message sent by a user other than the current user (messages sent by a user other than the current user show up on the left hand side of the messaging screen, with a prefix that has the name of who sent the message). 807 shows an exemplary message sent by a user other than the current user.

Similarly, a Provider can choose to add any relevant attachment by clicking on the 'Attachment' icon 801 (e.g. photos of service/product recipient, photos of documents like a service/product recipient face sheet, insurance card or other relevant documentation, dictations, etc.), which brings up a dialog box with options 811 from which the user can select, according to FIG. 8C. Here, the Provider can choose to add a picture by clicking on the 'Add Picture' button 812, or add a dictation by clicking on the 'Add Dictation' button 813 (both of which activate the first computer apparatus' peripheral device for the selected function) 810 shows an exemplary attachment added to the charge capture-centralized conversation data 305. These attachments are similar to the attachment options discussed in FIG. 7J for adding a picture or dictation 607 (exemplary service/product recipient face sheet 631 and dictation 632 shown). The Provider can also opt to cancel adding an attachment by clicking the 'Cancel' button 814 which will return the Provider to the charge capture messages section 800 previously discussed.

Desktop Billing Module

Turning now to FIG. 9A through 20, the relationship between an exemplary computer apparatus billing module interface 900, displayed on a second computer apparatus 108 or 109 with a computer apparatus billing module 112 and charge capture data 301, charge capture-centralized conversation data 305 and claim data 309 is shown. FIG. 9A depicts a screen shot view of an exemplary computer apparatus billing module 112 interface screen 900 depicting a charge capture computer apparatus billing module template image with an Inbox-styled pane on the left 902, a tabbed Charges pane 904 in the center, a tabbed Preview pane 906, and a Messages pane 905 on the bottom right. This interface enables the Billing entity to navigate to other features within the computer apparatus billing module (not discussed herein) via navigation buttons 901. Billing entities also have a separate set of navigation buttons on the bottom of the interface template 903 that enable them to navigate within the billing specific features discussed herein.

Figure 9B:
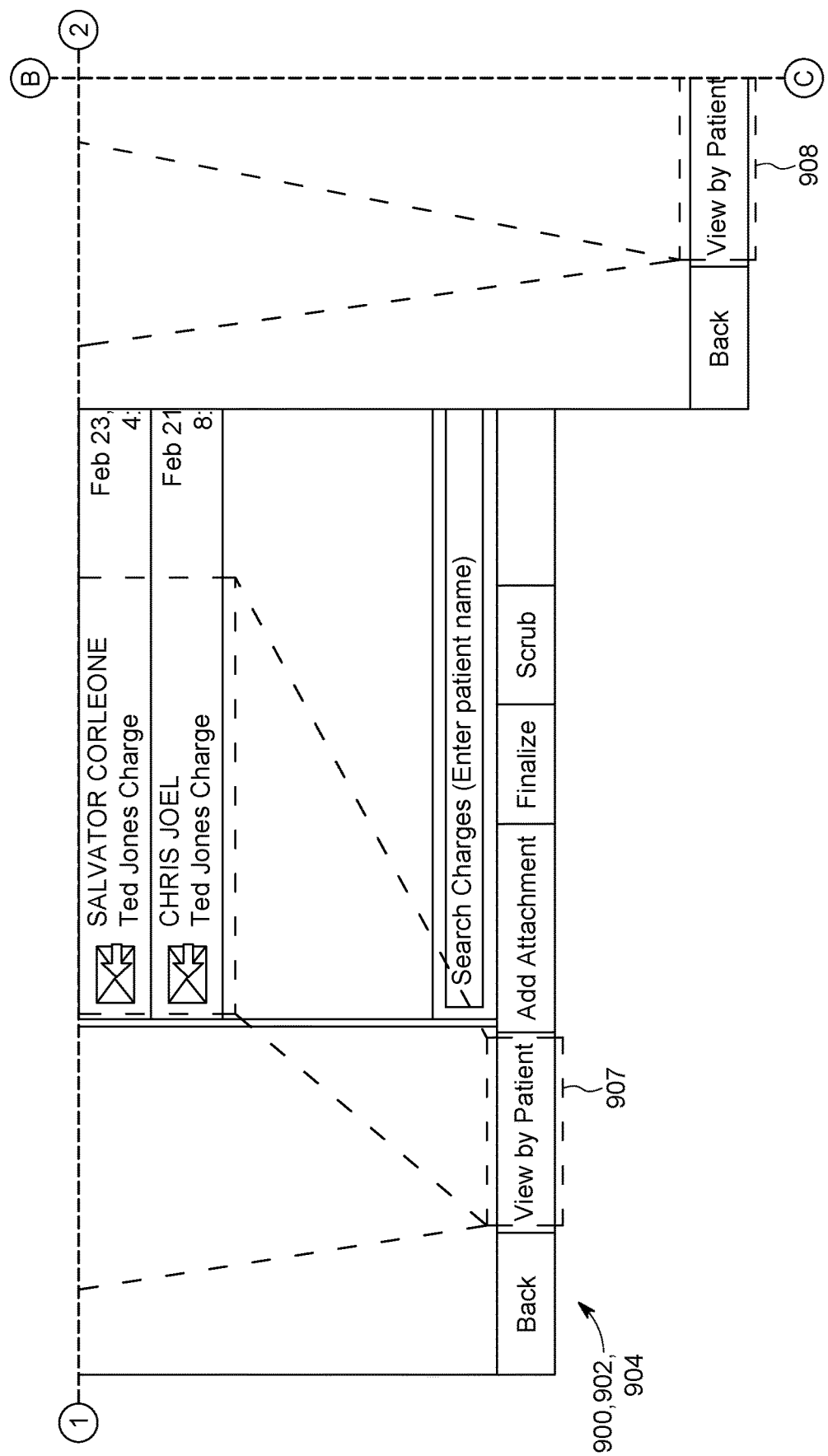
FIG. 9B is a screen shot view of an exemplary computer apparatus billing module interface screen depicting an Inbox-styled pane on the left and a tabbed Charges pane in the center, according to FIG. 9A.
Figure 9B:
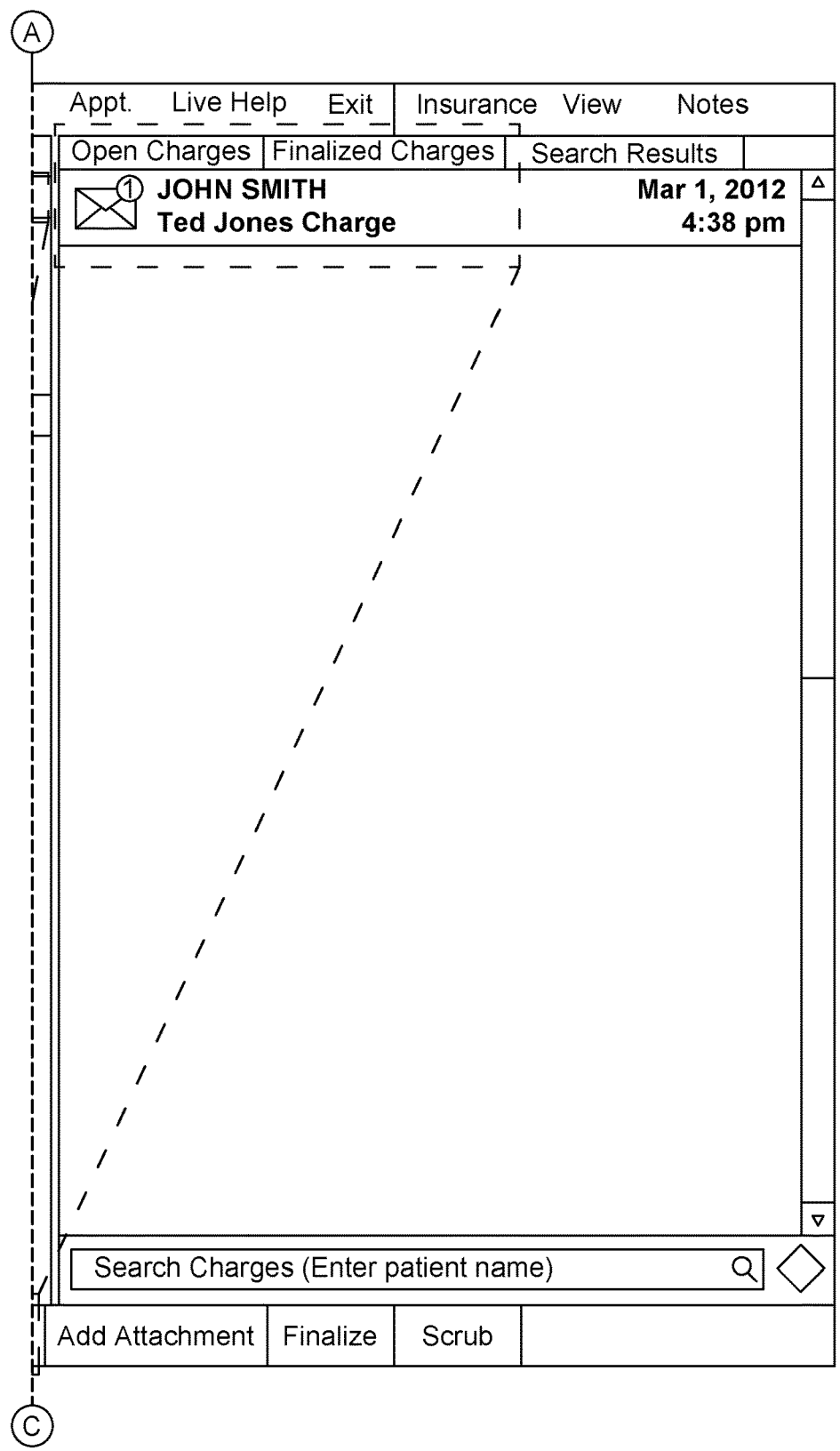

Continuing with FIG. 9B, the Inbox-styled pane 902 is expanded to better show what the Billing entity will see in the computer apparatus billing module 112 as well as specify the types of information included in the charge capture-centralized conversation message data 305 and the claim data 309. Here, a Billing entity will see a list of Provider inboxes and associated charges when in the 'View by Provider' view 907. A Billing entity can also click on the 'View by Service/product recipient' button that changes the view to list all charges pertaining to a service/product recipient, regardless of Provider 908.

Figure 15:
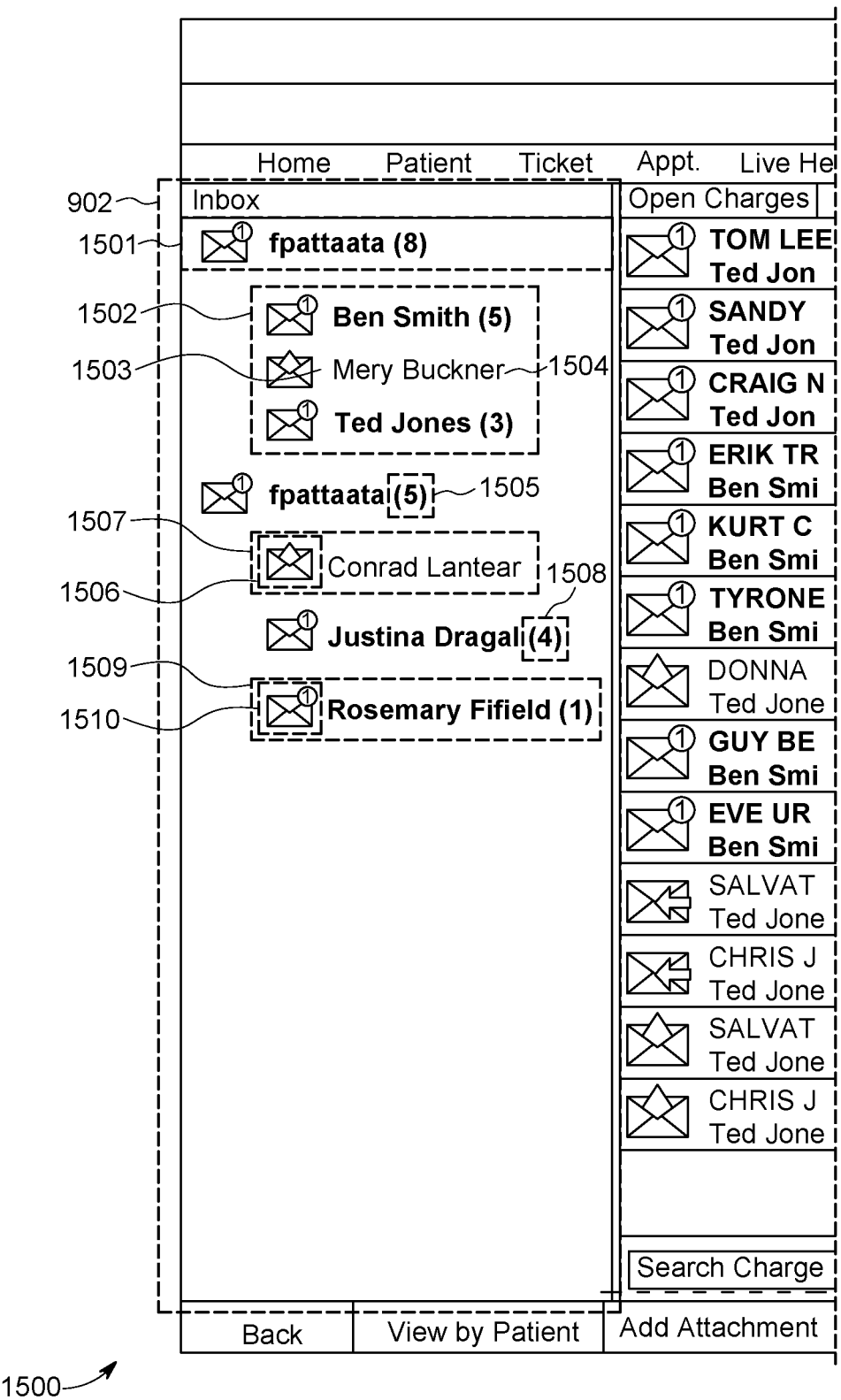
FIG. 15 is a screen shot view of an exemplary computer apparatus billing module interface screen depicting an Inbox-styled pane on the left, according to FIG. 9A.

Turning more particularly to FIG. 15, a further expanded view of the Inbox-styled pane 902 on the left with the 'View by Provider' view is depicted 1500. 1501 shows the Inbox account first level (Inbox account level"), designated by an account code listed in alphabetical order. 1502 shows the Inbox account second level (Inbox Provider level"), listing the various care Providers in alphabetical order by Provider first name 1503 then last name 1504. 1505 shows an icon next to the Inbox account level, indicating the total number of unread messages in the account code Inbox (between all Providers listed under the first level account code) 1506 shows an icon next to a Provider, indicating no unread charges or messages and 1507 shows the same Provider's name in normal (as opposed to bold) text, further indicating no unread charges or messages. 1508 indicates the number of unread charges or messages for a particular Provider and 1509 shows a different Provider's name bolded to indicate unread charges or messages. Similarly, 1510 is the icon next to the care Provider that indicates unread charges or messages and the number.

Figure 10A:
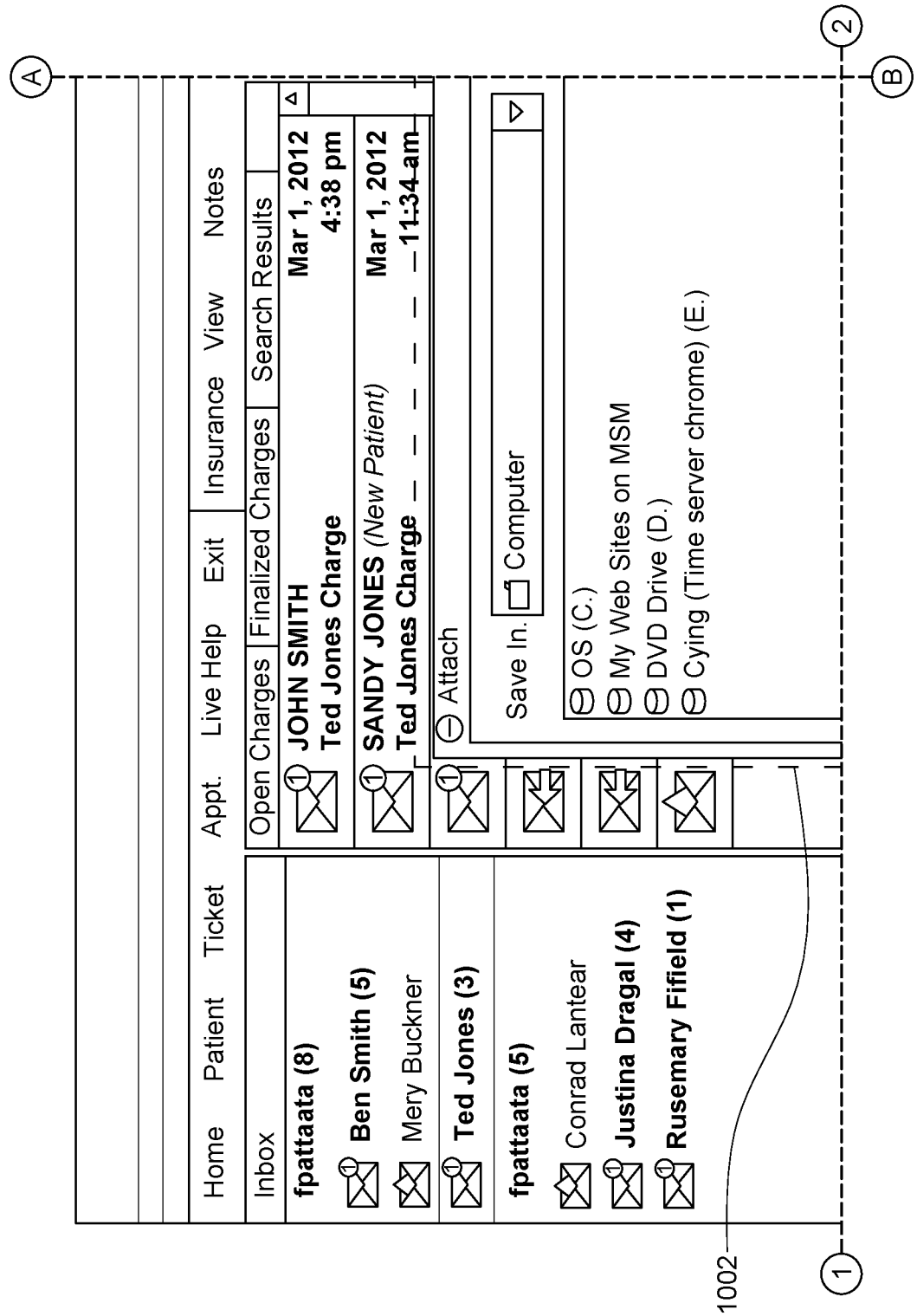
FIG. 10A is a screen shot view of an exemplary computer apparatus billing module interface screen depicting a charge capture billing template image, according to FIG. 9A, showing the 'Add Attachment' sub-template for attachments, according to an exemplary embodiment.
Figure 10A:
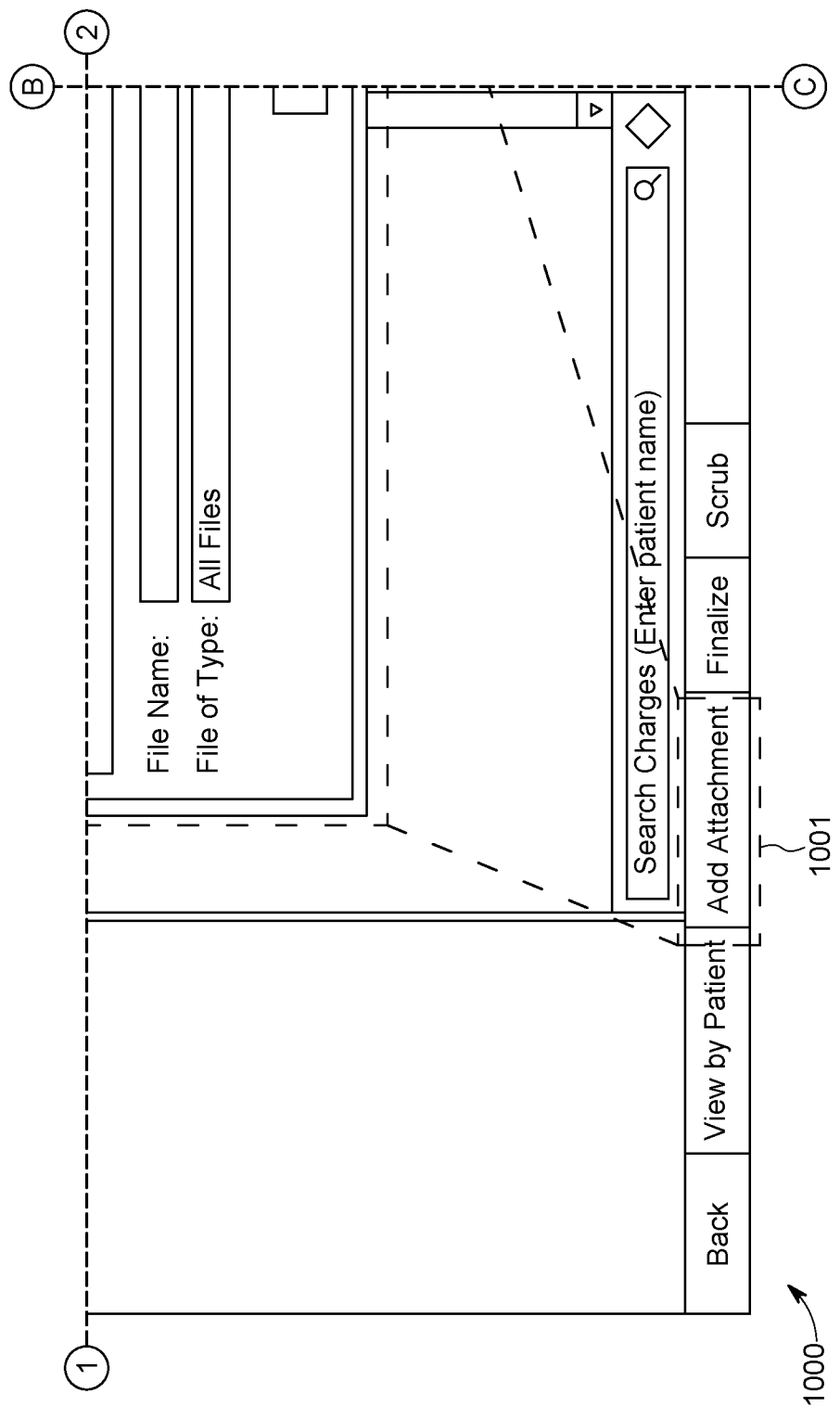
Figure 10A:
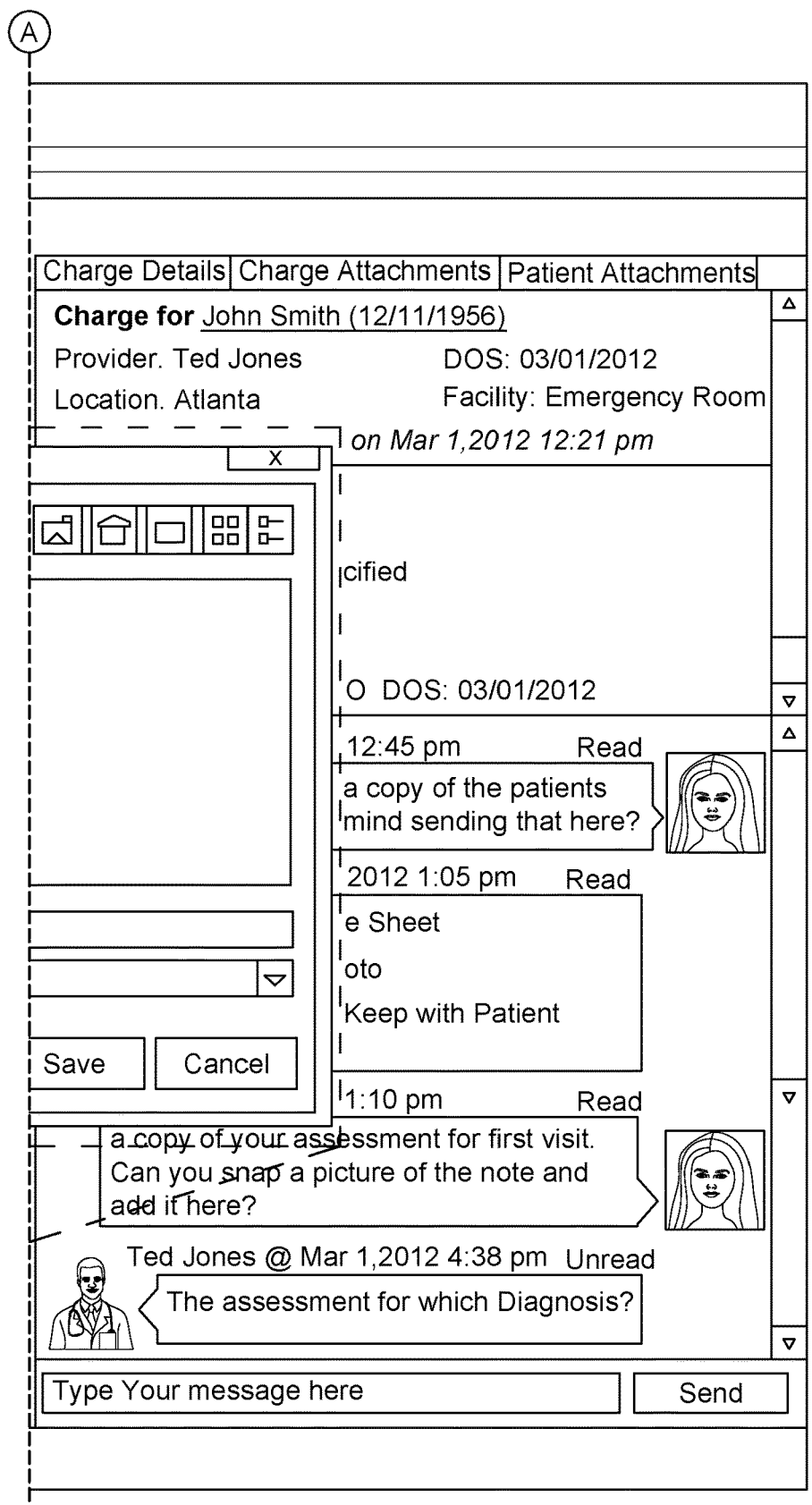

In FIG. 10A, the same exemplary screen shot from FIG. 9A is depicted, except the attachment feature is demonstrated. In order to utilize the attachment functionality, the Billing entity can be in either the 'View by Service/product recipient' view or the 'View by Provider' view (the 'View by Provider' view is shown here for exemplary purposes only) and have a charge selected, as shown 1000. From this screen, the Billing entity can then add any relevant attachment by selecting the 'Add Attachment' button 1001, which will display the file browser dialog box 1002, enabling the Billing entity to pick a file to attach to the selected charge.

Figure 10B:
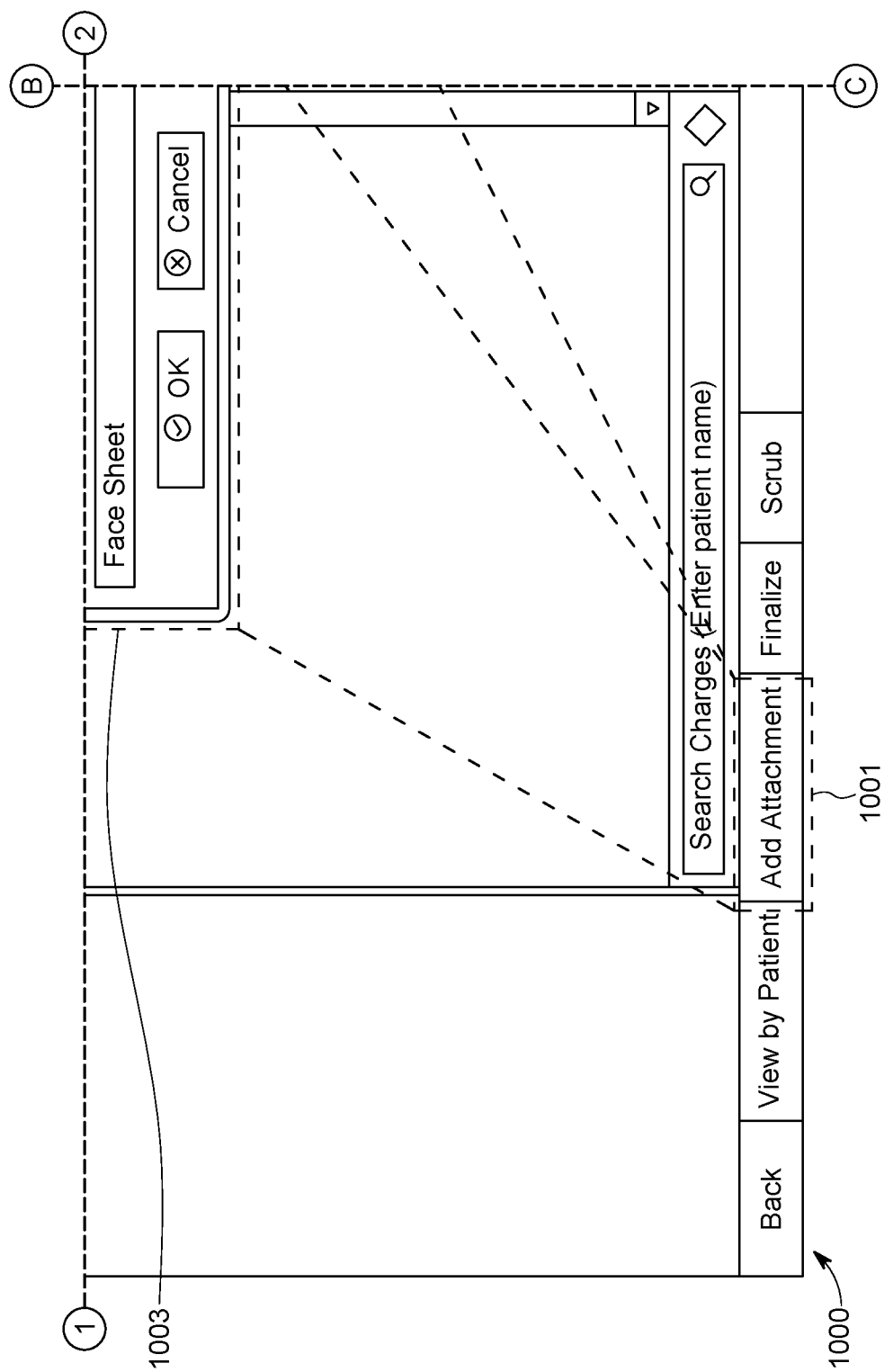
FIG. 10B is a screen shot view of an exemplary computer apparatus billing module interface screen depicting a charge capture billing template image, according to FIG. 9A, showing the 'Description' sub-template of the 'Add Attachment' sub-template feature, according to FIG. 10A.
Figure 10B:
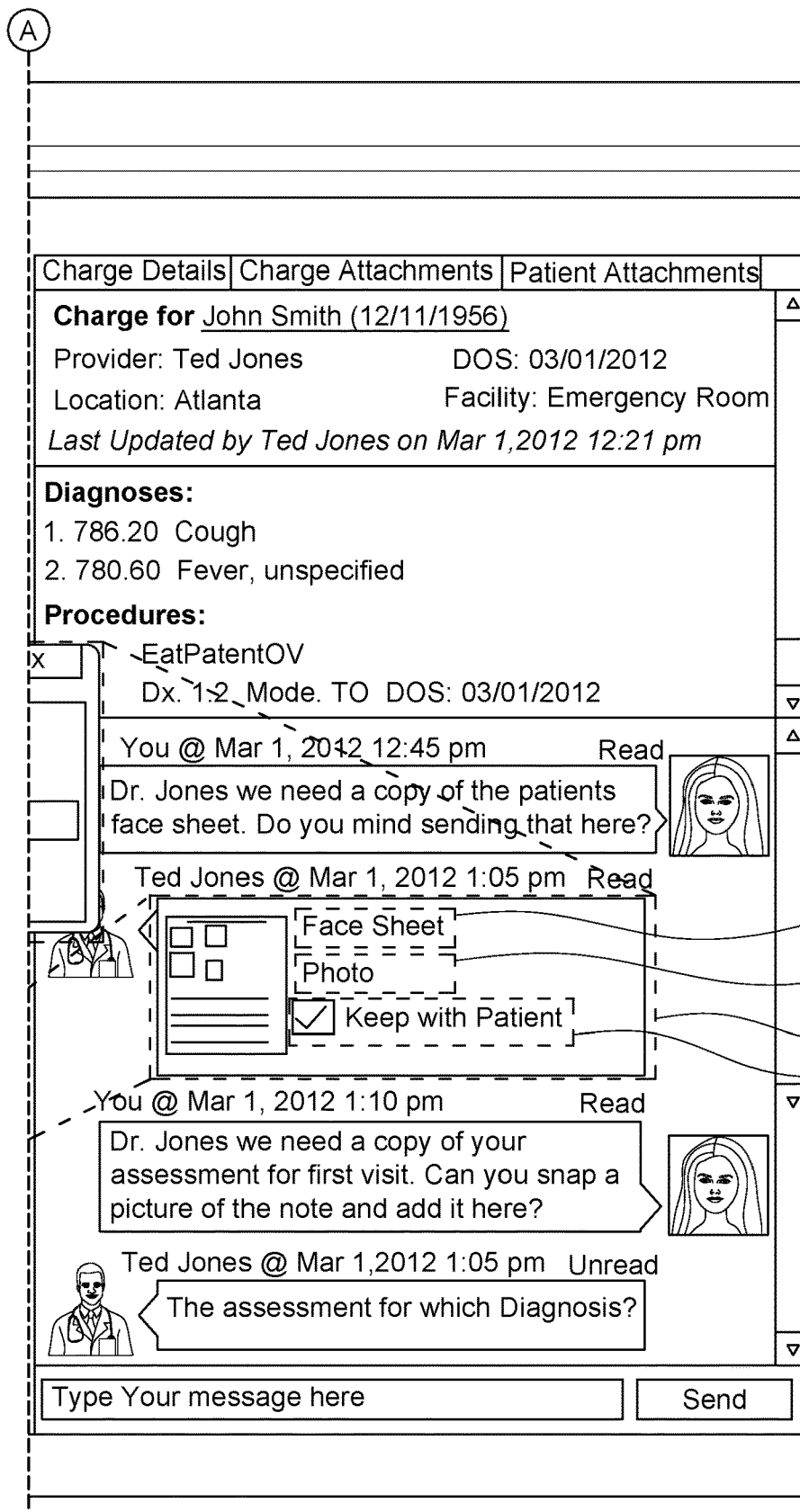

To complete the attachment step, FIG. 10B depicts a further dialog box that appears after the Billing entity has selected a file to attach to the selected charge. This 'Description' dialog box 1003 enables the Billing entity to give the file a descriptive name 1004. The attachment itself shows up in the message thread (charge capture-centralized conversation data 305 in the 'Messages' pane 905 on the bottom right of the screen. 1005 shows the attachment itself added to the message thread. 1004 shows the descriptive name of the attachment. 1006 shows the type of file that the Billing entity chose to attach and 1007 shows the 'Keep with the Service/ product recipient' toggle (unchecked by default), which allows the Billing entity to check it to keep the attachment with the service/product recipient (as opposed to only with the charge).

Figure 11:
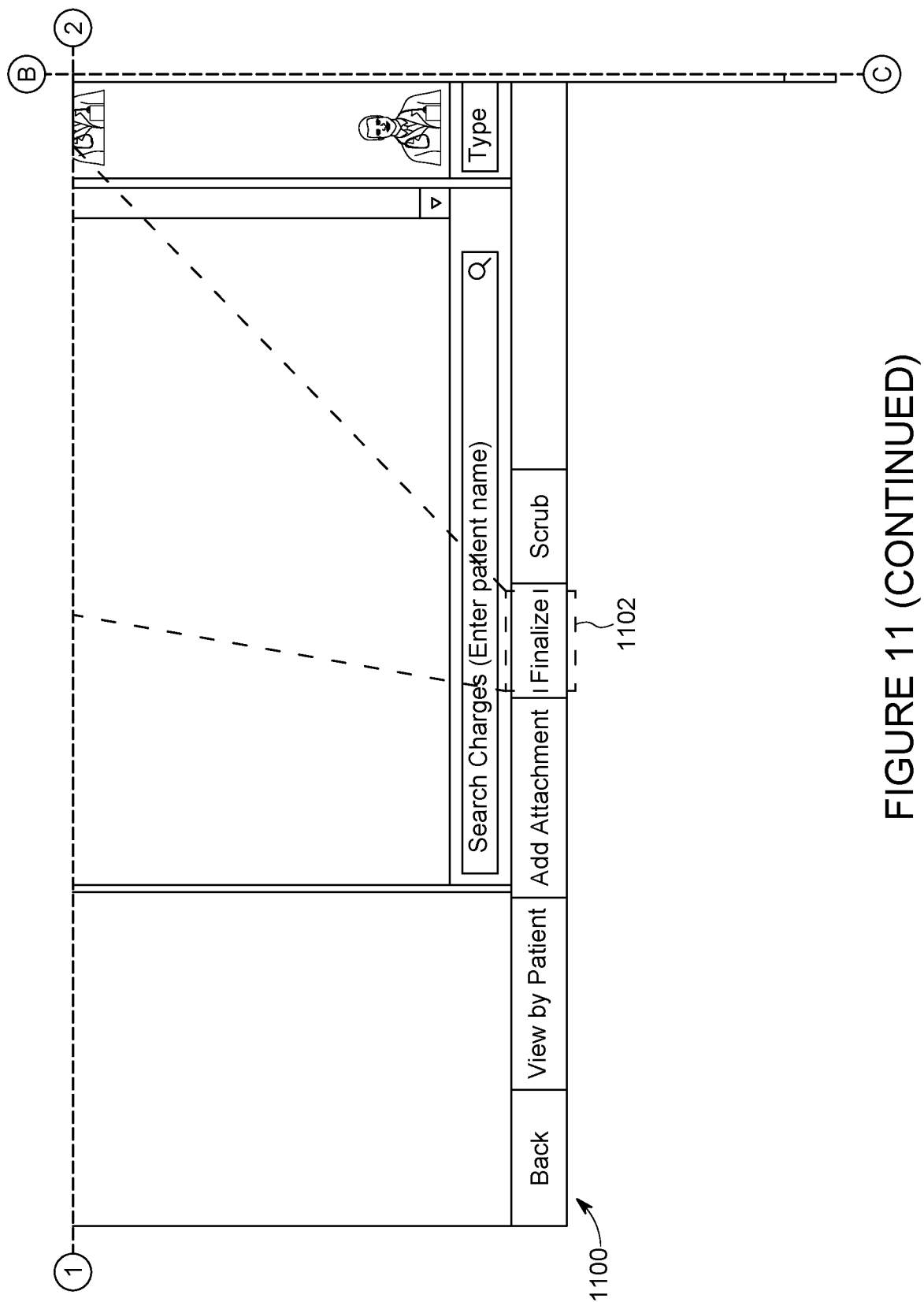
FIG. 11 is a screen shot view of an exemplary computer apparatus billing module interface screen depicting an Inbox-styled pane on the left and a tabbed Charges pane in the center, with the 'Open Charges' tab active and several charges chosen, showing the 'Finalize' feature, according to an exemplary embodiment.
Figure 11:
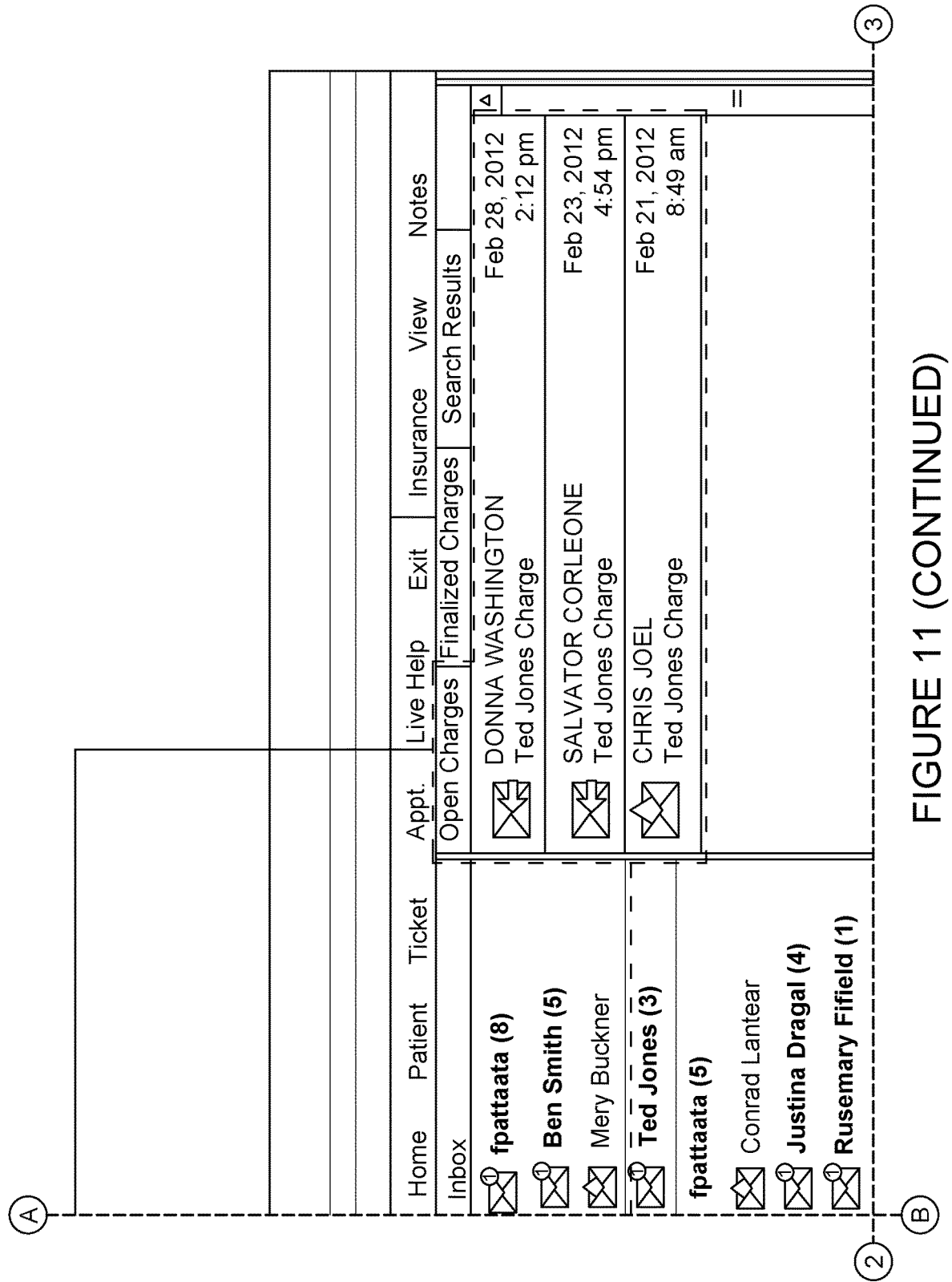
Figure 11:
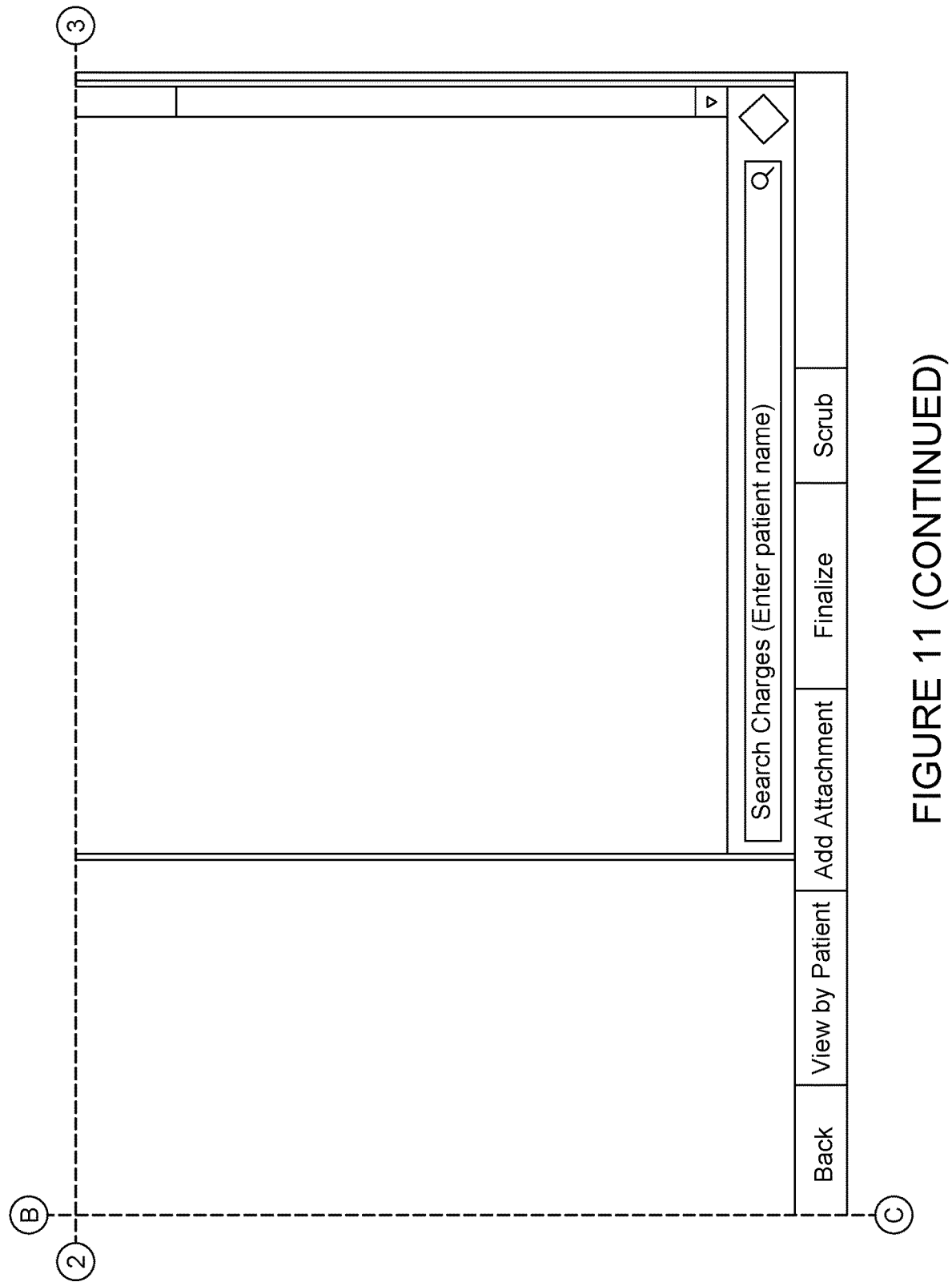

In FIG. 11, much the same exemplary screen shot from FIG. 9A is depicted, except the finalize feature is demonstrated. The finalize feature also allows the Billing entity to be in either the 'View by Service/product recipient' view or the 'View by Provider' view (the 'View by Provider' view is shown here for exemplary purposes only), but just as the attachment feature required, at least one charge must be selected, as shown 1100. The primary difference between the attachment function and the finalize function is that the finalize function allows multiple charges to be selected and requires the 'Open Charges' tab to be active, as shown 1103 (FIG. 18A, view 1800 shows the module's ability to select multiple charges 1801 from the charge listing displayed 904). The Billing entity can then click the 'Finalize' button 1102, which brings up the finalize dialog box 1101 to finalize the selected charge(s). This finalization step converts the charge capture data 301 into claim data 309. While the charge capture-centralized conversation data 305 is critical to accurate and efficient billing, it is not included in the claim data 309 because it is unnecessary to payers (presumably due to the Billing entity having included the pertinent information gleaned from the messages 305 into the charge 301 prior to finalization and conversion to claim data 309). Note: 1103 also displays the original selected messages to finalize from the 'Open Charges' tab removed from visibility after the completion of the finalization action.

Figure 12:
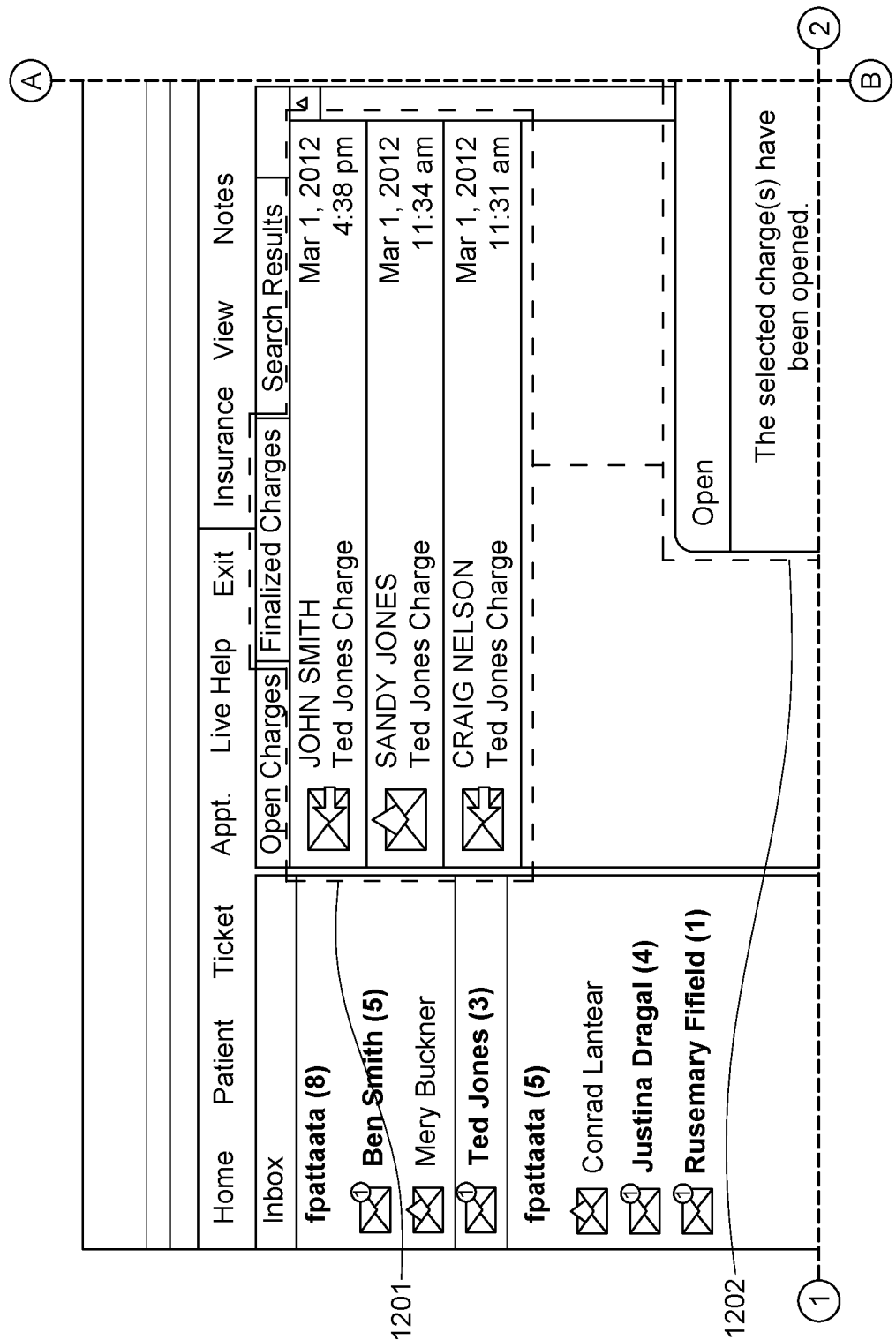
FIG. 12 is a screen shot view of an exemplary computer apparatus billing module interface screen depicting a charge capture billing template image, according to FIG. 9A, showing the 'Open' dialog box, with the 'Finalized Charges' tab active and several charges chosen, showing that they have been opened following finalization, according to an exemplary embodiment.
Figure 12:
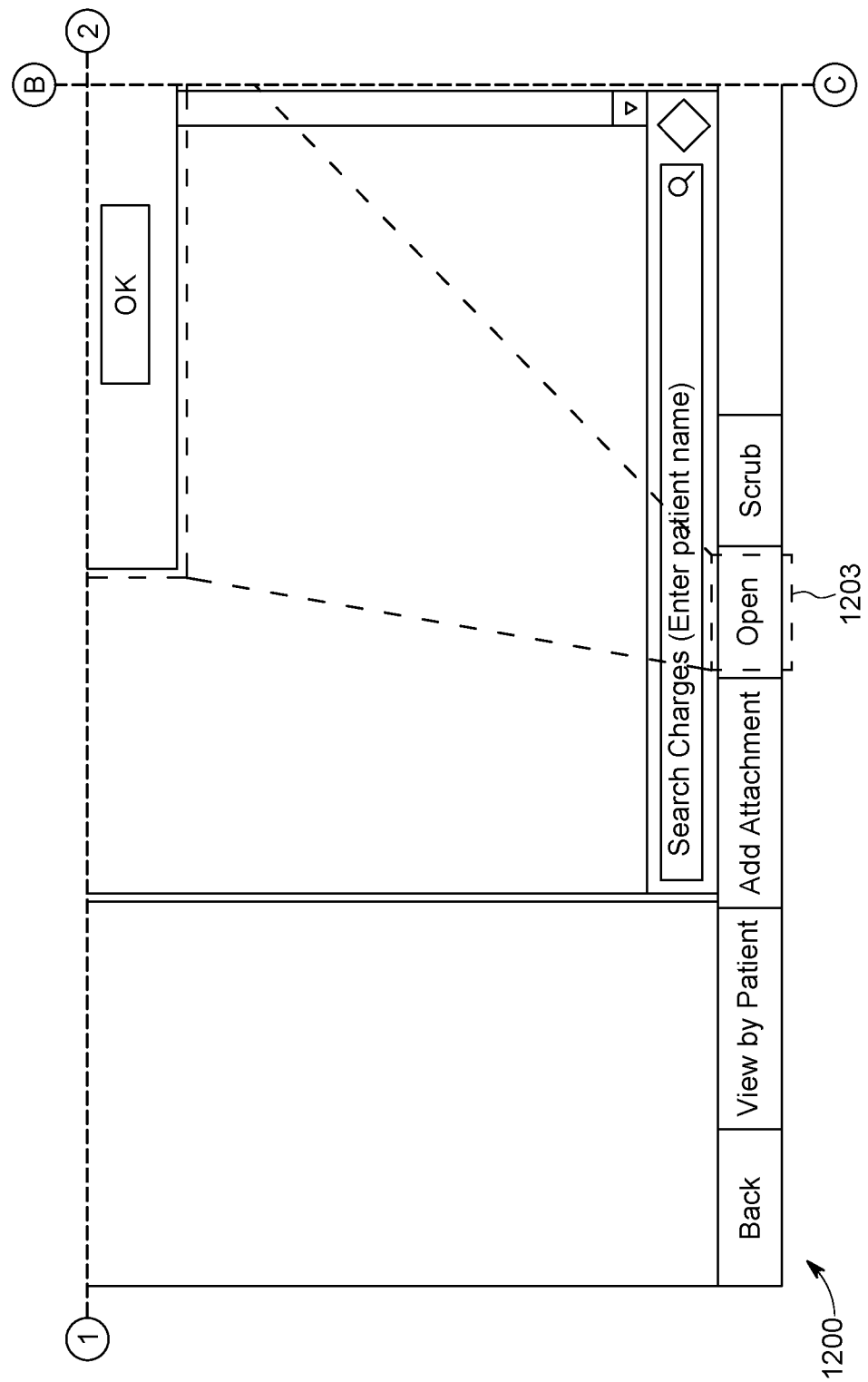
Figure 13:
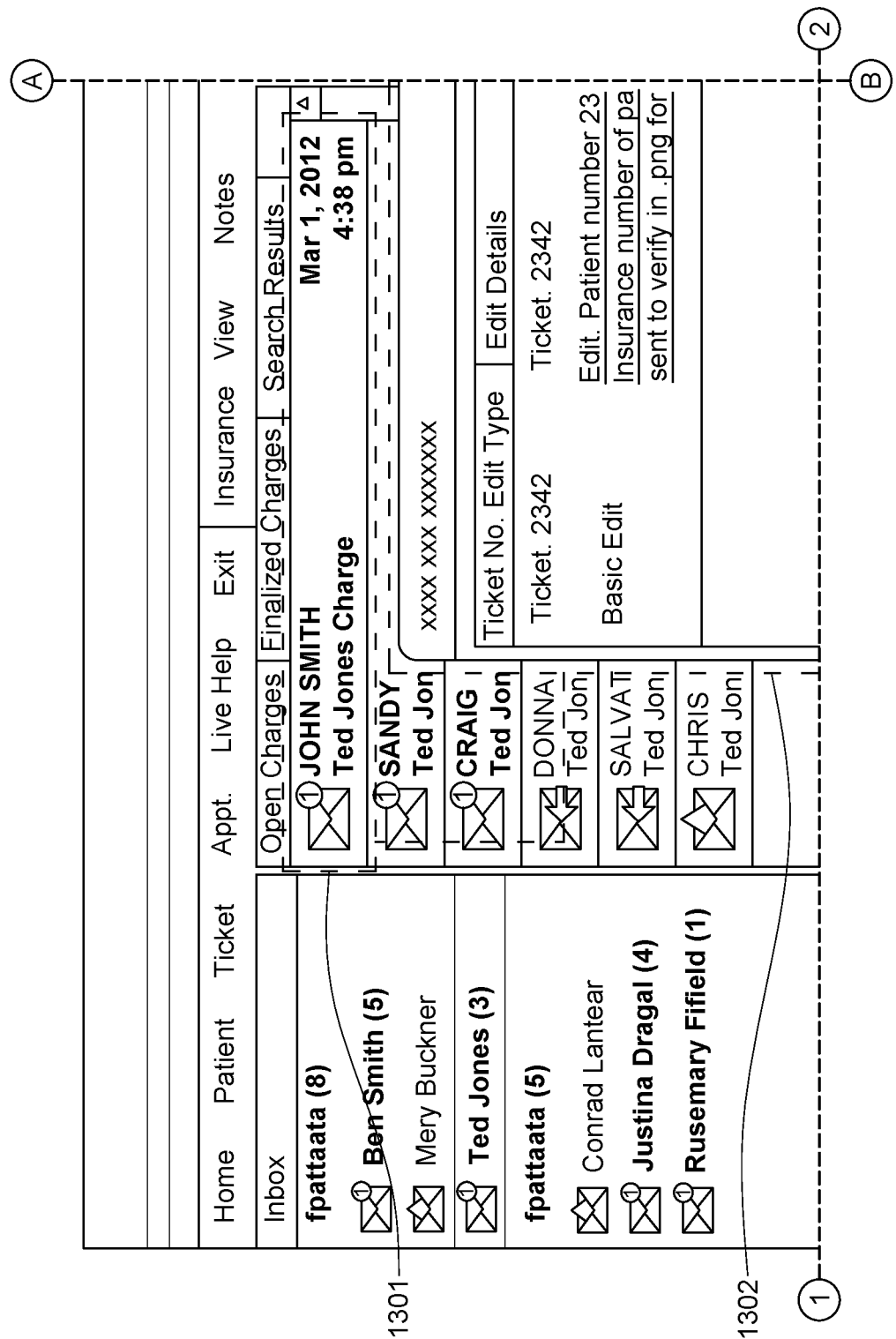
FIG. 13 is a screen shot view of an exemplary computer apparatus billing module interface screen depicting a charge capture billing template image, according to FIG. 9A, showing the 'Claim Scrub Results' dialog box, with the 'Open Charges' tab active and one (1) charge chosen, showing the details results of the claim scrub on the selected charge, according to an exemplary embodiment.
Figure 13:
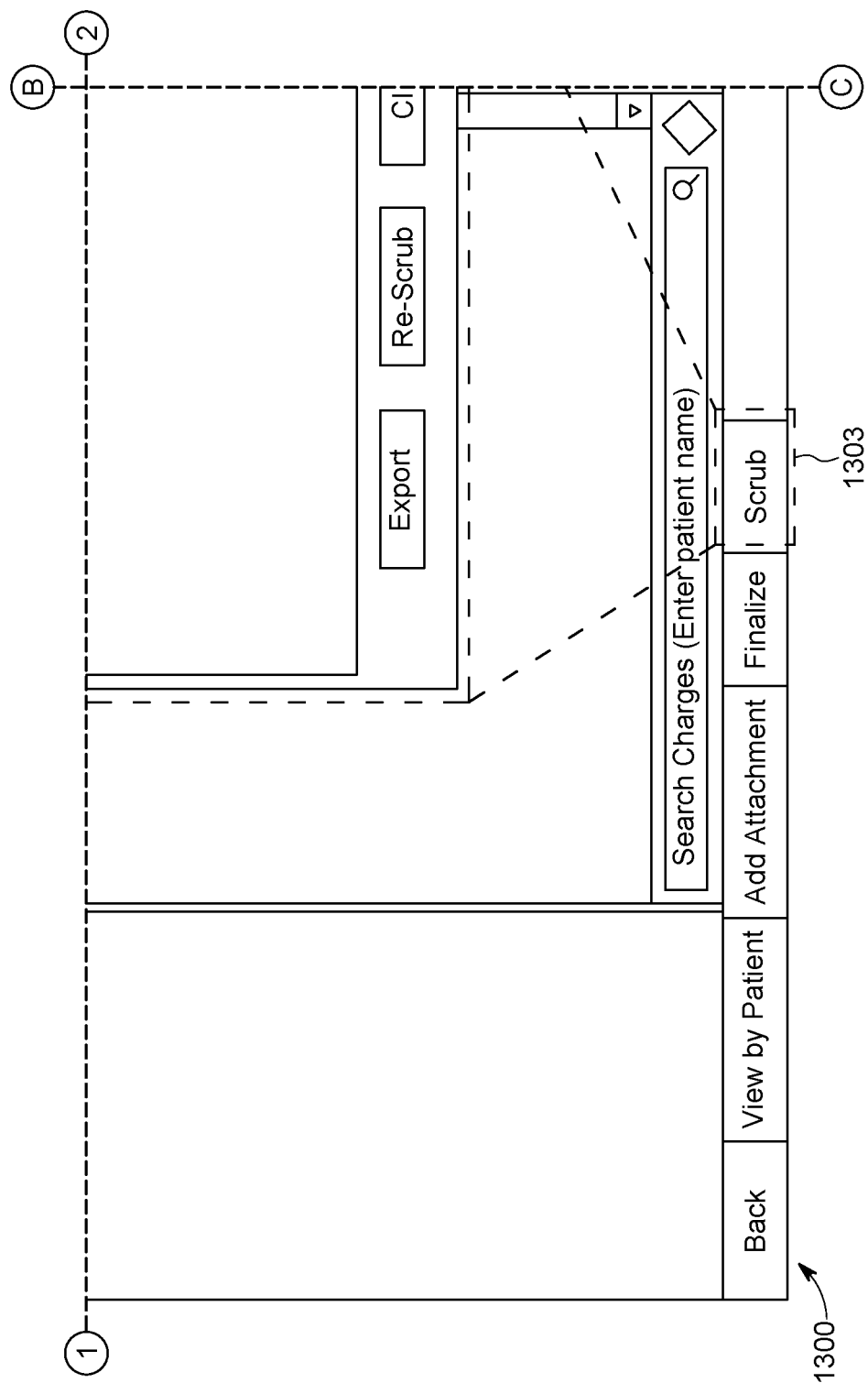

Likewise, FIG. 12 displays much the same exemplary screen shot from FIG. 9A, except the open charge feature is demonstrated. Again, the open charge features allows the Billing entity to be in either the 'View by Service/product recipient' view or the 'View by Provider' view (the 'View by Provider' view is shown here for exemplary purposes only), but just as the attachment and finalize function required, at least one charge must be selected, as shown in 1200. But unlike the aforementioned functions, the Billing entity must have the 'Finalized Charges' tab active. The Billing entity can then click the 'Open' button 1203, which brings up the open dialog box 1202 to open the selected (previously finalized) charges 1201.

FIG. 13 again displays much the same exemplary screen shot from FIG. 9A, except the claim scrubbing feature is demonstrated. Like the other functions, the claim scrubbing function allows the Billing entity to be in either the 'View by Service/product recipient' view or the 'View by Provider' view (the 'View by Provider' view is shown here for exemplary purposes only), and also just like the previous functions, a charge must be selected, as shown in 1300. Here, only a single charge can be selected on which to perform the claim scrubbing function, as shown by 1301 (alternatively, the system may be programmed to automatically scrub claims, hence the scrub claims function serves to allow a Billing entity to re-scrub previously scrubbed claims) The Billing entity can then click the 'Scrub' button 1303, which brings up the Claim Scrub Results dialog box 1302 to scrub the selected charge 1301.

Figure 14:
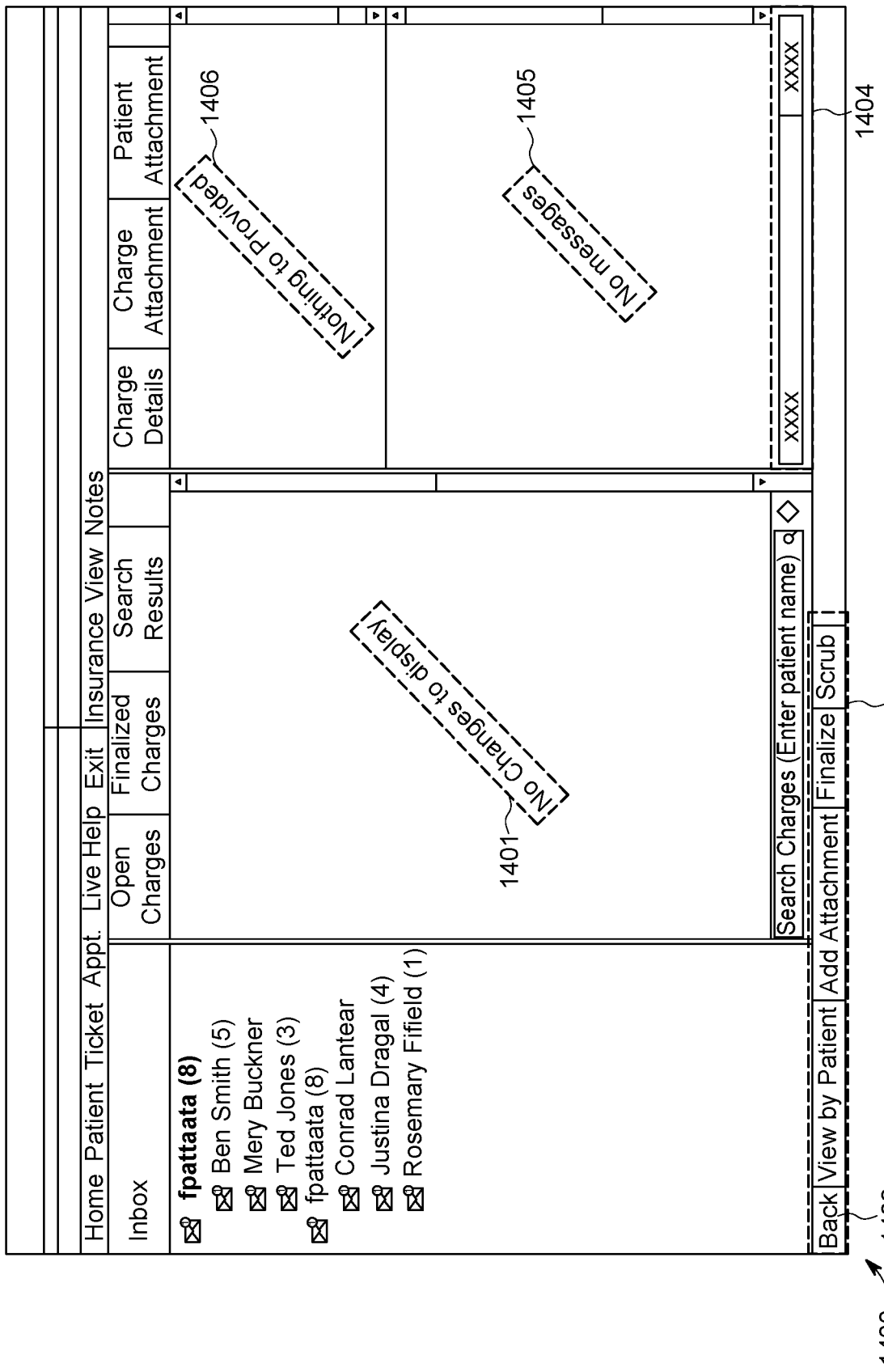
FIG. 14 is a screen shot view of an exemplary computer apparatus billing module interface screen depicting a charge capture billing template image, according to FIG. 9A, showing no open charges, according to an exemplary embodiment.

For exemplary purposes only, FIG. 14 displays the same exemplary screen shot from FIG. 9A, except this time, all the panes are empty. 1400 displays the 'View by Provider' view of the Inbox, Charges, Preview and Messages panes, 'Open Charges' tab active, with no charges in the Charges pane. 1401 shows the exception message in the Charges pane, 'Open Charges' tab active, showing 'No Charges to Display!' 1406 shows the exception message in the Preview pane, 'Charge Details' tab active, showing 'Nothing to Preview!' 140 shows the exception message in the Messages pane, showing 'No Messages!' Additionally, when there are no charges and no messages, the remainder of the billing navigation features 1403, with the exception of the 'Back' button 1402, are disabled. The 'Send Message' bar (as further shown in FIG. 20) is also disabled 1404.

Figure 16A:
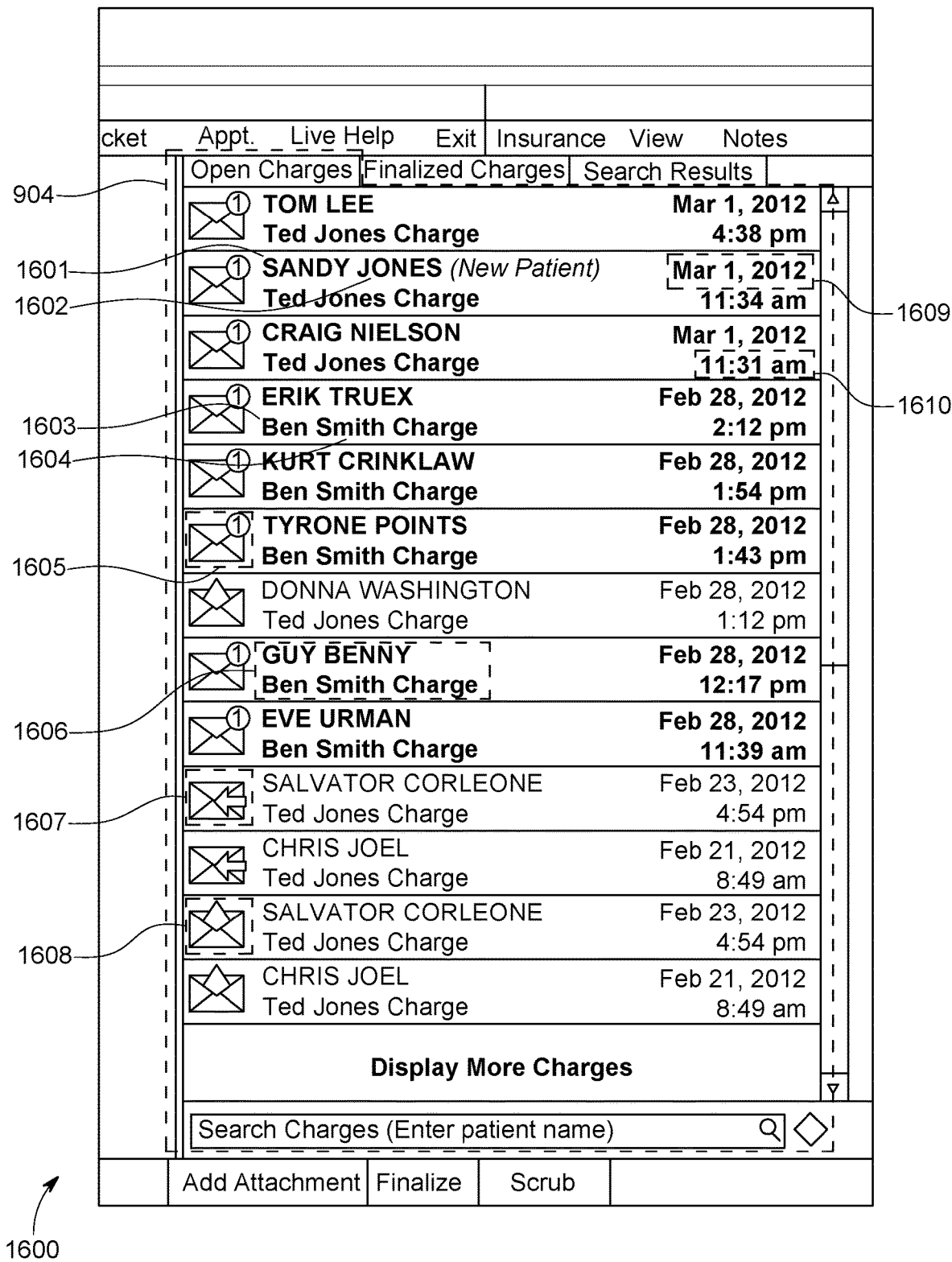
FIG. 16A is a screen shot view of an exemplary desktop interface screen depicting a tabbed Charges pane in the middle, 'Open Charges' tab active, according to FIG. 9A.

Continuing on to FIG. 16A, the center tabbed Charges pane 904 is depicted with the 'View by Provider' view and the 'Open-Charges' tab active 1600, displaying a list of charges (charge capture data 301) with messages (charge capture-centralized conversation data 305) . 1601 shows the Service/product recipient's first name and 1602 shows the Service/product recipient's last name. Whereas 1603 shows the Provider's first name and 1604 shows the Provider's last name. Identical to 1510 in the Inbox-style left pane, 160depicts an icon next to a charge, indicating unread charges or messages and the number. Additionally, similar to 1509, 1606 shows a charge bolded, indicating unread charges and/or messages. Likewise, 1607 is an icon next to a charge that indicates both a reply and no unread charges or messages. Whereas 1608 is an icon next to a charge that indicates no unread charges or messages, and no reply. 1609 is a charge's timestamp date and 1610 is a charge's timestamp time.

In FIG. 18B, the center tabbed Charges pane 904, with the 'Open Charges' tab active 1800 shows the 'New Service/ product recipient' indicator next to a new service/product recipient's charge listing 1802. In FIG. 18C, the center tabbed Charges pane 904 (with the 'Open Charges' tab active 1800 for exemplary purposes only) shows the option to display more charges (the 'Finalized Charges' and 'Search Results' tab also have this function). A Billing entity can click the 'Display More Charges' button 1803, and will see the next 100 charges displayed (the first 100 charges are displayed by default) In FIG. 16B, the center tabbed Charges pane 1611, with the 'Finalized Charges' tab active 1600 shows all the finalized charges for the selected Account, Provider or Service/product recipient (in this example, for exemplary purposes only, charges for the Provider are listed). The charges are grayed out, indicating they have been finalized.

Figure 17A:
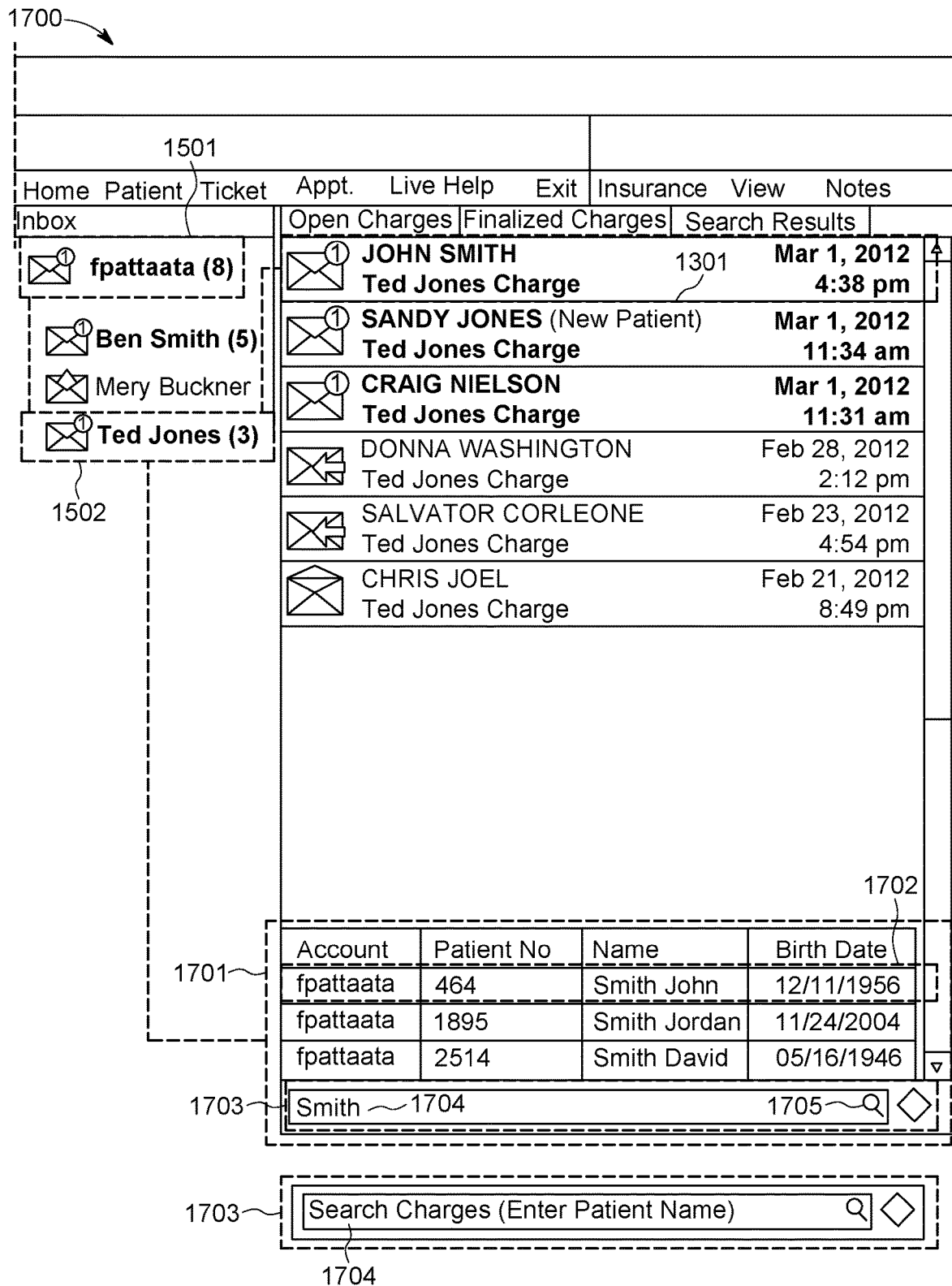
FIG. 17A is a screen shot view of an exemplary computer apparatus billing module interface screen depicting a tabbed Charges pane in the middle, 'Open Charges' tab active, according to FIG. 9A, showing the 'Search by Service/product recipient' bar dialog box, and one (1) Provider and corresponding charge chosen, showing the detailed results of the Search by Service/product recipient function on the selected charge, according to an exemplary embodiment.
Figure 17B:
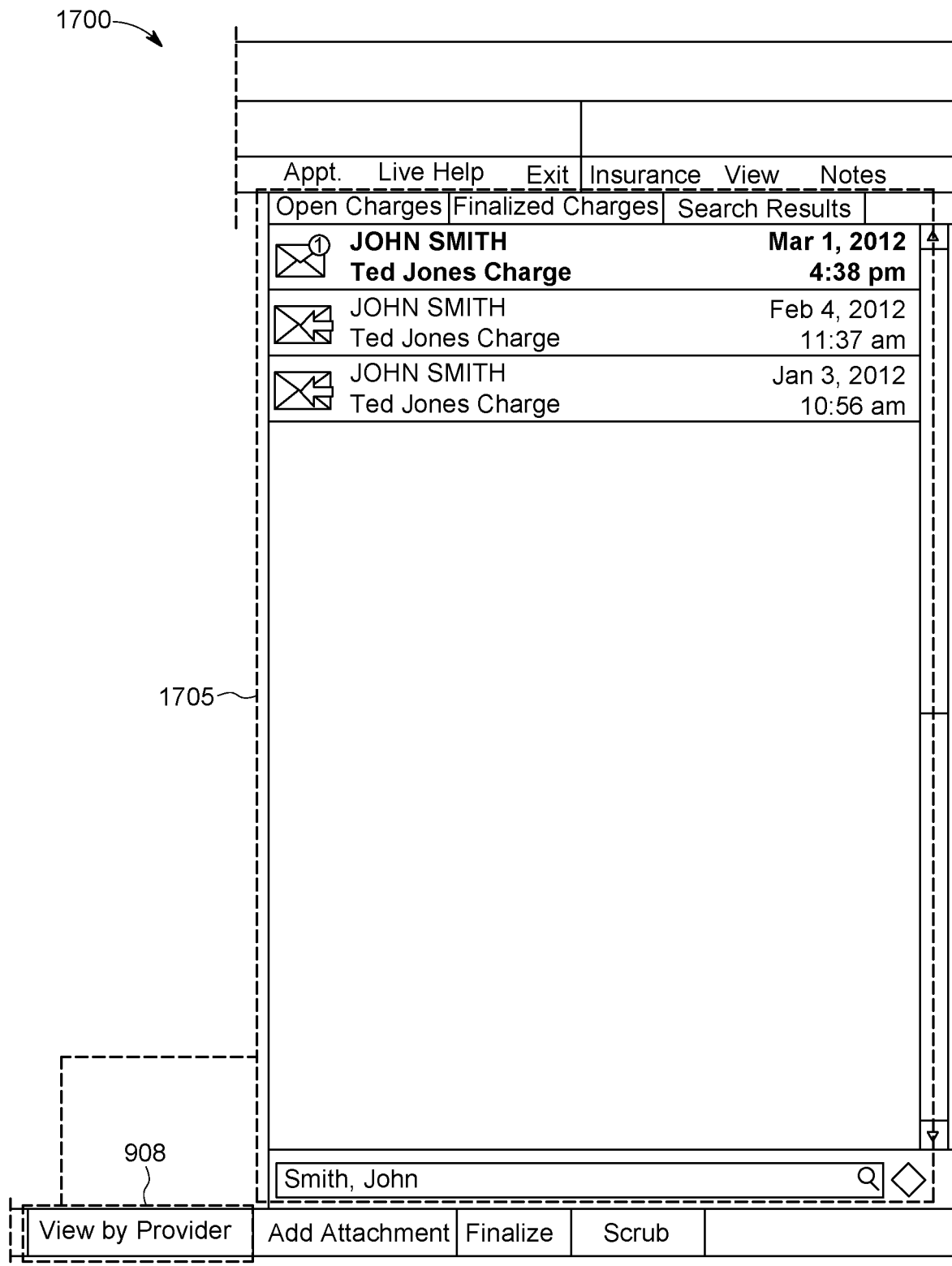
FIG. 17B is a screen shot view of an exemplary computer apparatus billing module interface screen depicting a tabbed Charges pane in the middle, 'Search Charges' tab active, according to FIG. 9A, showing the 'Search by Service/product recipient' function dialog box, showing the detailed results of the Search by Service/product recipient function, according to FIG. 17A.

Turning now to FIG. 17A, much the same exemplary screen shot from FIG. 9A is depicted, demonstrating the search by service/product recipient function. The 'View by Provider' view of the tabbed Charges pane, with the 'Open Charges' tab active is visible 1700, showing how a Billing entity can choose an Inbox Account Level account 1501, an Inbox Provider Level Provider 1502 and a corresponding charge 1301 to set the parameters 1704 of the search by service/product recipient function, initiated either automatically when the search parameters (search criteria) are set or by clicking the 'Search' button 1705. The results of a search by service/product recipient function, based on the account, Provider and charge selected are displayed in 1701. A Billing Entity can then select a listing in the search by service/product recipient function results 1702. If no criterion are selected/entered, the 'Search by Service/product recipient' bar 1703 is disabled (grayed out). FIG. 17B shows the detailed results of the search by service/product recipient function 1705 that are displayed in the Charges pane, 'View by Provider' view 908, 'Search Results' tab active 1700 when a Billing entity selects a listing from the search by service/product recipient function results.

Figure 17C:
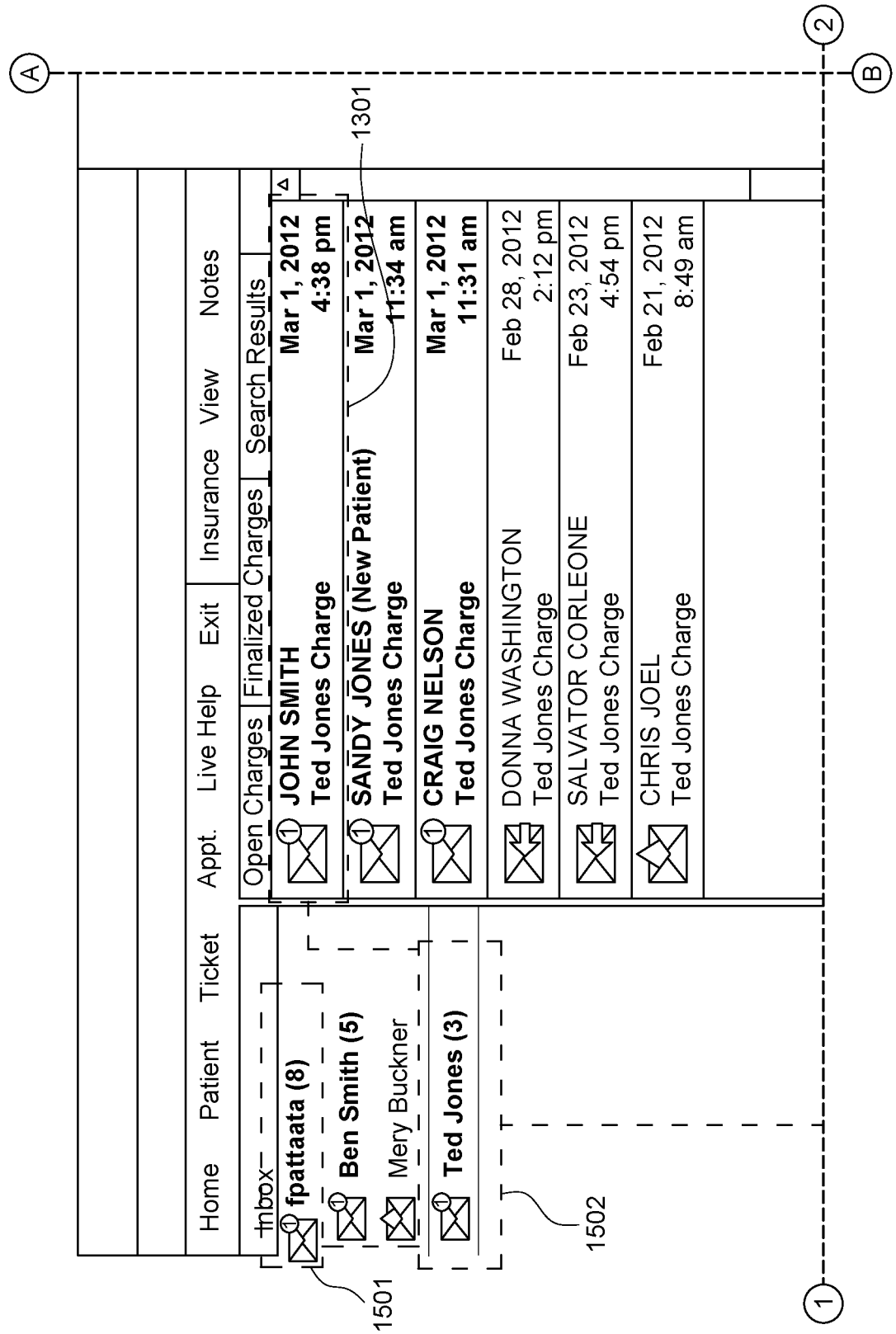
FIG. 17C is a screen shot view of an exemplary computer apparatus billing module interface screen depicting a tabbed Charges pane in the middle, 'Open Charges' tab active, according to FIG. 9A, showing the 'Search by Date' bar dialog box, and one (1) Provider and corresponding charge chosen, showing the detailed results of the Search by Date function on the selected charge, according to an exemplary embodiment.
Figure 17C:
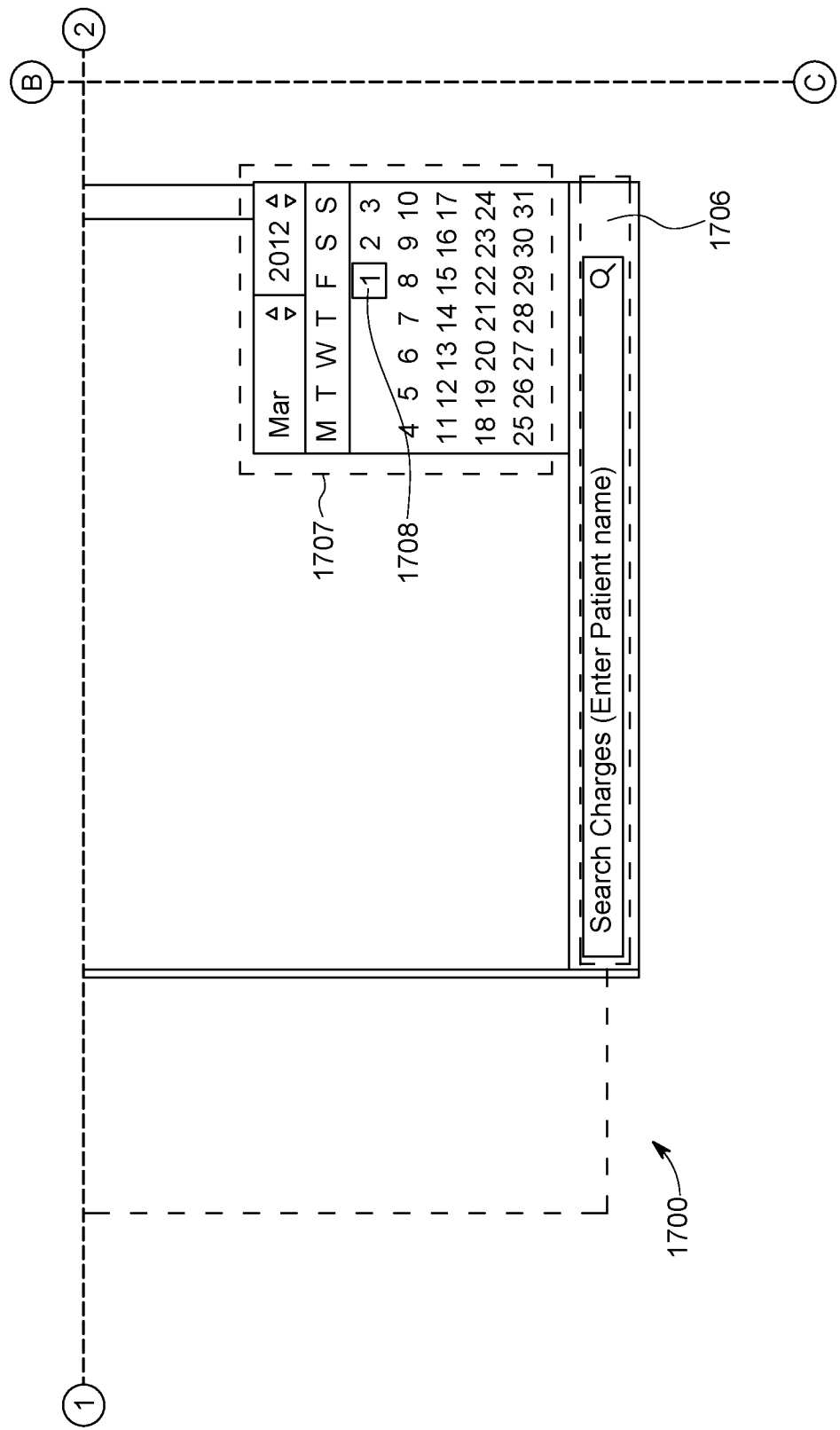

Turning now to FIG. 17C, much the same exemplary screen shot from FIG. 9A is depicted, demonstrating the search by date function. The 'View by Provider' view of the tabbed Charges pane, with the 'Open Charges' tab active is visible 1700, showing how a Billing entity can choose an Inbox Account Level account 1501, an Inbox Provider Level Provider 1502 and a corresponding charge 1301 to set the parameters 1708 of the search by date function, initiated by clicking the 'Search by Date' button 1706. Once the 'Search by Date' button 1706 is clicked, a calendar box 1707 pops up, showing the parameters of the search 1708. The detailed results of a search by date function, based on the account, Provider and charge selected, are displayed in Charges pane, 'View by Provider' view 908, 'Search Results' tab active 1700, 1706.

Figures 19A, 19B:
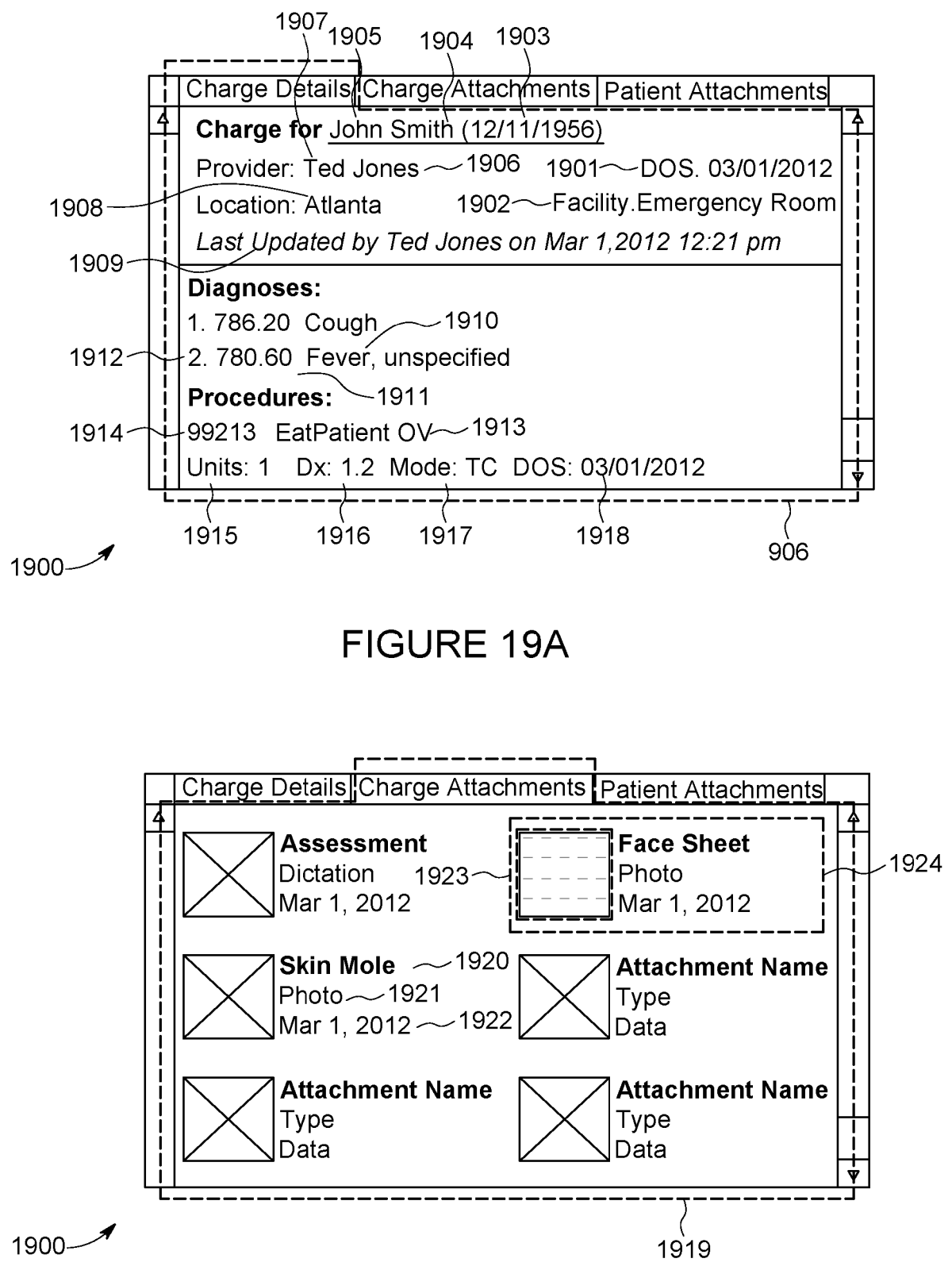

Continuing with FIG. 19A, the Preview pane 1900, 'Charge Details' tab active portion 906 of FIG. 9A is expanded to better specify the types of information included in the preview of charge capture data 301 shown in 900. Here, a Billing entity will see all of the details of an existing charge (existing charge data) that either the Billing entity added to the system or that a Provider sent to the Billing entity via its first computer apparatus 102 with an exemplary computer apparatus charge capture module 112 on it. The charge capture data 301 is identical to that shown in FIG. 5A as displayed on the computer apparatus charge capture module 112. 1901 identifies the date of the provided service. 1902 identifies the facility at which the service was provided. 1903 shows the service/product recipient's date of birth and 1904 the service/product recipient's first name, with 1905 the service/product recipient's last name. 1906 identifies the Provider's first name, while 1907 identifies the Provider's last name. 1908 shows the location of the facility where the services were provided. 1912 gives the number of the particular diagnoses (because there are often more than one), while 1911 gives the diagnosis code (here, an ICD9 code) and 1910 gives the diagnosis description. 1914 gives the procedure code (here, a CPT code) along with 1913 the procedure description. 1915 identifies the number of units of the procedure, 1916 specifies the diagnosis pointers, 1917 shows the modifiers selected and finally, 1918 identifies the date on which the procedure was rendered (not always the same date as the initial service shown by 1901). 1909 shows the last updated time stamp by first name, last name and date and time of the last save to the particular charge.

Moving on to FIG. 19B the Preview pane 1900, 'Charge Attachments' tab active portion 1919 of FIG. 9A is expanded to better specify the types of information included in the preview of charge capture data 301 that has attachments, shown in 900 and 1000. Here, a Billing entity will see the various attachments that have been added to the charge data 301 either by the Billing entity or the Provider. 1920 shows the file description of the attachment (as originally shown in FIG. 10B and the type of file attached 1921 (photo, dictation, etc.)(as originally shown in FIG. 10A). 1922 identifies the date the attachment was created and 1924 shows an exemplary charge attachment, displayed in a tile format in alphabetical order sorted based on file description left to right, top to bottom with an image preview based on the file's extension 1923 (in this case, a photo of a service/product recipient's face sheet is shown for exemplary purposes only, and thus the image of the attachment is a thumbnail of the photo).

Figure 19C:
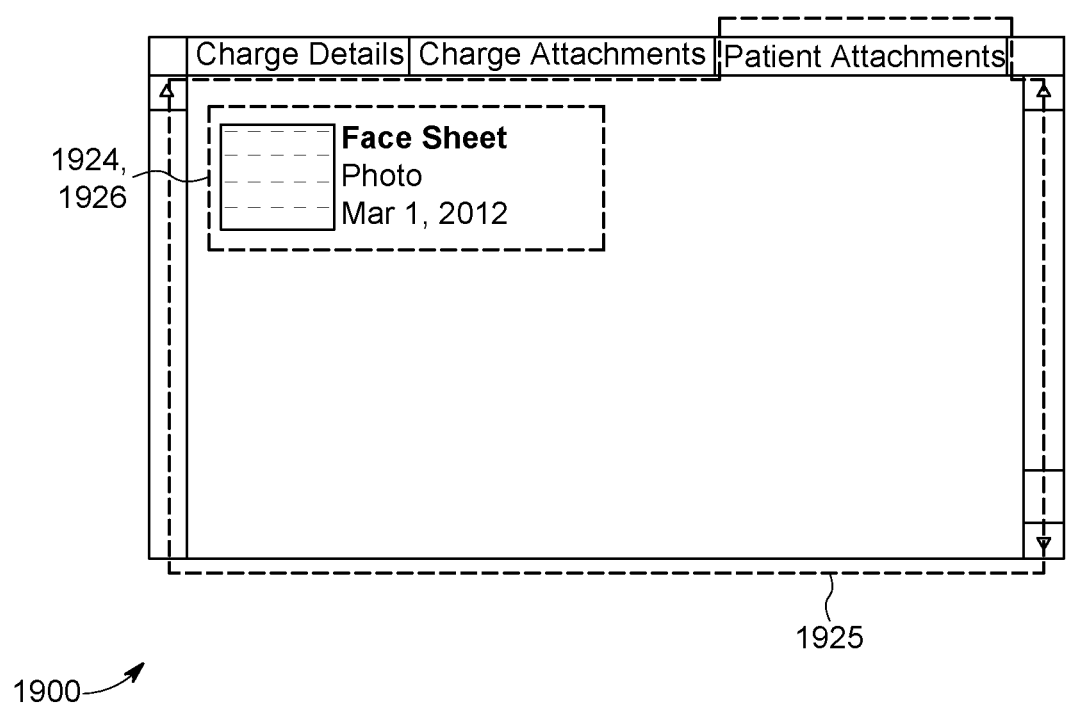
FIG. 19C is a screen shot view of an exemplary computer apparatus billing module interface screen depicting a tabbed Preview pane on the top right, with the 'Service/product recipient Attachments' tab active, according to FIG. 9A.

Similarly, FIG. 19C shows the Preview pane 1900, 'Service/product recipient Attachments' tab active portion 1925 of FIG. 9A is expanded to better specify the types of information included in the preview of charge capture data 301 that has attachments, shown in 900 and 1000. Here, a Billing entity will see the various attachments 1926 (same attached shown in FIG. 19B 1924) that have been added to the charge data 301 either by the Billing entity or the Provider (messages that have received the 'Keep with Service/product recipient' toggle option selected (as originally shown in FIG. 10B 1007 and further shown in FIG. 20)). This distinction is important because those attachments added to a charge will always remain part of the charge data 301, however only those toggled 'Keep with Service/product recipient' 1007 will remain additionally with the actual service/product recipient's data file as well (a different type of stored data not discussed herein).

Figure 20:
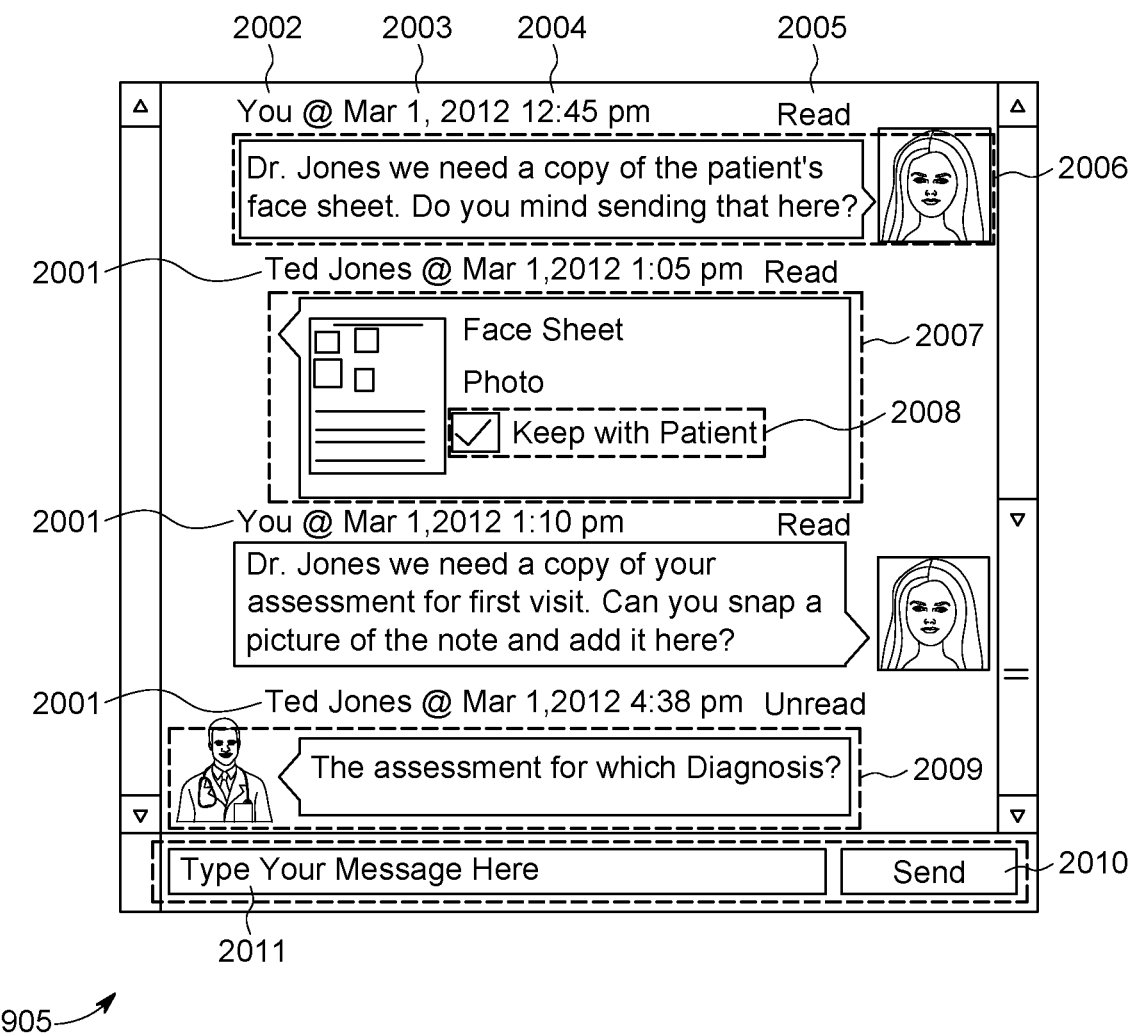
FIG. 20 is a screen shot view of an exemplary computer apparatus billing module interface screen depicting a Messages pane on the bottom right, according to FIG. 9A.

Finally, FIG. 20 shows the Messages pane 90 of FIG. 9A expanded to better specify the types of information included in the charge capture-centralized conversation data 305, shown in 900. Here, a Billing entity will see all of the details of an existing charge's messages (existing charge capture-centralized conversation data 305) that either the Billing entity sent to the Provider or that a Provider sent to the Billing entity via its first computer apparatus 102 with an exemplary computer apparatus charge capture module 112 on it. The charge capture-centralized conversation data 301 is nearly identical to that shown in FIG. 8B as displayed on the computer apparatus charge capture module 112. 2001 shows the message prefixes identifying the sender. 2002 shows a specific message prefix showing the current user is the one who sent the exemplary message. 2003 shows the date the message was sent and 2004 shows the time the message was sent. Furthermore, 200 identifies whether the message's read or unread status.

Continuing with FIG. 20, 2007 shows a message with an attachment sent by a Provider. 2008 highlights the 'Keep with Service/product recipient' toggle option 1007 previously discussed. 2009 shows a message sent by a Provider without an attachment. Unlike the charge capture- centralized conversation data shown in FIG. 8B, the computer apparatus billing module 112 shows the current user's profile picture 2006 with each message sent (unlike the computer apparatus charge capture module where it is unlikely for more than one Provider to be using a particular first computer apparatus 102, the computer apparatus billing module may be used by multiple individuals on a Billing entity's staff, thus it is helpful to further identify, beyond simple prefix, the actual sender of the message data 305). Lastly, 2011 shows the 'Type Your Message Here' bar used by the Billing entity to type a message to a Provider and 2010 shows the 'Send' button where the Billing entity can send the message just typed to the Provider.

The foregoing description and drawings comprise illustrative embodiments and alternative embodiments of the present disclosure. Having thus described exemplary embodiments of the present disclosure, it should be noted by those skilled in the art that the within disclosures are exemplary only, and that various other alternatives, adaptations, and modifications may be made within the scope of the present disclosure. Merely listing or numbering the steps of a method in a certain order does not constitute any limitation on the order of the steps of that method.

Many modifications and other embodiments of the disclosure will come to mind to one skilled in the art to which this disclosure pertains having the benefit of the teachings presented in the foregoing descriptions and the associated drawings. Although specific terms may be employed herein, they are used in a generic and descriptive sense only and not for purposes of limitation. Accordingly, the present disclosure is not limited to the specific embodiments illustrated herewith, but is limited only by the following claims.

What is claimed is:

1. A system for providing a real-time bi-directional charge capture-centralized conversation between an at least one Billing entity and an at least one Provider entity comprising:
   a first computer apparatus having a first processor, a first memory, a first network connection, and a first non-transitory computer readable medium with a computer apparatus charge capture module installed thereon said first non-transitory computer readable medium;
   a second computer apparatus having a second processor, a second memory, a second network connection, and a second non-transitory computer readable medium with a computer apparatus billing module installed thereon said second non-transitory computer readable medium; and
   a database server capable of provisioning a secure point-to-point connection with each of said first computer apparatus via said first network connection and said second computer apparatus;
   wherein the first and second computer apparatuses in combination with the database server allow the at least one Billing entity and the at least one provider entity to:
   perform at least one action in said charge capture module on said first computer apparatus from a group of actions consisting of entering a message associated with a real-time charge capture data, entering a message associated with a real-time claim data, editing said real-time claim data, said messages comprising an at least one of: a request for supplemental information, a request for clarification, a request for correction, and responses to said requests;
   package a data resulting from said plurality of actions into a data package;
   transmit said data package from said first computer apparatus to said database server via said first secure point-to-point connection;
   gather said data package into a threaded conversation as an updated version of said real- time charge capture-centralized conversation data wherein said Billing entity utilizes said second secure point-to-point access and said Provider entity utilizes said first secure point-to-point connection to perform further actions from said group of actions thereby updating said data package and said threaded conversation; and
   cooperatively assemble a healthcare claim for a reimbursement based upon data in said real-time charge capture-centralized conversation data.

2. The system of claim 1, wherein the first computer apparatus is configured to receive and/or transmit via a plurality of secured communication links:
   an at least one set of said real-time charge capture data;
   an at least one set of said real-time charge capture centralized conversation data; and
   an at least one set of said real-time claim data;
   wherein the at least one set of real-time charge capture data, the at least one set of real time charge capture-centralized conversation data, and the at least one set of real-time claim data are presented in a threaded conversation.

3. The system of claim 2, wherein the second computer apparatus is configured to receive and/or transmit the at least one set of real-time charge capture centralized-conversation data, wherein the at least one set of real-time charge capture-centralized conversation data further comprises:
   the at least one set of real-time charge capture data, and wherein the at least one set of real-time charge capture data and the at least one set of real-time charge capture-centralized conversation data can be combined to create the at least one complete set of real-time claim data.

4. The system of claim 3, wherein the at least one Billing entity and the at least one Provider entity, utilizing either the first computer apparatus or the second computer apparatus, are equally able to initiate, transmit or modify any of the at least one set of real-time charge capture data or the at least one set of real-time charge capture-centralized conversation data.

5. A method for providing real-time bi-directional health care charge capture-centralized conversation between a Billing entity and a Provider entity regarding a real-time charge capture data and a real-time claim data within a secure network, said method comprising the steps of:
   providing a first computer apparatus having a display and having a first secure point-to-point connection to a database server and a second computer apparatus having a display and having a second secure point-to-point access to said database server, said first and said second computer apparatuses having a charge capture module, said charge capture module having secure access to a real-time charge capture-centralized conversation data stored on said database server;
   loading an interface thereon said first computer apparatus, said interface having a charge capture interface, a billing interface and a messaging interface;
   displaying said interface on said display of said first computer apparatus;
   loading said charge capture module via said network thereon said first computer apparatus;
   performing at least one action in said charge capture module on said first computer apparatus from a group of actions including: entering a message associated with said real-time charge capture data, entering a message associated with said real-time claim data, editing said real-time claim data, and combinations thereof, said messages comprising a request for supplemental information, a request for clarification, a request for correction, responses to said requests, or combinations thereof;
   packaging a data resulting from said plurality of actions into a data package; and
   transmitting said data package from said first computer apparatus to said database server via said first secure point-to-point connection;
   gathering said data package into a threaded conversation as an updated version of said real-time charge capture-centralized conversation data; and
   cooperatively assembling a healthcare claim for reimbursement based upon data in said real-time charge capture-centralized conversation data.

6. The method of claim 5, further composing a step of loading an interface from said database server thereon said second computer apparatus.

7. The method of claim 5, wherein said Billing entity utilizes said second secure point-to-point access and said Provider entity utilizes said first secure point-to-point connection to perform further actions from said group of actions thereby updating said data package and said threaded conversation.

8. The method of claim 7, further comprising a step of submitting said charge capture data for a reimbursement.

9. The method of claim 6, wherein said interface comprises a charge capture interface, a billing interface, and a messaging interface.

10. The method of claim 9, further comprising a step of displaying said interface on said display of said second computer apparatus.

11. The method of claim 10, further comprising a step of loading said charge capture module via said network thereon said computer apparatus.

12. The method of claim 11, further comprising a step of performing at least one action in said charge capture module on said second computer apparatus from a group of actions including: entering a message associated with said real-time charge capture data, entering a message associated with said real-time claim data, editing said real-time charge capture data, and combinations thereof as said real-time charge capture centralized conversation data.

13. The method of claim 12, further comprising a step of transmitting said real-time charge capture-centralized conversation data from said second computer apparatus to said database server.

14. The method of claim 13, further comprising a step of storing said real-time charge capture-centralized conversation data from said second computer apparatus on said non-transitory computer readable medium connected to said database server.

15. The method of claim 14, further comprising a step of transmitting said updated real-time charge capture-centralized conversation data to said second computer apparatus from said database via said second secure point-to-point connection.

16. The method of claim 15, further comprising a step of receiving said updated real-time charge capture-centralized conversation data from said first computer apparatus on said database server and further performing said plurality of actions in said charge capture module on said second computer apparatus in order to further update said updated real-time charge capture-centralized conversation data by utilizing said second secure point-to-point connection.

17. The method of claim 5, wherein said group of actions performed in said charge capture module on said first computer apparatus further includes attaching an attachment to said real-time charge capture-centralized conversation data.

18. The method of claim 17, wherein said attachment to said real-time charge capture-centralized conversation data is a picture.

19. The method of claim 17, wherein said attachment to said real-time charge capture-centralized conversation is a form.

20. The method of claim 16, further comprising the steps of sorting said real-time charge capture data and said real-time claim data by said Provider entity, sorting said real-time charge capture-centralized conversation data, marking said charge capture data finalized, and submitting said charge capture data for payment.

* * * * *